United States Patent
Kakehashi et al.

(10) Patent No.: US 7,394,340 B2
(45) Date of Patent: Jul. 1, 2008

(54) ELECTROMAGNETIC DEVICE, HIGH-VOLTAGE GENERATING DEVICE, AND METHOD FOR MAKING THE ELECTROMAGNETIC DEVICE

(75) Inventors: Hidenori Kakehashi, Takatsuki (JP); Takashi Kanbara, Moriguchi (JP); Toru Fujiwara, Akashi (JP); Kenichi Takamatsu, Niigata (JP); Tomoyuki Nakano, Sakai (JP); Kazuhiko Kinutant, Niigata (JP); Takaaki Chuzawa, Hirakata (JP); Masaki Satou, Niigata (JP); Takao Miyai, Hirakata (JP)

(73) Assignee: Matsushita Electric Works, Ltd., Osaka (JP)

( * ) Notice: Subject to any disclaimer, the term of this patent is extended or adjusted under 35 U.S.C. 154(b) by 0 days.

(21) Appl. No.: 11/548,353

(22) Filed: Oct. 11, 2006

(65) Prior Publication Data
US 2007/0132535 A1  Jun. 14, 2007

Related U.S. Application Data

(63) Continuation of application No. 10/129,105, filed as application No. PCT/JP01/08022 on Sep. 14, 2001, now Pat. No. 7,142,082.

(30) Foreign Application Priority Data
Sep. 14, 2000  (JP) ............................. 2000-280666
Jan. 19, 2001  (JP) ............................. 2001-012224

(51) Int. Cl.
*H01F 27/28*  (2006.01)
*H01F 27/34*  (2006.01)

(52) U.S. Cl. ...................... 336/180; 336/181; 336/182; 29/605

(58) Field of Classification Search .......... 336/180–182
See application file for complete search history.

(56) References Cited

U.S. PATENT DOCUMENTS
3,617,966 A    11/1971   Trench et al.
(Continued)

FOREIGN PATENT DOCUMENTS
CN         85104717         12/1986
(Continued)

OTHER PUBLICATIONS
English Language Abstract of JP 11-016752.
(Continued)

*Primary Examiner*—Anh T Mai
(74) *Attorney, Agent, or Firm*—Greenblum & Bernstein, P.L.C.

(57) ABSTRACT

An electromagnetic device and a high-voltage generating device which are thin and improved in the characteristics are provided in which a magnetic core is made of a cylindrical form of a ferrite material having a higher intrinsic resistance. A winding is provided by winding a flat rectangular wire conductor in an edge-wise winding form directly on substantially the entire length of the magnetic core. As any insulator such as a coil bobbin is not needed between the flat rectangular wire conductor and the magnetic core, the winding can be decreased in the overall size or thickness thus contributing to the dimensional reduction of the electromagnetic device. Also, as its flat rectangular wire conductor is wound directly on the magnetic core, the winding can be minimized in the length and thus the overall resistance. Moreover, as there is no gap between the winding and the magnetic core, the self-inductance can be reduced while the size and the number of turns of the winding remain unchanged.

4 Claims, 47 Drawing Sheets

U.S. PATENT DOCUMENTS

| | | | |
|---|---|---|---|
| 4,437,019 A | 3/1984 | Chass | |
| 4,821,134 A | 4/1989 | Niwa | |
| 5,847,518 A | 12/1998 | Ishiwaki | |
| 5,977,855 A | 11/1999 | Matsumura et al. | |
| 6,049,163 A | 4/2000 | Masuda et al. | |
| 6,144,280 A | 11/2000 | Amada et al. | |
| 6,624,596 B1 | 9/2003 | Ohsawa et al. | |
| 6,650,529 B1 | 11/2003 | Murata et al. | |

FOREIGN PATENT DOCUMENTS

| | | | |
|---|---|---|---|
| EP | 1040970 | | 10/2000 |
| JP | 60-119708 | | 8/1985 |
| JP | 02198113 | * | 8/1990 |
| JP | 2-222509 | | 9/1990 |
| JP | 5-109554 | | 4/1993 |
| JP | 11-016752 | | 1/1999 |
| JP | 11-074132 | | 3/1999 |
| JP | 11-114674 | | 4/1999 |
| JP | 11-297547 | | 10/1999 |
| JP | 2000-036416 | | 2/2000 |
| JP | 2000-040629 | | 2/2000 |
| JP | 2000-124040 | | 4/2000 |
| JP | 2000-150266 | | 5/2000 |
| JP | 2000-173840 | | 6/2000 |

OTHER PUBLICATIONS

English Language Abstract of JP 11-074132.
English Language Abstract of JP 11-114674.
English Language Abstract of JP 2000-036416.
English Language Abstract of JP 2000-150266.
English Language Abstract of JP 2000-124040.
English Language Abstract of JP 60-119708.
English Language Abstract of JP 5-109554.
English Language Abstract of JP 2000-040629.
English Language Abstract of JP 2000-173840.
English Language Abstract of JP 2-222509.
English Language Abstract of JP 11-297547.
English Language Abstract of CN 85104717.

* cited by examiner

FIG. 18
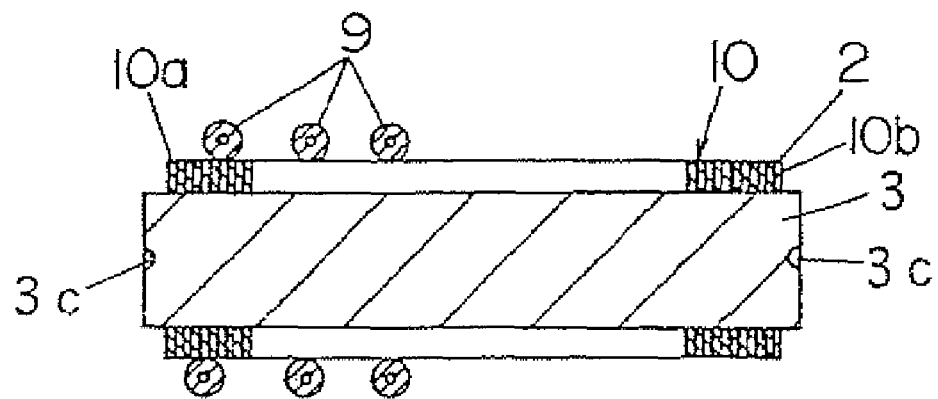
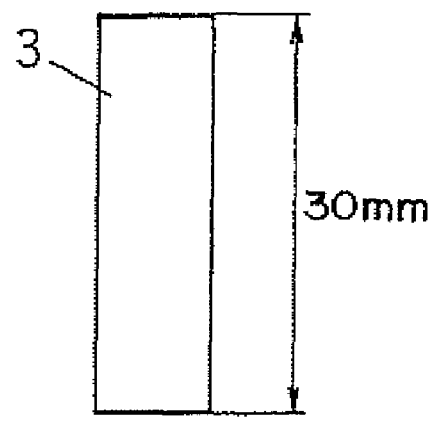
FIG. 19a
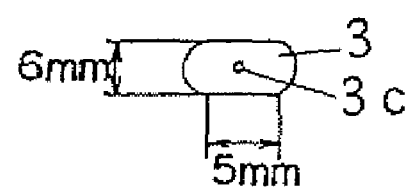
FIG. 19b

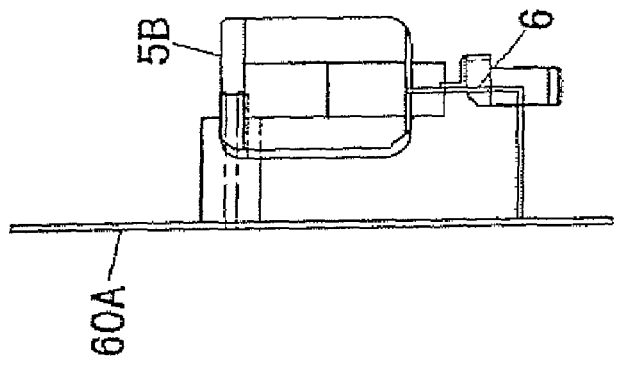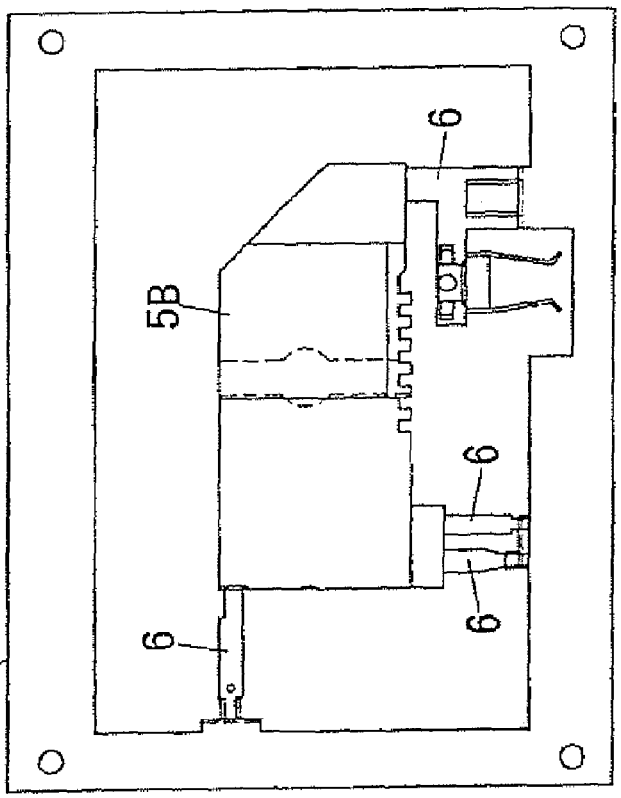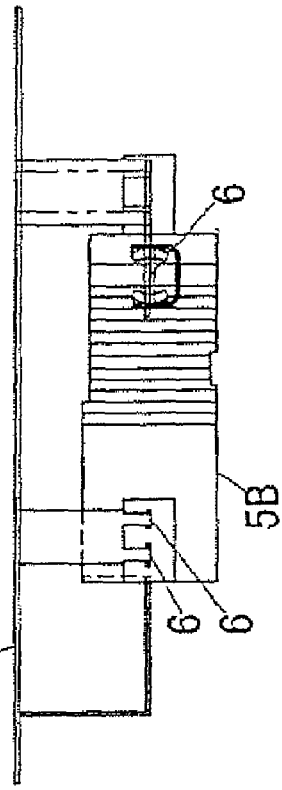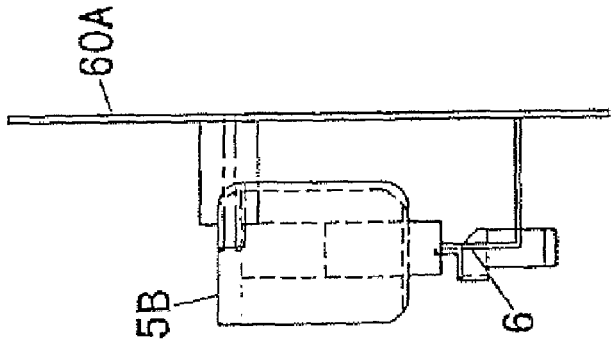

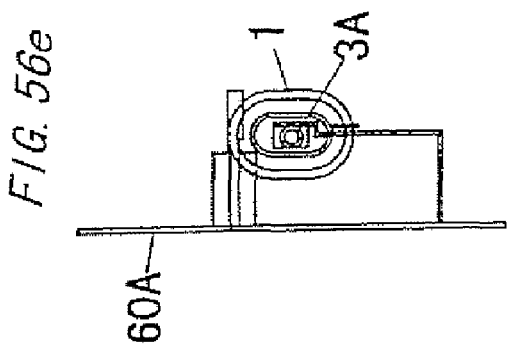
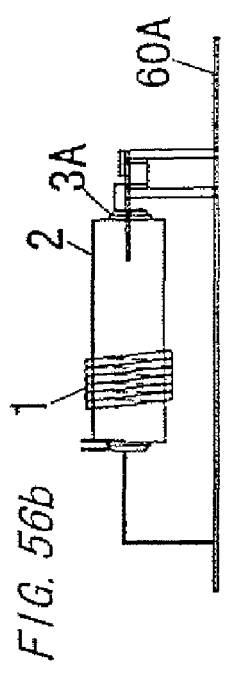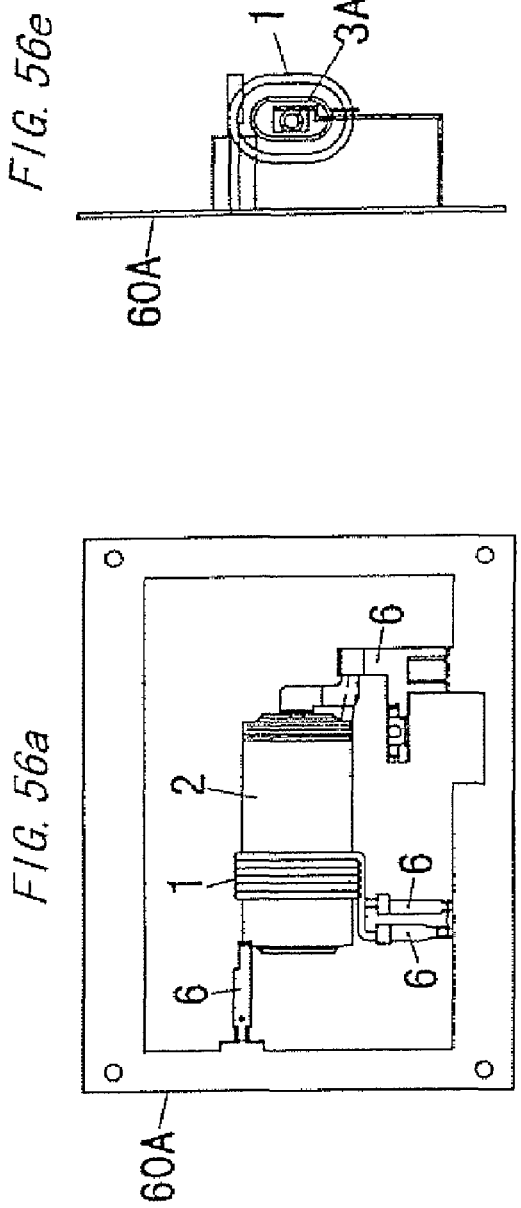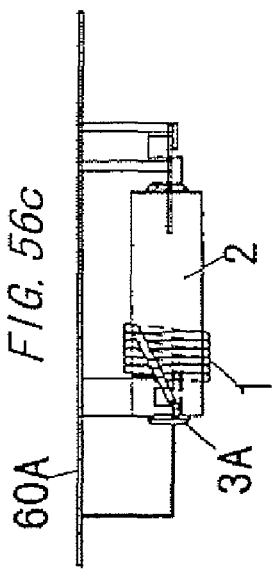
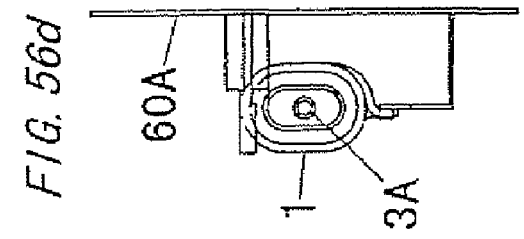

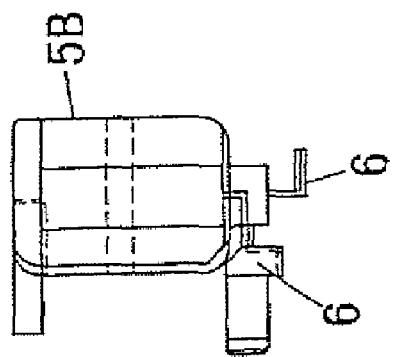
FIG. 58d
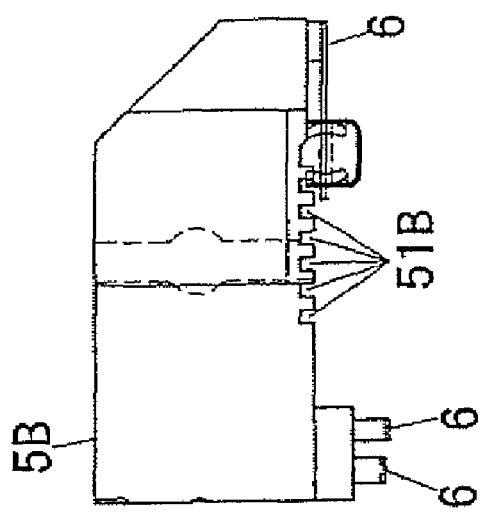
FIG. 58a
FIG. 58b
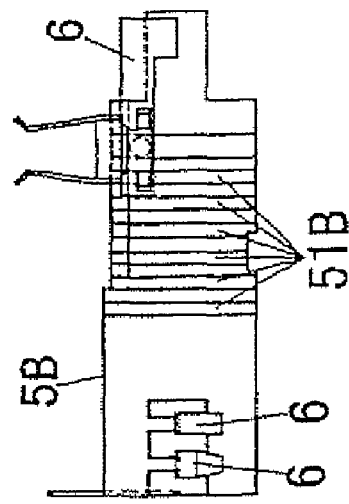
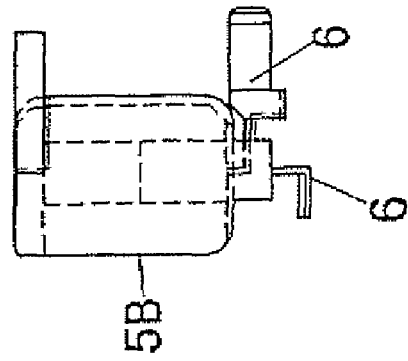
FIG. 58c

ELECTROMAGNETIC DEVICE, HIGH-VOLTAGE GENERATING DEVICE, AND METHOD FOR MAKING THE ELECTROMAGNETIC DEVICE

CROSS-REFERENCE TO RELATED APPLICATIONS

This application is a continuation of pending U.S. patent application Ser. No. 10/129,105, filed Jun. 7, 2002, which is a U.S. National Stage Application of PCT/JP01/08022, filed on Sep. 14, 2001, the disclosures of which are expressly incorporated herein by reference in their entirety.

FIELD OF THE INVENTION

The present invention relates to an electromagnetic device, a high-voltage generating device, and a method for making the electromagnetic device.

BACKGROUND OF THE INVENTION

It is necessary for starting a high intensity discharge lamp such as a high-intensity discharge (HID) lamp to use a high-voltage generating device called an igniter. The high-voltage generating device is generally provided in the form of an electromagnetic device such as a pulse transformer for converting a low-voltage input to a high-voltage output of pulsed waveform (as disclosed in, for example Japanese Patent Laid-open Publications 11-16752 and 11-74132).

One of such conventional electromagnetic devices is shown in structure in FIGS. 65 to 68. A coil bobbin 60 is made of an insulating material such as synthetic resin having substantially a cylindrical shape which comprises two outer flanges 61 at both ends and a partition flange 62 between the two outer flanges 61. A primary winding 63 at the low voltage side is wound between one of the two outer flanges 61 and the partition flange 62 while a secondary winding 64 at the high voltage side is wound between the other outer flange 61 and the partition flange 62. In particular, the secondary winding 64 is fabricated by winding a long, flat rectangular foil conductor with its wider sides facing each other (in the form of, so-called, edge-wise winding) for improving both the edge side insulation and the contact area of windings. Finally, a couple of U-shaped magnetic cores 65 made of Mn—Zn ferrite are inserted and joined to both ends of the coil bobbin 60 with the primary winding 63 and the secondary winding 64, hence forming an electromagnetic device (a pulse transformer).

FIG. 69a is a perspective view of another conventional electromagnetic device and FIG. 69b is a cross sectional view taken along the line A-A' of FIG. 69a. The another conventional electromagnetic device comprises a bar-like magnetic core 3PA and a coil winding 2 wound as the secondary winding on a coil bobbin 60 thereof mounted on the magnetic core 3PA. For ease of winding the coil winding 2 on the coil bobbin 60 secured to the magnetic core 3PA, a recess 31PA is provided in each end of the magnetic core 3PA to determine its position along the axial direction. A process of fabricating the bar-like magnetic core 3PA having the recess in each end thereof will be explained referring to FIG. 70. The process of fabricating the magnetic core 3PA employs a pair of rods K, each having a projection K1' for shaping the recess 31PA and a swage die U having a through hole U1 provided therein for insertion of the rods K. As shown in FIG. 70a, the process starts with shaping the magnetic core 3PA using the die U and the rods K. Then, the lower rod K is lifted up to the upper end of the die U as shown in FIG. 70b to remove the magnetic core 3PA from the die U in the direction denoted by the arrow for increasing the efficiency. The magnetic core 3PA may however be injured at the edge R1 of the recess 31PA upon being removed from the die U as shown in FIG. 71.

FIG. 72 is a perspective view of a further conventional electromagnetic device. The electromagnetic device shown is a pulse transformer for converting a low voltage input to a high voltage output as called an igniter to generate a high voltage for energizing a high intensity discharge lamp. The conventional device shown in FIG. 72 comprises a bar-like magnetic core 3PA, a bobbin 4PA, a pair of coil windings 9 and 10 mounted on the bobbin 4PA mounted to the magnetic core 3PA, a casing 5PA made of a resin material for enclosing those components therein, and terminals 6 connected to coil windings 9 and 10 at one end and extending at the other end from the casing 5PA. The coil winding 9 incorporates an insulation coated wire (of round wire) comprising an electrical conductor having a round shape in the cross section and an insulating coating provided over the wire conductor and serving as the primary winding while the coil winding 10 serves as the secondary winding. The coil winding 9 is connected to one (61) of the terminals 6 and the coil winding 10 is connected to another (62).

This conventional electromagnetic device is fabricated by winding the coil windings 9 and 10 on the bobbin 4PA, inserting the magnetic core 3PA into the bobbin 4PA, assembling those in the casing 5PA, connecting the terminals 6 to the corresponding coil windings 9 and 10, and filling the casing 5PA with an amount of epoxy resin (by vacuum filling process).

FIG. 73 is a perspective view of a conventional welding joiner welded to the insulation coated wire. A welding joiner 6PA which can be welded to the insulation coated wire without stripping the insulation coating comprises, as shown in FIG. 73, a flat base portion 61 extending along one direction and a folded portion 62 extending from one side of the base portion 61 at a right angle to the direction and folded along its width at a portion 63 so that the two portions 61 and 62 confront each other. The welding joiner 6PA is preferably utilized as the terminal 6 of the conventional electromagnetic device. One example of this arrangement is disclosed in Japanese Patent Laid-open Publication 11-114674.

It is common that high intensity discharge lamps are widely used as the head lights of vehicles because they are high in the brightness, low in the power consumption, and long in the operating life and thus much favorable in the safety than any halogen lamps. As such high intensity discharge lamps have increasingly been popular, the electromagnetic devices are now desired for minimizing the thickness in view of the dimensional requirements of igniters. However, the conventional devices are hardly reduced in the thickness with the coil bobbin 60 provided between the magnetic core 65 (See FIG. 65) and the coil. Also, there is essentially provided a gap between the coil bobbin 60 and the magnetic core 65 for ease of mounting, thus elongating the distance between the magnetic core 65 and the coil and creating differences in the properties between the electromagnetic devices. Although a modification is proposed where the coil bobbin is replaced by an insulating cover made of a resin material (disclosed in Japanese Patent Laid-open Publication 2000-36416), it retains the same drawbacks.

When the bobbin is provided between the magnetic core and the coil windings, its terminals are fixedly connected to the coil windings. In case of a bobbin-less device, the terminals connected with the coil windings may be secured with much difficulty.

The process of fabricating an electromagnetic device shown in FIG. 72 requires substantially four or more hours for carrying out the major processing steps including preparation, drying, and curing steps. For implementing a scheme of mass production, extra investments for expanding the existing production facility has to be needed. Also, when the epoxy resin vacuum filling process is employed, it may limit the lead-out of the terminals 6 from the casing 5PA to one single direction. This prevents the terminals 6 from being respectively bent and oriented in a desired pattern of the circuitry planning. Since the coil windings of a metallic material create undesired events of spring back, their ends have to be bound together or supported by any proper means. The epoxy resin vacuum filling process may generally develop an interface between the casing 5PA and the epoxy resin material thus allowing a high voltage to leak from the interface. The edge-wise winding may cause the coating of the coil windings to be peeled off when its curvature radius is too small.

The convention welding joiner 6PA may often cause the insulation coated wire to be dislocated when held between the base portion 61 and the folded portion 62 and pressed with a pair of welding electrodes. If worse, the insulation coated wire may completely be slipped off from between the base portion 61 and the folded portion 62. As the welding of the insulation coated wire to the welding joiner is carried out only with poor consistency, it is much desired to modify the welding joiner for improvement of its stable joining function and operational reliability.

The present invention has been developed in view of the foregoing aspects and its object is to provide an electromagnetic device, a high-voltage generating apparatus, and a method for making the electromagnetic device where the dimensional reduction and the improvement of properties are achieved, and the duration of time required for carrying out the production steps is minimized.

DISCLOSURE OF THE INVENTION

In the present invention, an electromagnetic device comprises a magnetic core having a curved side and a flat rectangular wire conductor wound in an edge-wise winding form directly on the curved side of the magnetic core. Accordingly, as any insulator such as a coil bobbin is not needed between the flat rectangular wire conductor and the magnetic core, the winding can be decreased in the overall size or thickness, thus contributing to the dimensional reduction and the improvement of characteristics of the device. In the device, the magnetic core has an intrinsic resistance of not smaller than 1000 Ω·m.

The electromagnetic device further comprises a winding provided on the outer surface of the flat rectangular wire conductor. Accordingly, a resultant transformer can be reduced in the thickness.

The magnetic core is rough finished at the surface. Accordingly, as no extra step such as polishing is needed after the completion of the magnetic core, the production cost of the magnetic core can be lowered. Also, the flat rectangular wire conductor can be protected from slipping and tilting down during the edge-wise winding process.

The flat rectangular wire conductor and the winding are joined to each other by fusing their coatings. Accordingly, as the positioning between the windings is securely determined, variations in the properties resulting from relative dislocation between the windings will be avoided.

The magnetic core of an edge-wise winding form of the flat rectangular wire conductor is located between a group of leads joined together. Accordingly, the winding is arranged with its leads extending over the outer surface of the flat rectangular wire conductor.

The electromagnetic device further comprises a first insulating member arranged of a cylindrical shape to which the magnetic core of the flat rectangular wire conductor is fitted and a secondary insulating material covering over the first insulating member and the winding which is made of an electrically conductive resin material and provided on the outer side of the first insulating member. Accordingly, the insulation between the winding of the flat rectangular wire conductor and the winding of the electrically conductive resin material can be ensured by the first insulating material.

The first insulating member has a groove provided in the outer side thereof and the winding is fabricated by filling the groove with an electrically conductive resin material. Accordingly, the insulation between the high-voltage end of the winding of the flat rectangular wire conductor and the winding of the electrically conductive resin material can be ensured. The flat rectangular wire conductor serves as a secondary winding and the winding serves as a primary winding.

The primary winding is located adjacent to the low-voltage end of the secondary winding. Accordingly, the surface distance between the high-voltage side of the secondary winding and the primary winding can be increased thus improving the insulating function.

One of two ends of the primary winding disposed at the high-voltage end side of the secondary winding is drawn to the low-voltage end of the secondary winding. Accordingly, the insulation can be improved to a desired level.

The primary winding is an insulated wire or a magnet wire protected with an insulation coating for electrically insulating between the primary winding and the secondary winding. Accordingly, the insulation can be improved to a desired level.

The magnetic core has an elliptical shape in the cross section and its flat rectangular wire conductor is drawn out at both ends through a space between a transformer consisting mainly of the magnetic core and the flat rectangular wire conductor and a rectangular housing mounted outwardly of the transformer. Accordingly, the transformer can be reduced in both the size and the cost.

The magnetic core has a bottomed hole provided in each end thereof and the hole is arranged of a tapered shape which becomes gradually smaller in the diameter from the opening to the bottom. Accordingly, when the magnetic core is fallen down about the point at the edge of its bottom with its bottomed hole accepting the projection of the rod during the preparation of the magnetic core using the paired rods and a pair of punching dies, its portion about the bottomed hole can clear the projection of the rod. As a result, the magnetic core can be protected from being tipped off at its edge about the bottomed hole of its bottom.

The magnetic core has an elliptical shape in the cross section. Accordingly, the overall size can be thinned.

In the present invention, an electromagnetic device having a transformer arrangement includes a bar-like magnetic core and a flat rectangular wire conductor wound on the outer surface of the magnetic core for generation of a high voltage, the flat rectangular wire conductor drawn out at both ends from two ends of the magnetic core respectively, characterized by a resin outer housing provided about the transformer by filling or molding an insulating resin material and having at least one side thereof configured up and down along a direction substantially parallel with the axial direction of the magnetic core. Accordingly, as the surface distance is increased by the effect of the up and down configuration, the insulation function can be improved.

The up and down configuration is provided at the high-voltage end side of the flat rectangular wire conductor. Accordingly, the insulation function can be improved.

In the present invention, an electromagnetic device having a transformer arrangement includes a magnetic core, a winding and a flat rectangular wire conductor both provided on the magnetic core, and at least two terminals for connection of the winding and the flat rectangular wire conductor with the outside, characterized in that the transformer is sealed in an injection molded form of a thermoset resin material. Accordingly, the production of the transformer can be simplified.

The electromagnetic device further comprises a lead frame for supporting the components during the injection molding. Accordingly, the production can be simplified.

The thermoset resin material is covered with a molded form of a thermoplastic resin material. Accordingly, the insulation can be ensured while the protection against moisture is effectively improved.

The winding and the flat rectangular wire conductor are secured at least at one end with an adhesive. Accordingly, the coil winding can hardly be loosened by the effect of spring back.

While the winding acts as a primary winding, the flat rectangular wire conductor acts as a secondary winding and is insulated by coating and provided in an edge-wise winding form on the magnetic core. Accordingly, the overall size can be minimized.

In the present invention, an insulation coated wire is joined with a welding joiner which comprises a flat base portion extending in one direction and a folded portion extending from one side along the one direction of the base portion substantially at a right angle to the one direction, where the folded portion is folded down along the one side to face the base portion, and the base portion has a tab portion extending from the other side than the one side thereof and bent upright to form a positional error inhibitor. Accordingly, when the welding joiner is pressed by welding electrodes for joining, the insulation coated wire can securely be held with but not detached from the welding joiner and its joining can hence be maintained and improved in both the stability and the durability.

The length of the tab positional error inhibiting portion from the base portion is equal to or slightly greater than the diameter of the insulation coated wire. Accordingly, as the insulation coated wire when dislocated is securely held by the positional error inhibitor of the welding joiner, it can definitely remain protected from being detached from the welding joiner.

The positional error inhibiting portion is distanced from the folded portion. Accordingly, as any short-circuit between the positional error inhibiting portion and the folded portion is avoided, Joule heat generated by energization can successfully be radiated from the extending side of the folded portion of the joiner.

In the present invention, a high-voltage generating device comprises: a pulse transformer having a magnetic core, a flat rectangular wire conductor wound in an edge-wise winding form directly on the outer surface of the magnetic core, and a winding provided on the outer side of the flat rectangular wire conductor; a capacitor connected in parallel with the primary winding of the pulse transformer; a switching element for opening and closing the discharging path extending from the capacitor to the primary winding; and a resistor connected to the primary winding. Accordingly, as any insulator such as a coil bobbin is not needed between the magnetic core and the winding (of the flat rectangular wire conductor), the winding can be decreased in the overall size or thickness thus implementing a thin, property improved high-voltage generating device. Also, as its undesired oscillation is attenuated by resistance loss in the resistor connected in parallel with the primary winding, the pulsed high-voltage output of the secondary winding of the pulse transformer can favorably be corrected to substantially a fundamental waveform. Moreover, since the oscillation of the voltage is readily settled down, any unwanted stress on the components including the capacitor can successfully be eased. As a result, the components to be used may be declined in the resistance to high voltage and reduced in the size and the cost.

In the present invention, a high-voltage generating device comprises: a pulse transformer having a magnetic core, a flat rectangular wire conductor wound in an edge-wise winding form directly on the outer surface of the magnetic core, and a winding provided on the outer side of the flat rectangular wire conductor; a capacitor connected in parallel with the primary winding of the pulse transformer; a switching element for opening and closing the discharging path extending from the capacitor to the primary winding; and metal strips provided adjacent to at least one end of the pulse transformer in an open magnetic circuit. Accordingly, as any insulator such as a coil bobbin is not needed between the magnetic core and the winding (of the flat rectangular wire conductor), the winding can be decreased in the overall size or thickness thus implementing a thin, property improved high-voltage generating device.

The pulse transformer, the capacitor, and the switching element are installed in a housing which has a socket for connecting the base of a discharge lamp electrically and mechanically, whereby the base of the discharge lamp is supplied with a pulsed high voltage generated at the secondary winding of the pulse transformer. Accordingly, a thin, property improved high-voltage generating device can be realized having the socket for connection to the base of a discharge lamp.

In the present invention, a method for making an electromagnetic device comprises the steps of: winding a flat rectangular wire conductor in an edge-wise winding form on a magnetic core; and fixedly joining ends of the flat rectangular wire conductor provided in the edge-wise winding form to corresponding terminals which are provided integrally on a single metal strip. Accordingly, the duration required for the production can be decreased. Also, with no use of insulators, the ends of the coil winding can be joined to the corresponding terminals.

In the above method, the metal strip is arranged of a linear form to which the ends of the flat rectangular wire conductor are joined as drawn out in one direction towards the metal strip. Accordingly, the metal strip can be arranged of a simple shape.

In the method, as the ends of the flat rectangular wire conductor have fixedly been joined to the corresponding terminals of the metal strip, the redundancy of the metal strip is separated from the terminals for electrically isolating the ends of the flat rectangular wire conductor from the metal strip. Accordingly, the electromagnetic device with its coil winding joined at the ends to the corresponding terminals with no use of insulators can be fabricated by using simpler steps.

In the method, the magnetic core has an elliptical shape in the cross section. Accordingly, the downsizing and the cost down can be feasible.

In the present invention, a method for making an electromagnetic device with the use of a winding jig for holding one end of a magnetic core, a center shaft for supporting the center axis of the magnetic core, a hold-down jig arranged slidable on the magnetic core and the center shaft, a hold-down spring urging a stress against the hold-down jig, and a spring holder arranged slidable in response to the width of winding, comprises the steps of: coupling one end of a flat rectangular wire conductor to the winding jig joined to the magnetic core and rotating the winding jig; winding the flat rectangular wire conductor on the magnetic core which is rotated by the rotating action of the winding jig; and allowing the hold-down jig and the spring holder to be slid to protect the flat rectangular wire conductor from tilting down as the width of winding increases during the edge-wise winding of the flat rectangular wire conductor on the magnetic core between the winding jig and the hold-down jig.

BRIEF DESCRIPTION OF THE DRAWINGS

FIG. 18 is a cross sectional view of the same;

FIG. 19 illustrates a magnetic core in the embodiment where FIG. 19a is a front view and FIG. 19b is a side view of the same;

FIG. 53 is a plan view of the electromagnetic device shown in FIG. 52;

FIG. 56 is a plan view of the electromagnetic device shown in FIG. 55;

FIG. 58 is a plan view of the electromagnetic device shown in FIG. 57;

BEST MODES FOR EMBODYING THE INVENTION

Embodiment 1

Figure 1:
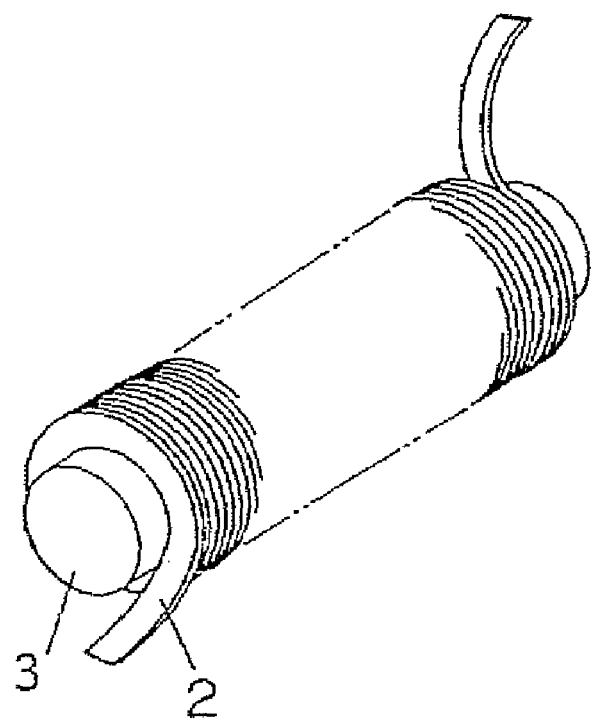
FIG. 1 is a perspective view showing Embodiment 1 of the present invention.
Figure 2:
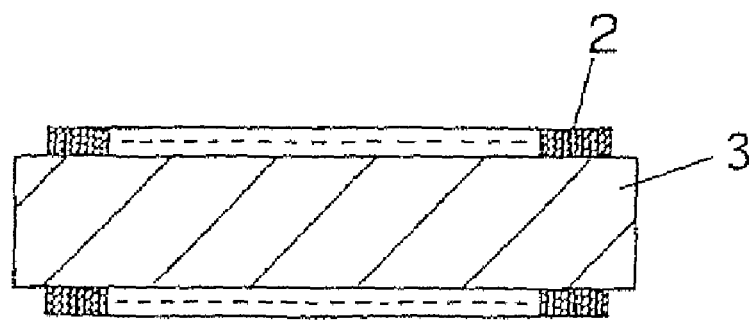
FIG. 2 is a cross sectional view of the same.

An electromagnetic device of this embodiment is a single-winding inductor having a winding wound directly on a rod magnetic core 3 arranged of substantially a cylindrical shape with no need of an insulator such as a coil bobbin as shown in FIGS. 1 and 2.

The magnetic core 3 is made of an Ni—Zn ferrite material which is high in the resistivity (intrinsic resistance) and about 8 mm in the diameter of its cylindrical shape. The winding is a flat rectangular wire conductor 2 (for example, having a thickness of 70 μm and a width of 1.4 mm) wound in a single layer of edge-wise winding form on substantially the entire length of the magnetic core 3. More specifically, the flat rectangular wire conductor 2 is wound on the magnetic core 3 which is secured at both axial ends to jigs and then rotated by a rotating motion of the jigs.

It is found from examination of the insulation coating (not show) of the flat rectangular wire conductor 2 wound on the magnetic core 3 in the inductor of this embodiment that the insulation between the winding (of the flat rectangular wire conductor 2) and the magnetic core 3 and between any two adjacent turns of the winding is highly ensured. Although the insulation between the winding and the magnetic core 3 depends on the resistivity which is one of the insulating properties of the magnetic core 31 it remains explicitly favorable when the resistivity is not smaller than 1000 Ω·m. It is also found that the magnetic and electric properties remain not declined.

As its flat rectangular wire conductor 2 is directly wound in an edge-wise winding form on the magnetic core 3 made of a high-resistivity material, the inductor eliminates the use of any insulator such as the coil bobbin 60 between the winding (of the flat rectangular wire conductor 2) and the magnetic core 3 and can thus be minimized in the thickness with its winding reduced in the external dimensions. Also, as the flat rectangular wire conductor 2 is directly wound on the magnetic core 3, its winding can be shortened in the overall length thus declining the level of resistance. Moreover, as the inductor develops no gap between the winding and the magnetic core 3, its self-inductance can comparatively be decreased with the dimensions and the number of windings remaining unchanged. The conventional electromagnetic device having the flat rectangular wire conductor wound in an edge-wise winding form on an insulator such as the coil bobbin develops a gap between the winding and the magnetic core which then makes the relative positional relationship between the winding and the magnetic core unstable, hence creating variations in the properties including the inductance. Because the flat rectangular wire conductor 2 is directly wound on the magnetic core 3 in the embodiment, they are closely secured to each other and their relative position can be secured thus minimizing variations in the properties.

Embodiment 2

Figure 3:
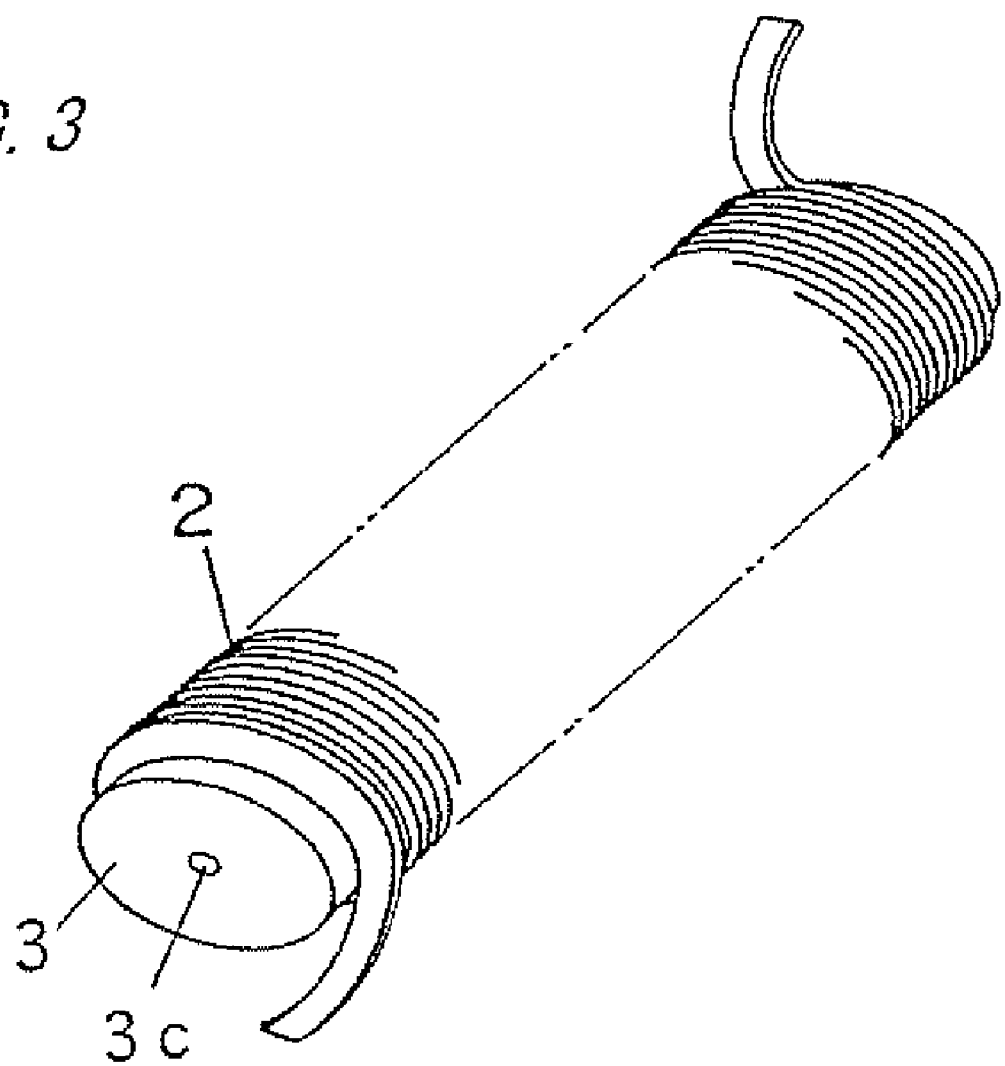
FIG. 3 is a perspective view showing Embodiment 2 of the present invention.

This embodiment is characterized by a magnetic core 3 having an elliptical shape in the cross section as shown in FIG. 3. As the other arrangement is identical to that of Embodiment 1, like components are denoted by like numerals and will be described in no more detail (throughout the embodiments and their drawings).

The magnetic core 3 is made of an Ni—Zn ferrite material identical to that of Embodiment 1 but having an elliptical shape in the cross section on which a flat rectangular wire conductor 2 is directly wound in an edge-wise winding form. As its magnetic core 3 has an elliptical shape in the cross section, the inductor can be lower in the height than that of Embodiment 1.

The magnetic core 3 has a hemispheric recess (pit) 3c of about 2 mm in diameter provided at the center in each end thereof. While the flat rectangular wire conductor 2 is being wound on the magnetic core 3 by the action of a winder 4, the magnetic core 3 is secured to the winder with its recess 3c tightly accepting the corresponding projection of a jig of the winder.

Figure 4:
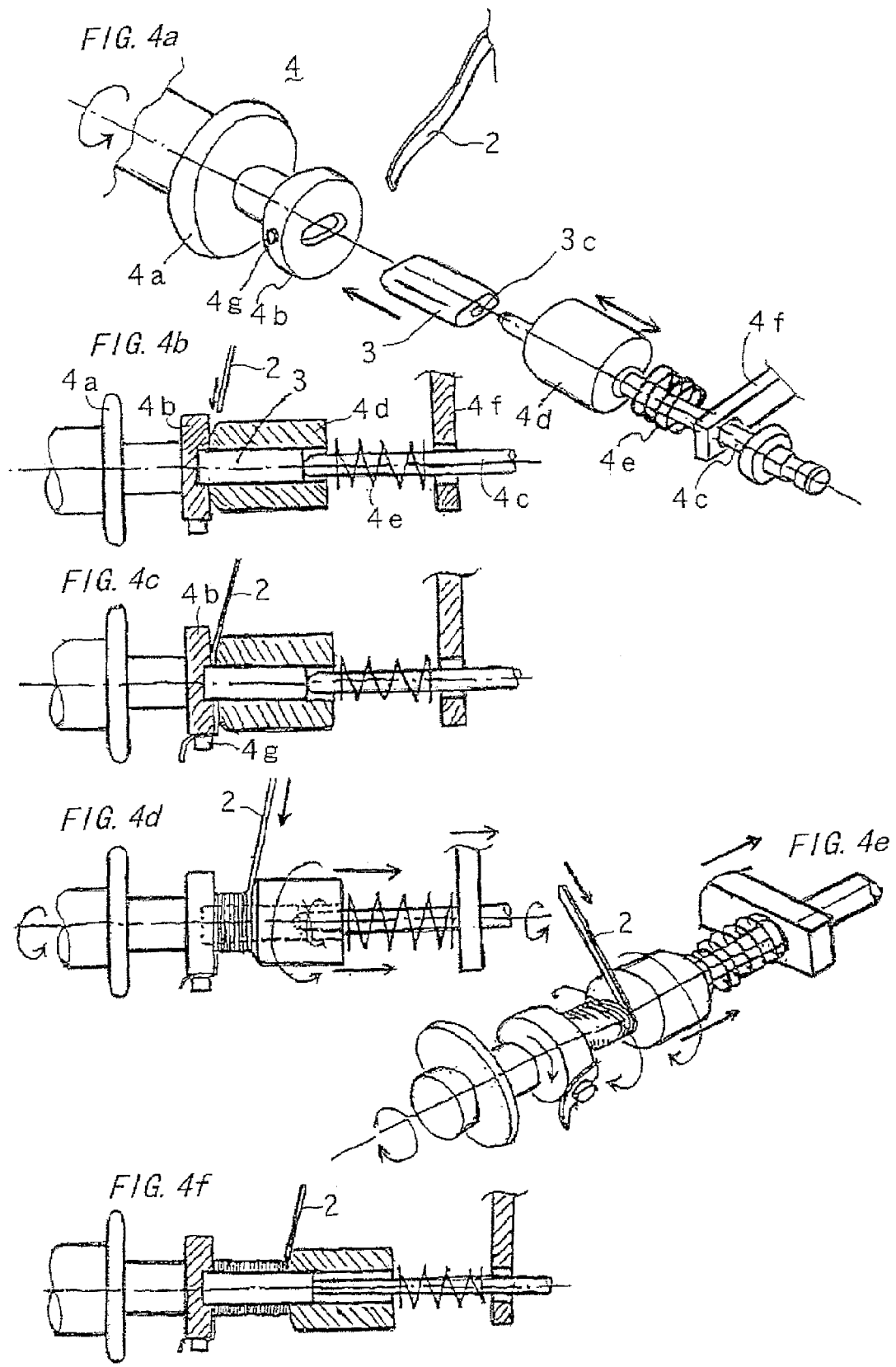
FIG. 4 is an explanatory view illustrating a process of fabricating the same.

This will be explained in more detail referring to FIGS. 4a to 4f. The winder 4 has a magnetic core holding jig 4b mounted on a rotary shaft 4a thereof, as shown in FIG. 4a. The magnetic core 3 is then inserted into the center recess of the magnetic core holding jig 4b and held at its hemispheric recess 3c engaged with the tip of a center shaft 4c of the winder 4. A hold-down jig 4d is also provided for rotating and sliding motion on and along the center shaft 4c. The hold-down jig 4d remains urged by a hold-down spring 4e so as to hold the flat rectangular wire conductor 2 in the vertical position during the edge-wise winding action. Additionally, a slidable spring support 4f is provided for loading the flat rectangular wire conductor 2 with substantially a uniform pressure. As a result, the magnetic core 3 is uniformly held along its axis of rotation and its rotation can be stable with minimum of the rotation error derived from its dimensional variations thus ensuring a stability of the winding action.

Then, with the magnetic core 3 being held by the jigs as shown in FIG. 4b, the flat rectangular wire conductor 2 is joined at the end to a conductor retainer 4g on the magnetic core holding jig 4b as shown in FIG. 4c. As the rotary shaft 4a of the winder 4 starts rotating together with the magnetic core holding jig 4b, the magnetic core 3, the hold-down jig 4d, and the center shaft 4c, the flat rectangular wire conductor 2 is directly wound on the magnetic core 3. As the winding proceeds, an edge-wise winding form of the flat rectangular wire conductor 2 is produced between the magnetic core holding jig 4b and the hold-down jig 4d and its width increases. As the width increases, the hold-down jig 4d and the spring support 4f are shifted together with the yielding length of the hold-down spring 4e kept uniform. This allows the flat rectangular wire conductor 2 to remain at its vertical position, hence ensuring a stability of the winding action. FIG. 4f illustrates the hold-down jig 4d and the spring support 4f shifted to the right by a width of the winding.

As described, the inductor having the flat rectangular wire conductor 2 wound directly on the magnetic core 3 of the elliptical shape in the cross section, like that of Embodiment 1, can be minimized in the size, particularly the height and in the inductance variation.

While the flat rectangular wire conductor is directly wound on the core according to Embodiment 1, the core may be covered with a coating for increasing the level of insulation or protected at the sides (where the flat rectangular wire conductor is wound) with a tape of insulating material. This also allows the flat rectangular wire conductor to be wound by the rotating action of the magnetic core, thus contributing to the small size of the inductor.

Embodiment 3

Figure 5:
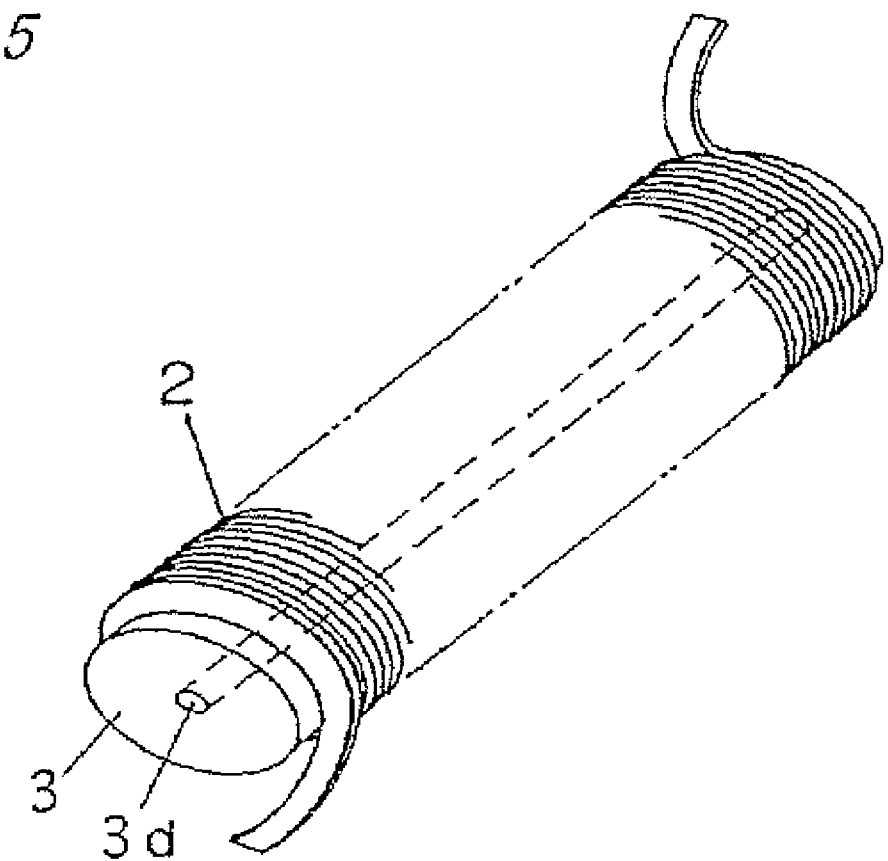
FIG. 5 is a perspective view showing Embodiment 3 of the present invention.
Figure 6:
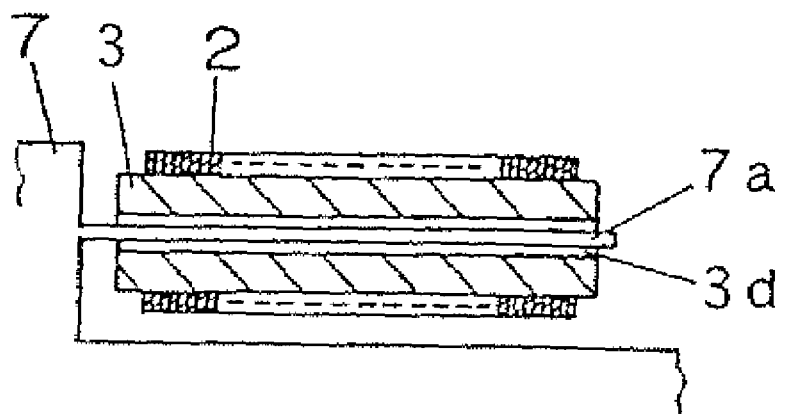
FIG. 6 is a cross sectional view of the same in use.

This embodiment is characterized by a magnetic core 3 having a through hole 3d provided along the axial direction therein as shown in FIG. 5. The magnetic core 3 like that of Embodiment 2 is arranged of an elliptical shape in the cross section and its through hole 3d of about 2 mm in the diameter extends along the axial direction between two ends thereof. This allows the magnetic core 3 to be securely held by a jig inserting into the through hole 3d for ease of the winding of the flat rectangular wire conductor 2. In addition, the magnetic core 3 can tightly be secured to a housing 7 of the winder with its through hole 3d accepting and engaging with a bar-like projection 7a extending from the housing 7, as shown in FIG. 6. The projection 7a may be implemented by a retaining screw. The magnetic core 3 may be arranged of a cylindrical shape similar to that of Embodiment 1.

Embodiment 4

Figure 7:
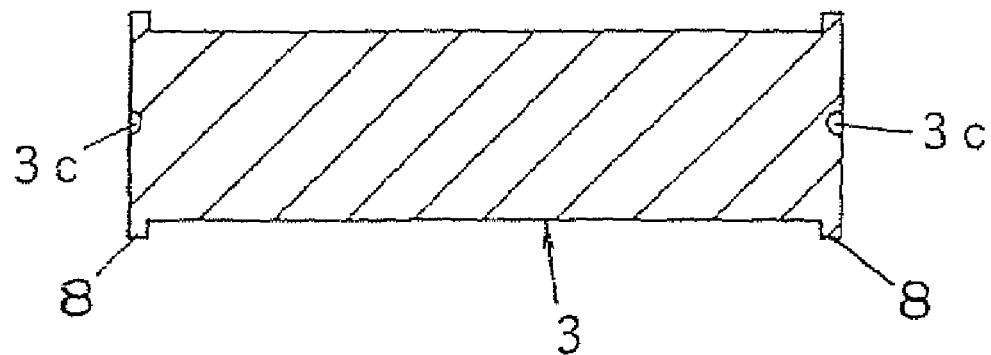
FIG. 7 is a cross sectional view of a magnetic core in Embodiment 4.
Figure 8:
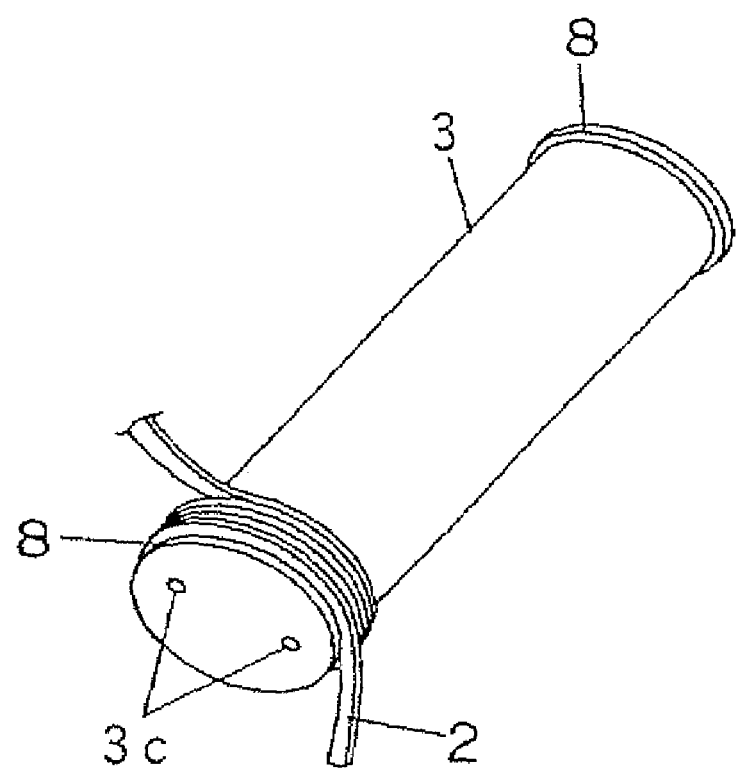
FIG. 8 is a perspective view of the magnetic core on which a flat rectangular wire conductor is being wound.
Figure 9:
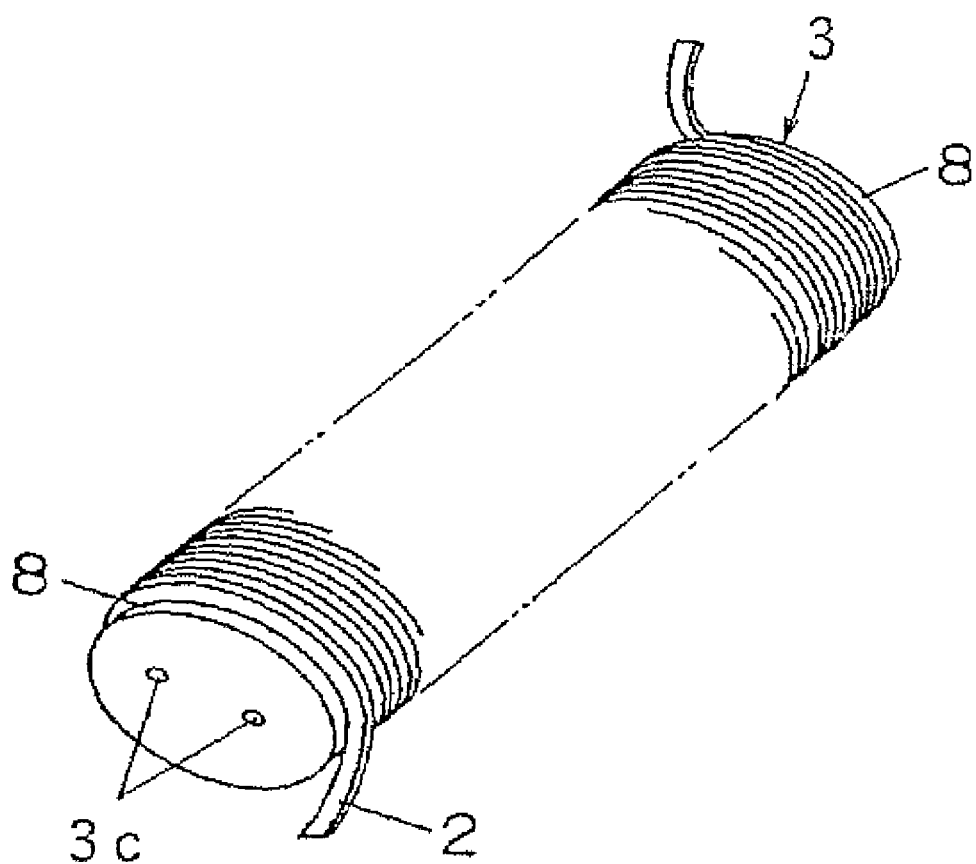
FIG. 9 is a perspective of the same.

This embodiment is characterized by a magnetic core 3 having a pair of outer flanges 8 provided on both ends thereof to extend outwardly, as shown in FIGS. 7 to 9. The magnetic core 3 like that of Embodiment 2 has an elliptical shape in the cross section and its outer flanges 8 project from the lengthwise ends radially (outwardly) at substantially a right angle to the lengthwise direction. When wound in an edge-wise winding form, a flat rectangular wire conductor 2 may be loosened out at both ends of the magnetic core 3. This is inhibited by the outer flanges 8 which holds the flat rectangular wire conductor 2 at the two ends.

Also, a plurality (two in this embodiment) of hemispheric recesses 3c are provided in each end of the magnetic core 3. During the winding of the flat rectangular wire conductor 2, the magnetic core 3 is tightly secured to the winder with its recesses 3c accepting and engaging with corresponding projections of a winder 4 which can rotate. This allows the winding of the flat rectangular wire conductor 2 to be more stable than in Embodiment 2. The magnetic core 3 may be arranged of a cylindrical shape similar to that of Embodiment 1.

Embodiment 5

Figure 10:
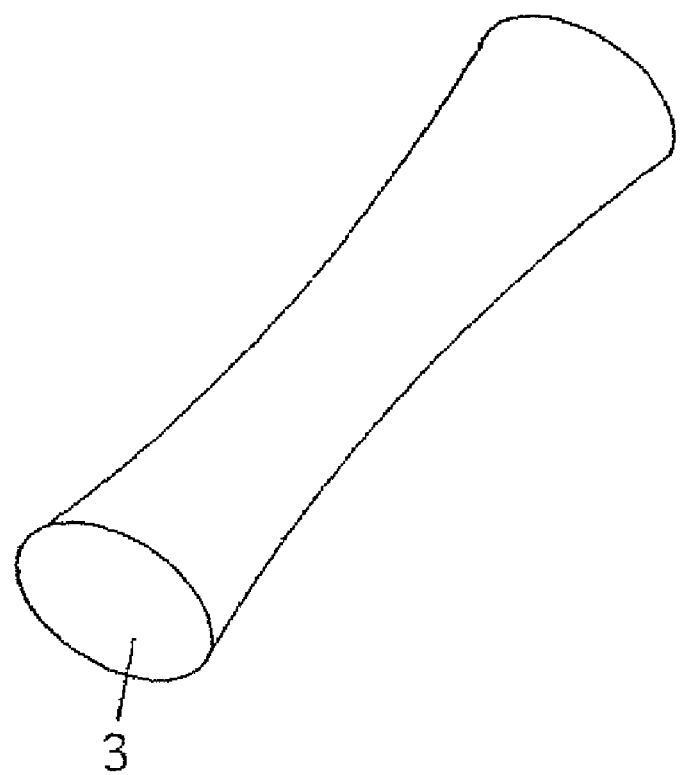
FIG. 10 is a perspective view showing Embodiment 5 of the present invention.
Figure 11:
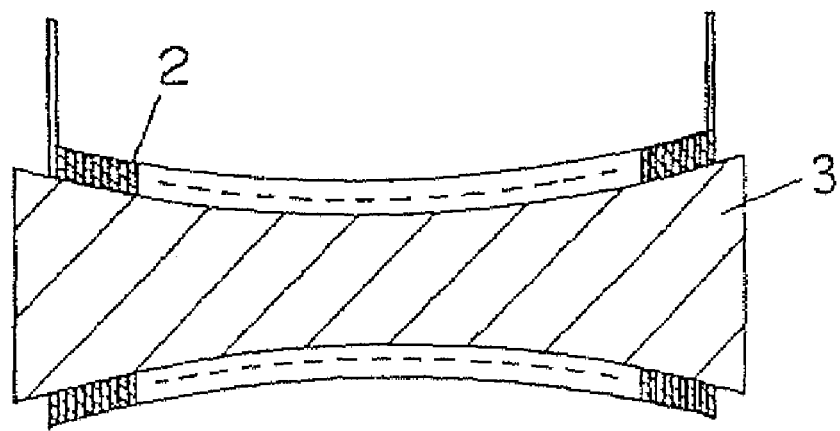
FIG. 11 is a cross sectional view of the same.

This embodiment is characterized by a magnetic core 3 having a particular shape shown in FIGS. 10 and 11. The shape of the magnetic core 3 on which a flat rectangular wire conductor 2 is directly wound in an edge-wise winding form becomes smaller in the diameter of the cross section from both lengthwise ends to the center. Accordingly, the outer surface of the magnetic core 3 is sloped down from the two ends to the center and allows the flat rectangular wire conductor 2 to be closely wound without loosening towards the lengthwise ends of the magnetic core 3, thus ensuring a stability of the winding form. The magnetic core 3 may be arranged of an elliptical shape in the cross section similar to that of Embodiment 2.

Embodiment 6

Figure 12:
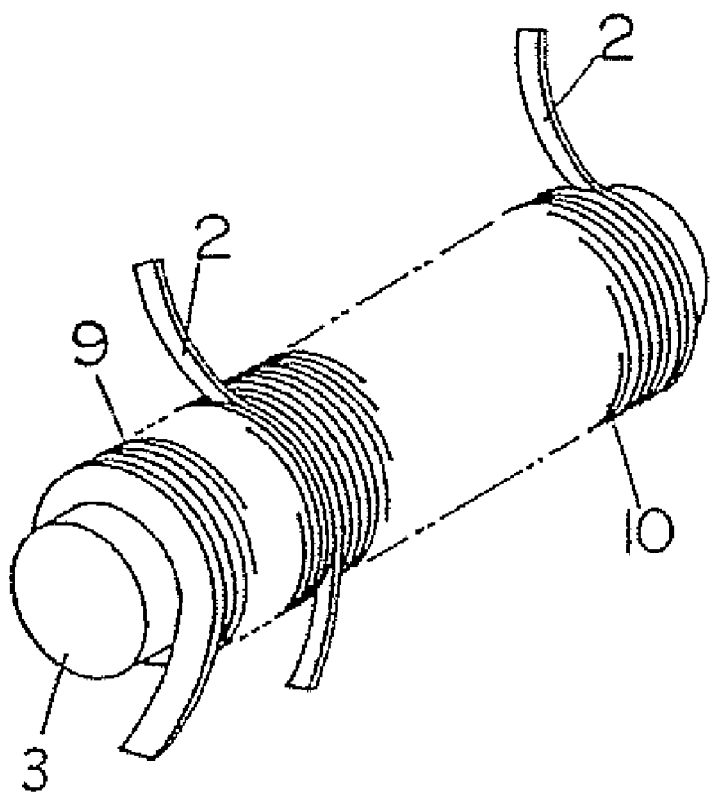
FIG. 12 is a perspective view showing Embodiment 6 of the present invention.

An electromagnetic device of this embodiment is a two-winding transformer having a primary winding and a secondary winding wound directly on a substantially cylindrical, rod-like magnetic core 3 thereof, shown in FIG. 12, with no use of an insulator such as a coil bobbin.

The magnetic core 3 is substantially identical in the construction to that of Embodiment 1 where flat rectangular wire conductors 2 are wound in an edge-wise winding form on the magnetic core 3 to implement the primary winding 9 and the secondary winding 10. As its primary winding 9 and secondary winding 10 are implemented by the edge-wise winding of the flat rectangular wire conductors 2 directly on the magnetic core 3, the transformer can be decreased in the overall size as compared with the conventional arrangement having the windings wound on the coil bobbin and declined in the direct-current resistance of both the primary winding 9 and the secondary winding 10, hence improving its properties. Also, as the primary winding 9 and the secondary winding 10 are separated from each other along the lengthwise direction of the magnetic core 3, the insulation between them can highly be ensured. The magnetic core 3 may be arranged of an elliptical shape in the cross section similar to that of Embodiment 2.

Embodiment 7

Figure 13:
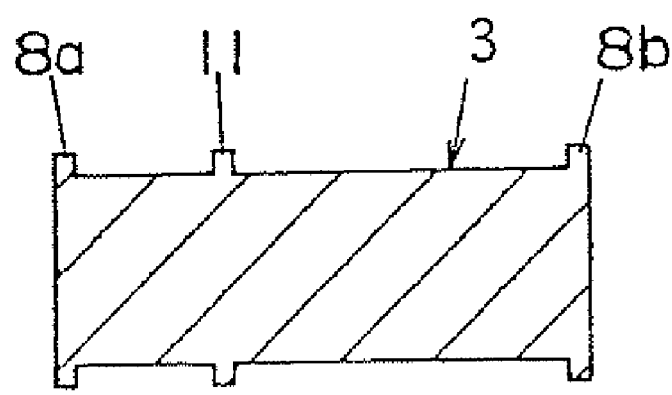
FIG. 13 is a cross sectional view of a magnetic core in Embodiment 7.
Figure 14:
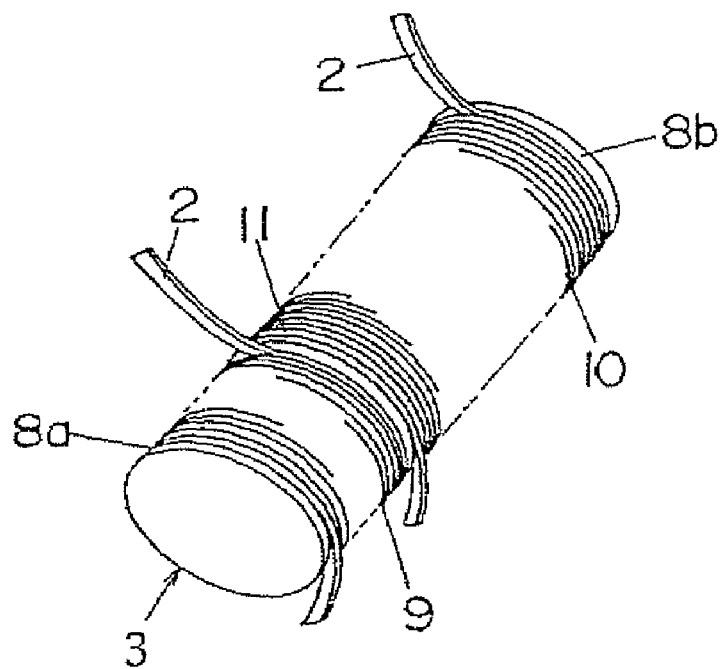
FIG. 14 is a perspective view of the same.

This embodiment is characterized by a magnetic core 3 having a particular shape shown in FIGS. 13 and 14. The magnetic core 3 has a pair of outer flanges 8a and 8b provided on both lengthwise ends thereof to extend radially (outwardly) from their edge at substantially a right angle to the lengthwise direction and a partition flange 11 provided at a region biased from the center to one end thereof to extend radially (outwardly) at substantially a right angle to the lengthwise direction. This allows a flat rectangular wire conductor 2 to be directly wound in an edge-wise winding form between the outer flange 8a and the partition flange 11 on the magnetic core 3 implementing the primary winding 9 and another flat rectangular wire conductor 2 to be directly wound in an edge-wise winding form between the partition 11 and the outer flange 8b on the magnetic core 3 implementing the secondary winding 10.

Accordingly, the outer flanges 8a and 8b can inhibit the edge-wise winding form of the flat rectangular wire conductor 2 from being loosened at the two lengthwise ends of the magnetic core 3 while the partition flange 11 provided between the primary winding 9 and the secondary winding 10 on the magnetic core 3 can definitely separate and electrically insulate the two windings 9 and 10 from each other thus improving the insulation as compared with that of Embodiment 6. The magnetic core 3 may be arranged of an elliptical shape in the cross section similar to that of Embodiment 2.

Embodiment 8

Figure 15:
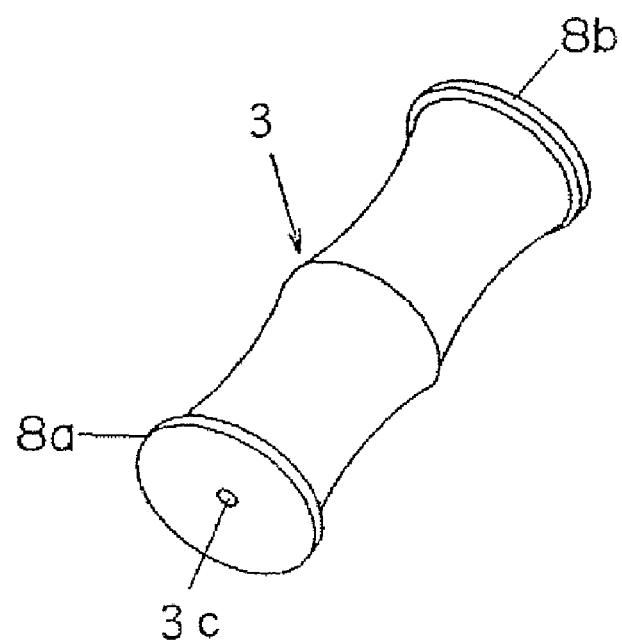
FIG. 15 is a perspective view showing Embodiment 8 of the present invention.
Figure 16:
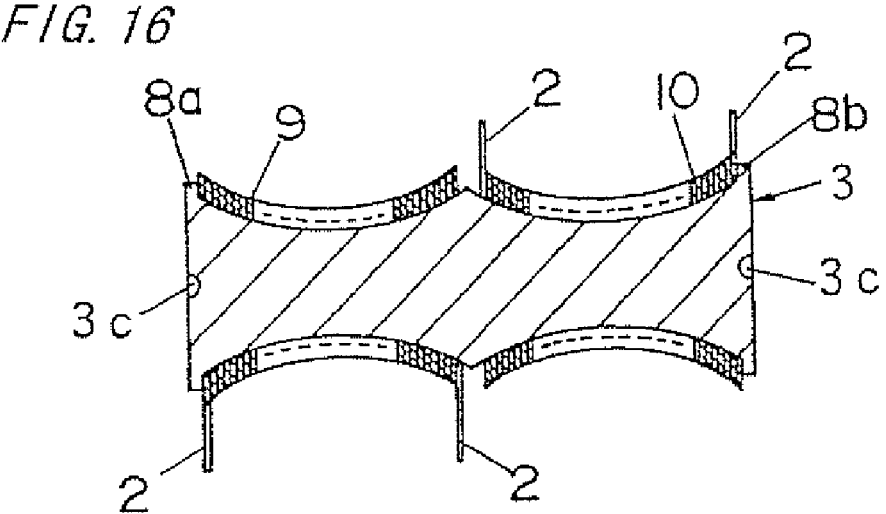
FIG. 16 is a cross sectional view of the same.

This embodiment is characterized by a magnetic core 3 having a particular shape shown in FIGS. 15 and 16. The shape of the magnetic core 3 comprises two halves separated at substantially the center and each half becomes smaller in the diameter of the cross section from each lengthwise end to an intermediate region. Flat rectangular wire conductors 2 are wound in an edge-wise winding form directly on the two halves of the magnetic core 3 thus implementing the primary winding 9 and the secondary winding 10. Similar to Embodiment 2, a recess 3c is provided in each length end of the magnetic core 3.

Each half of the magnetic core 3 on which the primary winding 9 or the secondary winding 10 is directly wound is sloped down from both ends, the lengthwise end and the center of the magnetic core 3, to the intermediate region. This allows the winding of the flat rectangular wire conductor 2 to be securely wound along the lengthwise direction without loosening outwardly at the two ends. Also, the cross section at the center of the magnetic core 3 between the primary winding 9 and the secondary winding 10 is greater than the halves on which the primary winding 9 and the secondary winding 10 are directly wound, the two windings 9 and 10 can be separated and insulated from each other at a higher level of certainty than in Embodiment 6. The magnetic core 3 may be arranged of an elliptical shape in the cross section similar to that of Embodiment 2.

Embodiment 9

Figure 17:
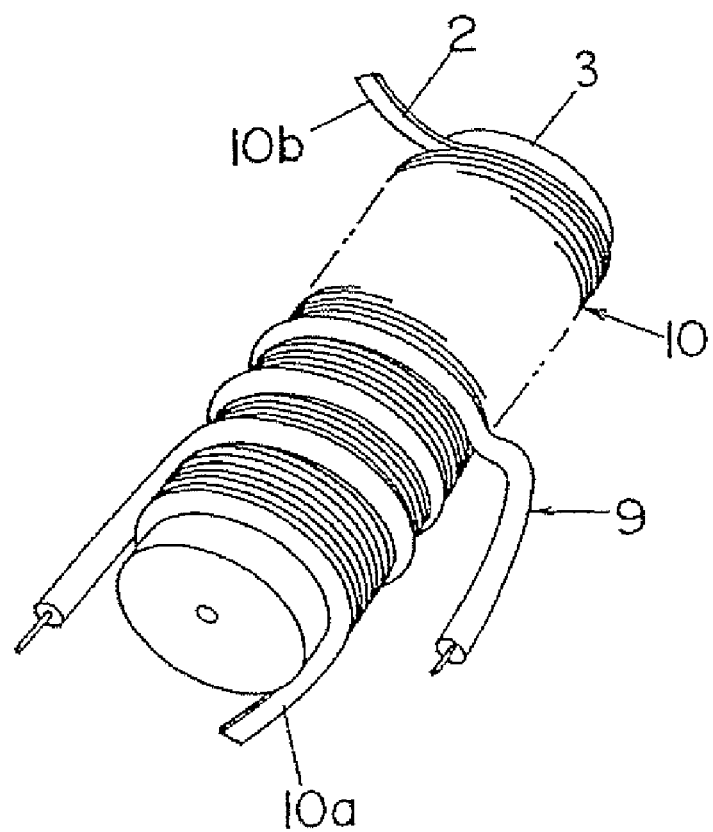
FIG. 17 is a perspective view showing Embodiment 9 of the present invention.

An electromagnetic device of this embodiment is a two-winding transformer having a primary winding and a secondary winding wound directly on a substantially cylindrical, rod-like magnetic core 3 thereof, shown in FIGS. 17 and 18, with no use of an insulator such as a coil bobbin. The magnetic core 3 is made of an Ni—Zn ferrite material and arranged of substantially an elliptical shape, a combination of a rectangular region and two semi-circular regions, in the cross section shown in FIG. 19. In this embodiment, the diameter of the semi-circular regions is about 6 mm while the length of the rectangular region of the cross section is about 5 mm. The magnetic core 3 is about 30 mm in the length. Also, a recess 3c having a diameter of about 2 mm and a depth of about 2 mm is provided in each lengthwise end of the magnetic core 3.

The secondary winding 10 on the magnetic core 3 is fabricated by providing 220 turns of a flat rectangular wire conductor 2 (e.g. 0.070 mm thick and 1.4 mm wide) directly in an edge-wise winding form. It is found that the direct current resistance of the secondary winding 10 is substantially 1.8 Ω. As shown in FIGS. 17 and 18, the primary winding 9 is fabricated by providing 6 turns (3 turns shown in FIGS. 17 and 18) of a wire conductor (e.g. 0.2 mm in the wire conductor diameter and 0.51 mm in the overall diameter) substantially between a low-voltage end 10a of the secondary winding 10 and the lengthwise center of the magnetic core 3 over the secondary winding 10. The wire conductor may be an insulated wire or magnet wire.

Figure 20:
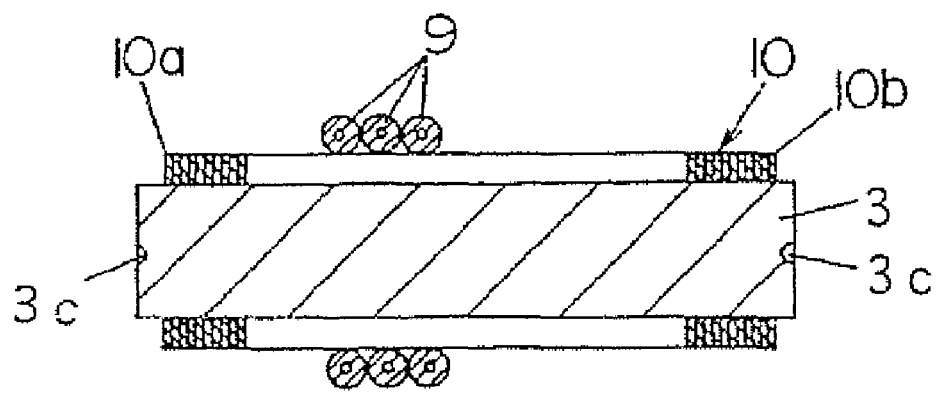
FIG. 20 is a cross sectional view of a modification.

Because of the above described arrangement of this embodiment, the primary winding 9 is wound over the secondary winding 10 thus increasing the magnetic coupling between the two windings 9 and 10 and improving the efficiency of power transmission. As a result, the electromagnetic device of this embodiment can produce a higher secondary voltage as a pulse transformer than the previous embodiment 7 or 8 where the two windings 9 and 10 are separately wound on the magnetic core 3. For example, when the primary voltage is 600 V, the pulsed output can be generated a peak value of 30 kV. Also, as the primary winding 9 is located close to the low-voltage end 10a of the secondary winding 10, it can be separated and insulated by a marginal distance from the high-voltage end 10b of the secondary winding 10. Moreover, since the primary winding 9 is implemented by the coated wire conductor, the insulation between the two windings 9 and 10 can be ensured. The primary winding 9 may be provided adjacent to the low-voltage end 10a of the secondary winding 10 along the lengthwise direction of the magnetic core 3 with equal success, as shown in FIG. 20.

Embodiment 10

Figure 21:
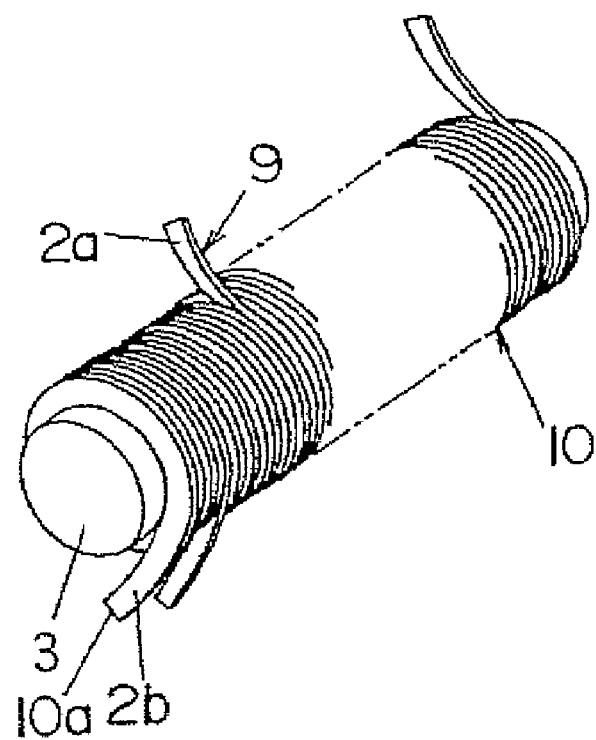
FIG. 21 is a perspective view showing Embodiment 10 of the present invention.
Figure 22:
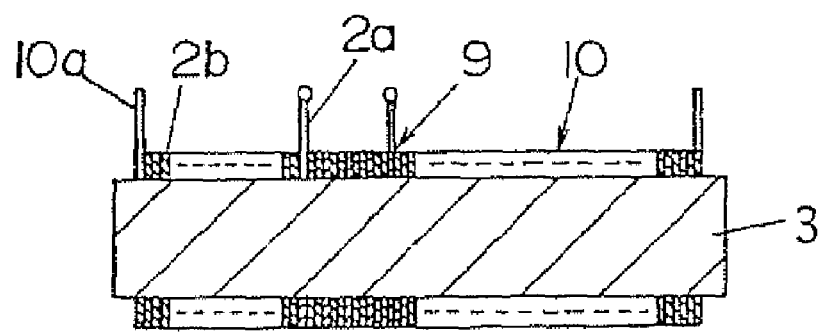
FIG. 22 is a cross sectional view of the same.

An electromagnetic device of this embodiment is a two-winding transformer having flat rectangular wire conductors 2a and 2b wound in an edge-wise winding form directly on a substantially cylindrical rod-like magnetic core 3 thereof with no use of an insulator such as a coil bobbin to implement the primary winding 9 and the secondary winding 10 respectively shown in FIGS. 21 and 22. The magnetic core 3 is substantially identical in the construction to that of Embodiment 1 on which the flat rectangular wire conductor 2b is directly wound in an edge-wise winding form throughout the length thereof to develop the secondary winding 10. Then, the primary winding 9 is fabricated by winding the flat rectangular wire conductor 2a in an edge-wise winding from as alternating several turns with the flat rectangular wire conductor 2b of the secondary winding 10 at a region close to the low-voltage end 10a of the secondary winding 10 of the magnetic core 3.

As the primary winding 9 and the secondary winding 10 are implemented by the edge-wise winding form of the flat rectangular wire conductors 2a and 2b directly on the magnetic core 3, their external dimensions are substantially equal to each other and can thus contribute to the smaller or thinner size of the electromagnetic device than that of Embodiment 9. Also, the flat rectangular wire conductor 2a of the primary winding 9 like the secondary winding 10 is directly wound on the magnetic core 3, the two windings 9 and 10 can be fabricated in one single step thus increasing the productivity.

Embodiment 11

Figure 23:
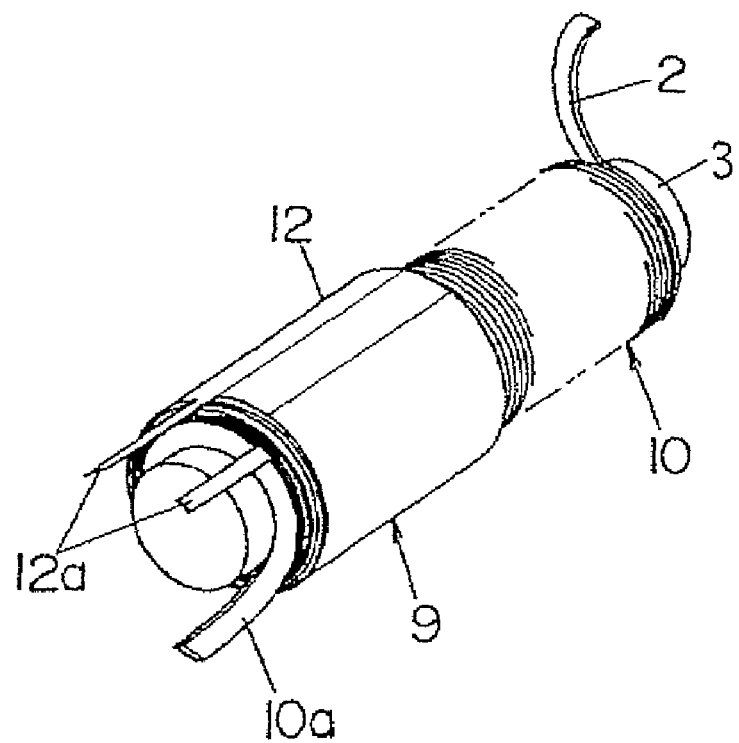
FIG. 23 is a perspective view showing Embodiment 11 of the present invention.
Figure 24:
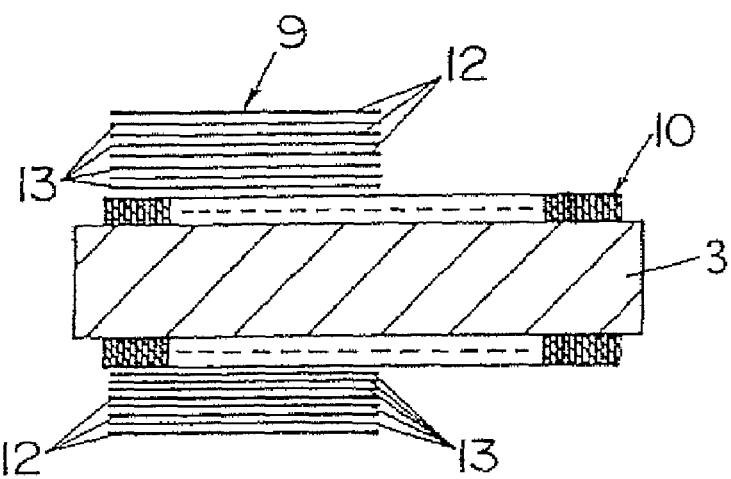
FIG. 24 is a cross sectional view of the same.

This embodiment is characterized by a construction of the primary winding 9 shown in FIGS. 23 and 24. The other arrangement is substantially identical to that of Embodiment 9. The primary winding 9 in this embodiment is fabricated by winding rectangular foils of a wire conductor 12 and a rectangular sheet of an insulating film 13 alternately on the secondary winding 10 which has been fabricated by winding a flat rectangular wire conductor 2 in an edge-wise winding form directly on a magnetic core 3. The conductor foil 12 has a pair of conductors 12a provided on both ends of one side thereof which serve as the terminals of the primary winding 9.

Figure 25:
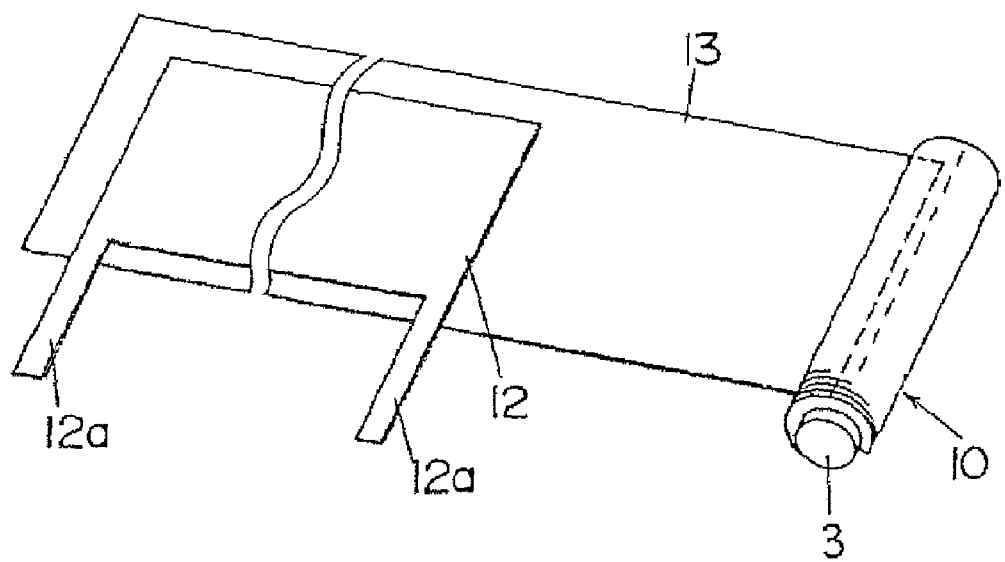
FIG. 25 is an explanatory view illustrating a process of fabricating the same.

The process of fabricating the primary winding 9 is now explained in more detail. As shown in FIG. 25, the wire conductor foil 12 is placed on one end of the insulating film 13 of a rectangular sheet and wound from the other end over the secondary winding 10 provided directly on the magnetic core 3. More specifically, the insulating film 13 is first wound on the secondary winding 10 and then, the wire conductor foil 12 on the insulating film 13 is wound. Accordingly, the conductor foil 12 is alternated with the insulating film 13. As a result shown in FIG. 24, the wire conductor foil 12 is wound in a multi-layer form via the insulating film 13 on the secondary winding 10 to implement the primary winding 9. This allows the insulating film 13 to insulate between the primary winding 9 and the secondary winding 10 and simultaneously between the layers of the wire conductor foil 12. The primary winding 9 of this embodiment is provided between a region close to the low-voltage end 10a of the secondary winding 10 and the lengthwise center of the magnetic core 3.

As its primary winding 9 is fabricated by winding the wire conductor foil 12 and the insulating film 13, an electromagnetic device of this embodiment can further be decreased in the thickness. Also, as the distance between the primary winding 9 and the secondary winding 10 is minimized, the magnetic coupling between the same can be enhanced thus increasing the efficiency of power transmission and thus producing a higher amplitude of the output voltage. Moreover, as the primary winding 9 is increased in the cross section of the wire conductor, its direct current resistance can be reduced hence producing a greater level of the primary current.

Embodiment 12

Figure 26:
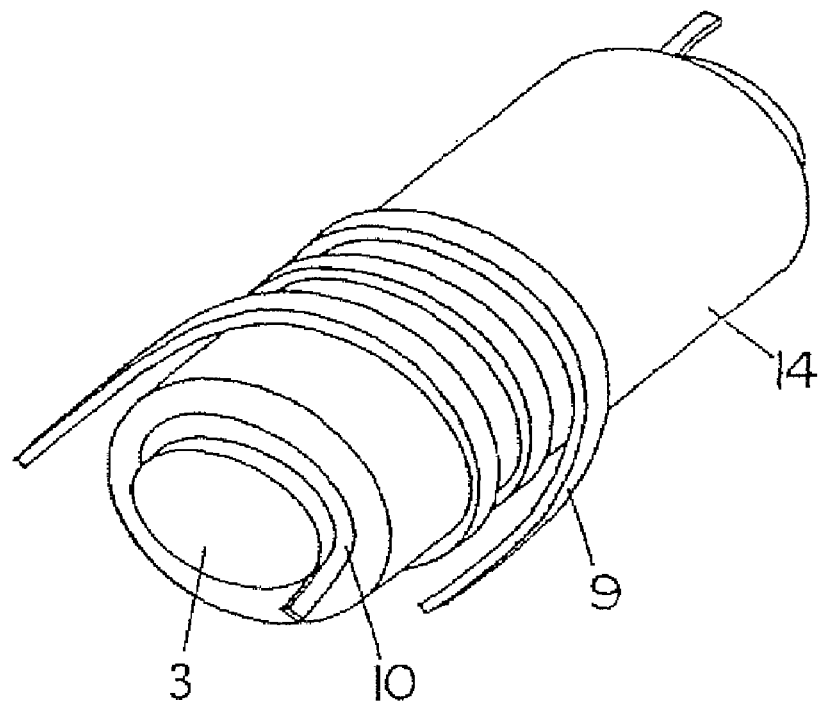
FIG. 26 is a perspective view showing Embodiment 12 of the present invention.
Figure 27:
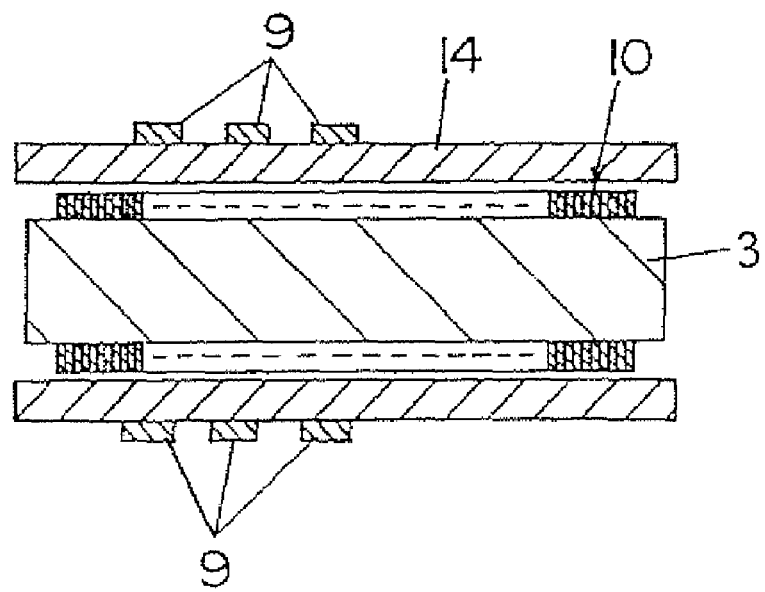
FIG. 27 is a cross sectional view of the same.

This embodiment is characterized by a construction of the primary winding 9 shown in FIGS. 26 and 27. The other arrangement is substantially identical to that of Embodiment 9. The primary winding 9 is fabricated by winding a flat rectangular wire conductor 2 in an edge-wise winding form on a magnetic core 3 to develop the secondary winding 10, installing the magnetic core 3 in a substantially cylindrical insulation casing 14 made of an insulating material, and winding a wire on the insulation casing 14. The insulation casing 14 is sized not shorter than the overall length of the magnetic core 3 to completely enclose the magnetic core 3 and the secondary winding 10 therein. In particular, the primary winding 9 incorporates several turns of the wire (for example, a flat rectangular wire conductor) provided substantially between the low-voltage end 10a of the secondary winding 10 and the lengthwise center of the magnetic core 3.

Because of the above described arrangement of this embodiment, the insulation casing 14 can definitely insulate between the primary winding 9 and the secondary winding 10. Also, as the secondary winding 10 is entirely enclosed in the insulation casing 14, its marginal surface can be protected from dielectric breakdown throughout the length from its high-voltage end 10b to the primary winding 9.

Embodiment 13

Figure 28:
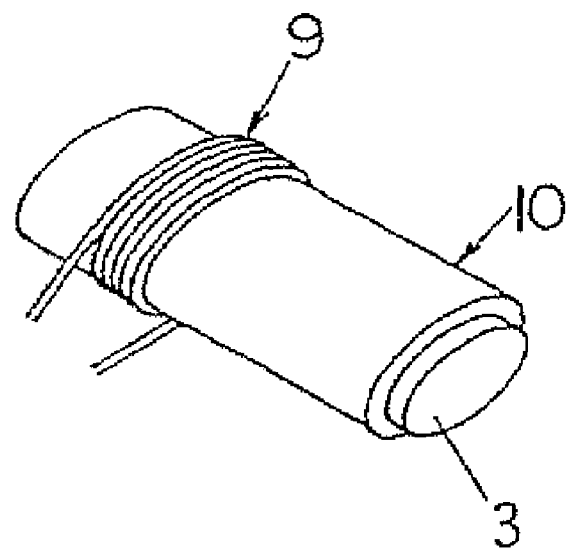
FIG. 28 is a perspective view showing Embodiment 13 of the present invention.

This embodiment is characterized by a construction of the primary winding 9 shown in FIG. 28. The other arrangement is substantially identical to that of Embodiment 9. The primary winding 9 is positioned by winding a fusible resin coated wire on the secondary winding 10 and fusing between the coating of a flat rectangular wire conductor 2 of the secondary winding 10 and the resin coated wire of the primary winding 9.

As the two windings 9 and 10 are bonded to each other by fusion of their coating to determine the position of the primary winding 9, they can be inhibited from relatively dislocating from each other thus eliminating any undesired variation in the properties. The coating of the flat rectangular wire conductor 2 of the secondary winding 10 provided in an edge-wise winding form may be made of a fusible resin material and directly bonded by fusion to the magnetic core 3 for positioning the secondary winding 10.

Embodiment 14

Figure 29:
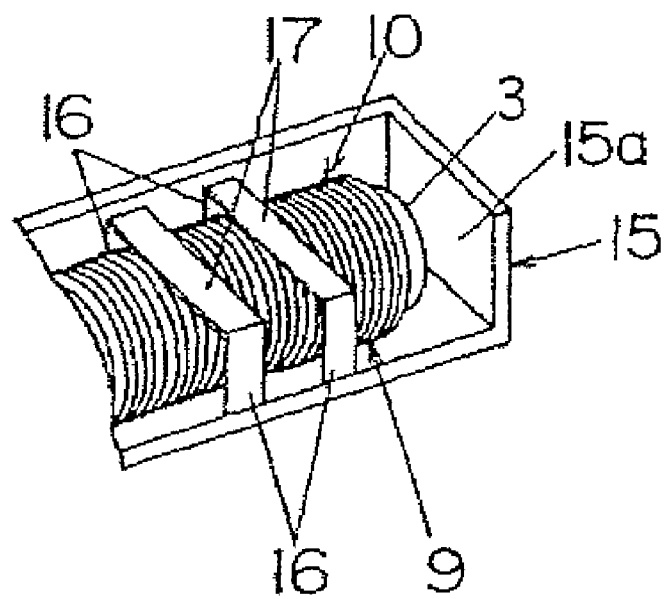
FIG. 29 is a partially omitted perspective view showing Embodiment 14 of the present invention.

This embodiment is characterized by a construction of the primary winding 9 shown in FIG. 29. A magnetic core 3 is provided with leads 16 of thin metal strips fabricated by insertion forming, arranged on which a flat rectangular wire conductor 2 is wound in an edge-wise winding from to develop the secondary winding 10, and installed in the interior 15a of a synthetic resin casing 15. Each pair of the leads 16 provided on both sides of the magnetic core 3 are bridged at their distal end by a thin metal lead strip 17. As the lead strip 17 is joined at both ends to the distal ends of the paired leads 16, they extend about the secondary winding 10 as serving as the primary winding 9 (its two turns only shown in the drawing). This arrangement can contribute to the smaller size or the lower dimension of the electromagnetic device (a transformer) of this embodiment.

Embodiment 15

In Embodiment 9, the primary winding 9 is implemented by the coated wire of which the overall diameter is set to substantially five times greater than the diameter of its wire conductor because of a point of view that a dielectric breakdown between the primary winding 9 and the secondary winding 10 possibly occurs at the marginal surface close to the high-voltage end 10b of the secondary winding 10. However, when the coated wire of such a greater diameter is used, a resultant electromagnetic device (a transformer) becomes greater in dimensions thus interrupting the reduction of the overall size. Also, as the coated wire is round in the cross section, it may hardly be positioned on the secondary winding 10 and, if worse, may be wound to a greater thickness. While the diameter of the wire of the primary winding 9 in Embodiment 12 is successfully decreased, the overall dimensions of the electromagnetic device (transformer) become greater due to the size of the insulation casing 14 and may be increased in the number of components or assembled with much difficulty.

Figure 30:
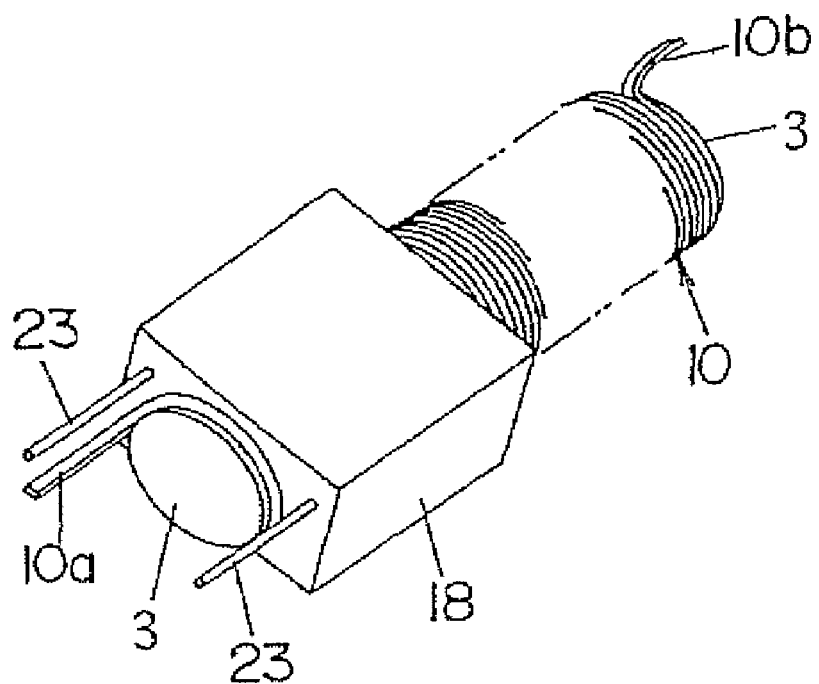
FIG. 30 is a perspective view showing Embodiment 15 of the present invention.
Figure 31:
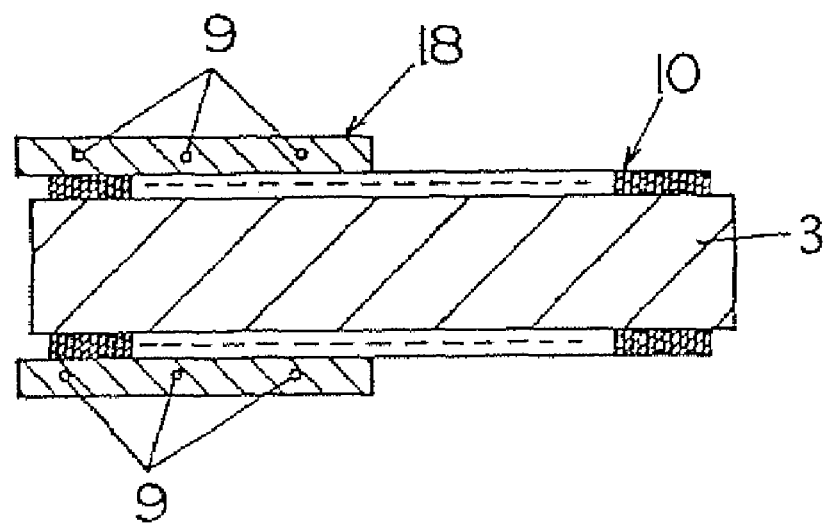
FIG. 31 is a cross sectional view of the same.

This embodiment is an electromagnetic device (a transformer) comprising a primary winding assembly 18 including the primary winding 9 with insulators and a magnetic core 3 having a flat rectangular wire conductor 2 wound in an edge-wise winding form thereon and coupled to the primary winding assembly 18, as shown in FIGS. 30 and 31. While this embodiment is characterized by the installation of the primary winding 9, its other arrangement is identical to that of Embodiment 9.

Figure 32:
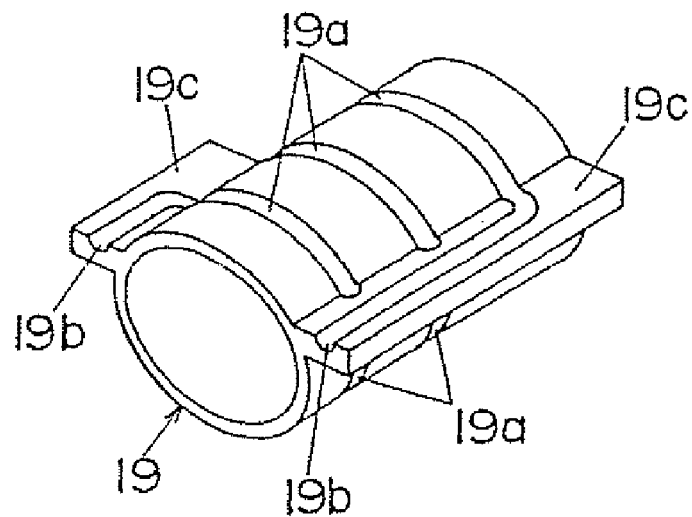
FIG. 32 is a perspective view of a cylindrical body in the same.

The primary winding assembly 18 includes a substantially cylindrical housing 19 of an insulating resin material (a first insulating material) arranged of an elliptical shape in the cross section as shown in FIG. 32. The housing 19 is made of a thermoplastic resin material such as poly-ether-imide and has several turns of a groove 19a provided circumferentially in the outer surface thereof for holding the primary winding. Also, the housing 19 has a couple of lengthwisely extending projections 19c provided thereon, each projection having a groove 19b provided thereon for accepting each end of the primary winding.

Figure 33:
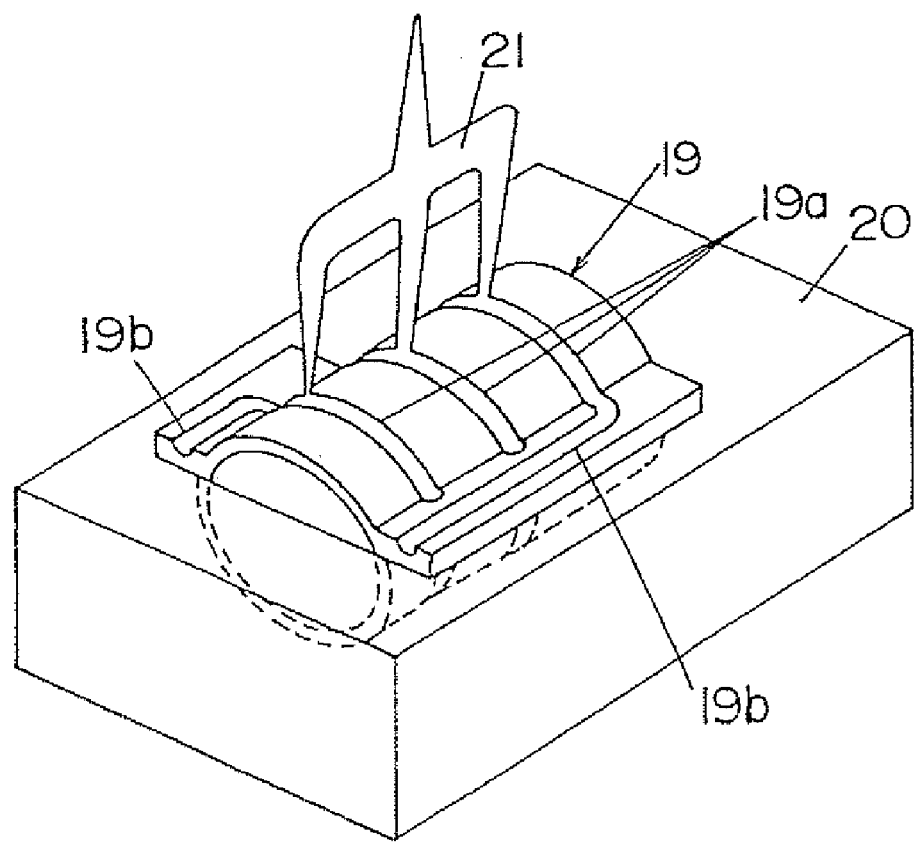
FIG. 33 is an explanatory view showing a process of fabricating the same.
Figure 34:
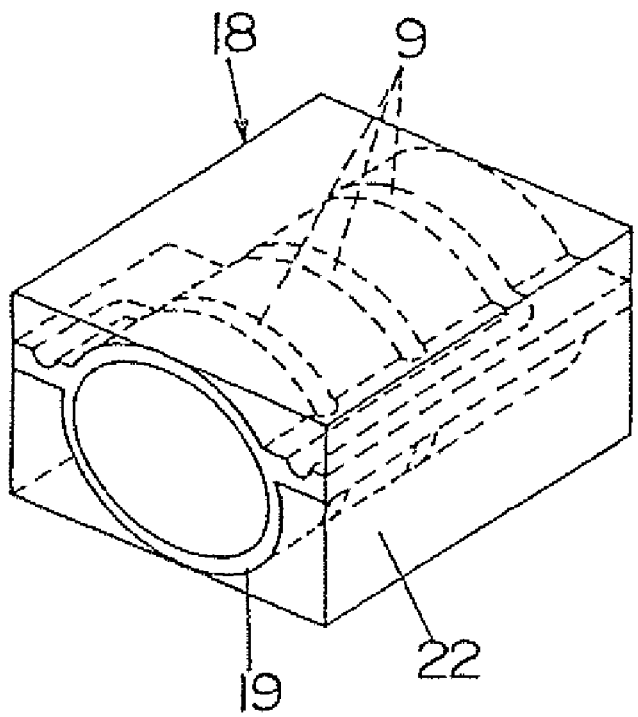
FIG. 34 is a perspective view of a primary winding in the same.

When an electrically conductive resin 21 which is highly flowable is poured into the groove 19a of the housing 19 installed in a set of molds 20 shown in FIG. 33, it easily runs from the groove 19a to the grooves 19b. As its resin 21 is completely cured, the primary winding 9 is shaped extending along the grooves 19a and 19b on the outer surface of the housing 19.

As the housing 19 with the primary winding 9 is entirely covered with a synthetic resin (a secondary insulating material, e.g. poly-ether-imide identical to the material of the housing 19) but its two lengthwise end openings remaining open, the primary winding assembly 18 containing the housing 19 covered with the secondary insulating material of a shape 22 is completed.

Finally, as the magnetic core 3 with the secondary winding 10 is installed in the housing 19 of the primary winding assembly 18 and the primary winding 9 is connected at both ends to terminal strips 23, the electromagnetic device (a transformer) of this embodiment is completed (See FIGS. 30 and 31). The primary winding assembly 18 is arranged extending substantially between the low-voltage end 10*a* of the secondary winding 10 and the lengthwise center of the magnetic core 3.

Because of the above arrangement of this embodiment, the insulation between the primary winding 9 and the secondary winding 10 can be implemented by the primary winding assembly 18. Since the secondary insulating material of the shape 22 encloses the housing 19 on which the primary winding 9 has been developed with the electrically conductive resin material 21, it can favorably insulate the primary winding 9 from the high-voltage end of the secondary winding 10. Also, as the primary winding 9 is fabricated by filling the grooves 19*a* and 19*b* of the housing 19 with the highly flowable electrically conductive resin material 21 with no need of the conventional step for winding a wire to develop the primary winding 91 its assembling process can be facilitated thus improving the overall productivity. As its dimensional properties remain free from unwanted variations which are pertinent to the coated wire and its winding exhibits a minimum of winding faults, the primary winding 9 can be small or thin. As a result, the electromagnetic device can hence be minimized in the overall size or thickness.

Figure 35:
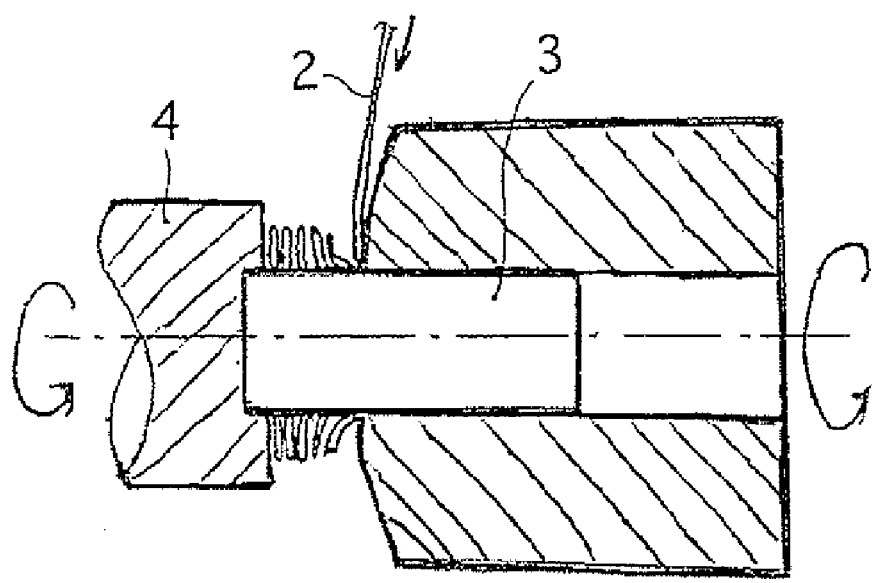
FIG. 35 is an explanatory view of the same.

While the magnetic cores 3 of this embodiment and the previous embodiments 1 to 14 are made of a bar-like ferrite material and polished at the surface, they may not be polished but remain rough. In the latter case, the surface roughness or mathematical average roughness (Ra) of the magnetic core 3 can preferably be 0.8 μm or greater. This eliminates the step of polishing the magnetic core 3 and can hence reduce the production cost of the magnetic core 3. In case that the surface roughness of the magnetic core 3 is declined, it may cause the flat rectangular wire conductor 2 to be slipped down and fractured during the edge-wise winding as shown in FIG. 35. When the magnetic core 3 remains rough at the surface, it can inhibit the flat rectangular wire conductor 2 from being fractured thus permitting ease of the edge-wise winding.

Embodiment 16

Figure 38:
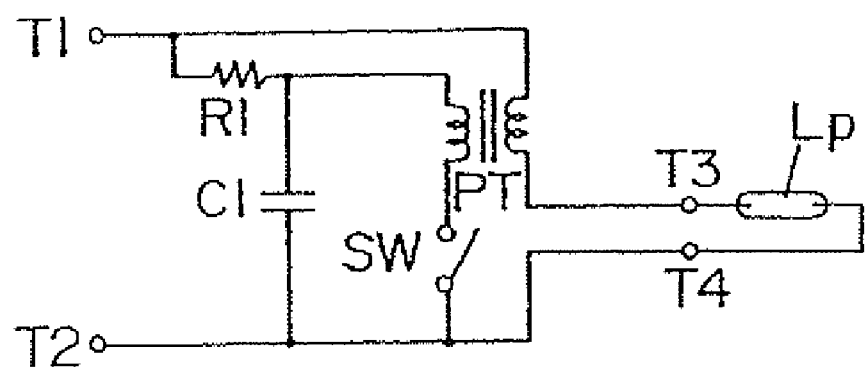
FIG. 38 is a schematic circuitry diagram showing a conventional high-voltage generating device.

Prior to the description of this embodiment, a circuitry arrangement in the conventional high-voltage generating device will be explained referring to FIG. 38. The conventional device acts as an igniter for supplying a high intensity discharge lamp Lp with a pulsed high voltage and comprises a pair of input ports T1 and T2 for receiving the high voltage, a pair of output ports T3 and T4 connected to the high intensity discharge lamp Lp, a pulse transformer PT of which the secondary winding is connected between the input port T1 and the output port T3 at the high voltage side and the primary winding is connected between the two input ports T1 and T2, a switching element SW connected between the low voltage side of the primary winding of the pulse transformer PT and the input port T2 at the lower voltage side, a resistor R1 connected between the input port T1 at the high voltage side and the high voltage side of the primary winding of the pulse transformer PT, and a capacitor C1 connected in parallel with both the primary winding of the pulse transformer PT and the switching element SW. In action of the conventional device, a voltage input received by the two inputs T1 and T2 while the high intensity discharge lamp Lp is not lighted is passed via the resistor R1 to the capacitor C1 which is thus charged. When the voltage at both ends of the capacitor C1 is increased to a given level, it turns the switching element SW on. This allows the power to be discharged from the capacitor C1 and transmitted via the switching element SW to the primary winding of the pulse transformer PT which then generates a pulsed high voltage at its secondary winding. The pulsed high voltage is then received by the high intensity discharge lamp Lp which in turn creates dielectric breakdown.

Figure 39:
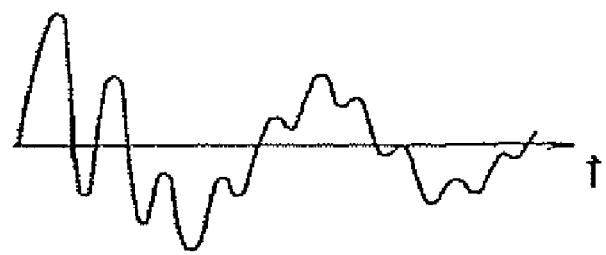
FIG. 39 is a waveform diagram showing an action of the conventional device.

FIG. 39 illustrates an exemplary waveform of the pulsed high voltage output of the conventional device where a high frequency component is superimposed on the waveform of a resonant voltage generated by the action of the capacitor C1 at the primary winding of the pulse transformer PT and boosted by the pulse transformer PT. This may result from the effect of any parasitic capacitance since the pulse transformer PT is not of an ideal form. It is however essential for allowing the high intensity discharge lamp Lp to start a dielectric breakdown promptly that the waveform of the pulsed high voltage is as close to its fundamental form as possible without the effect of the high frequency component. Also, when the voltage output of the conventional device is rapidly settled down to zero in the amplitude, its stressing effect on the components including the capacitor C1 can be minimized. As a result, the components of the circuitry arrangement to be employed can be eased in the resistance to high voltage and thus reduced in both the size and the price.

Figure 36:
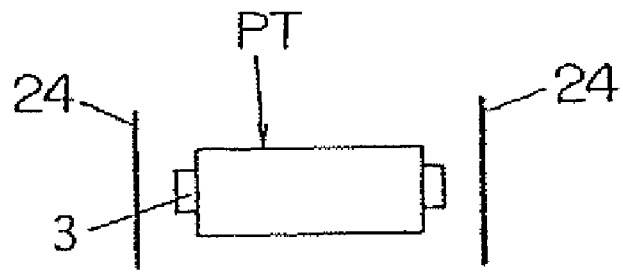
FIG. 36 is a plan view showing Embodiment 16 of the present invention.

The high-voltage generating device of this embodiment has a couple of metal strips 24 provided adjacent to both ends of the magnetic core 3 in a pulse transformer PT as shown in FIG. 36, thus minimizing the oscillation of the high frequency component. More specifically, the magnetic core 3 is magnetically open at both ends. When the magnetic flux leaked from the two ends of the magnetic core 3 and passed across the metal strips 24 is varied by the effect of the high frequency oscillation, it generates an eddy current on the metal strips 24. As a result, the eddy current loss will occur and offset the high frequency oscillation. The pulse transformer PT in this embodiment is implemented by the electromagnetic device (a transformer) of any of Embodiments 6 to 15.

Figure 37:
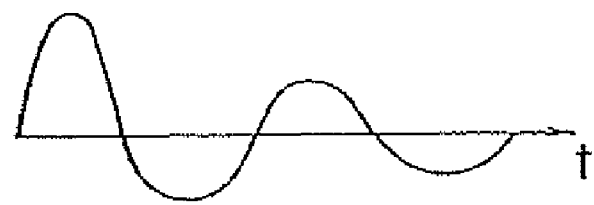
FIG. 37 is a waveform diagram illustrating an action of the same.

As described, the high voltage waveform supplied to the high intensity discharge lamp Lp can be corrected to close to the fundamental form shown in FIG. 37 with its high frequency component successfully offset by the eddy current loss created on the metal strips 24. Also, as the oscillation of the voltage output is rapidly reduced to zero, its stressing effect on the components including the capacitor C1 can be minimized. This allows the components to be used which are eased in the resistance to high voltage and thus decreased in both the size and the price. The metal strips 24 may be replaced by leads which are provided for electrically connecting between the components and located adjacent to both ends of the magnetic core 3 of the pulse transformer PT. As a result, the components to be used can be reduced in the total number and their arrangement can be simplified.

Embodiment 17

Figure 40:
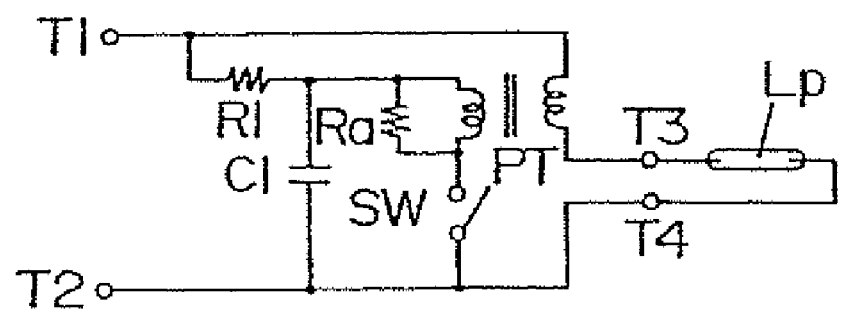
FIG. 40 is a schematic circuitry diagram showing Embodiment 17 of the present invention.
Figure 41:
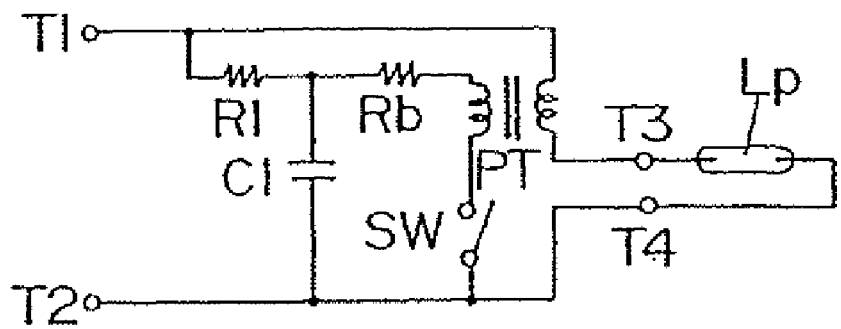
FIG. 41 is a schematic circuitry diagram of a modification of the same.

This embodiment is characterized by a high-voltage generating device where the primary winding of a pulse transformer PT is connected in parallel with a resistor Ra as shown in FIG. 40. The other arrangement is substantially identical to that of the conventional device shown in FIG. 38. The high frequency oscillation can thus be offset by the loss created in the resistor Ra which is connected in parallel with the primary winding. For providing the same effect, the primary winding of the pulse transformer PT may be connected in series with a resistor Rb as shown in FIG. 41.

Embodiment 18

Figure 42:
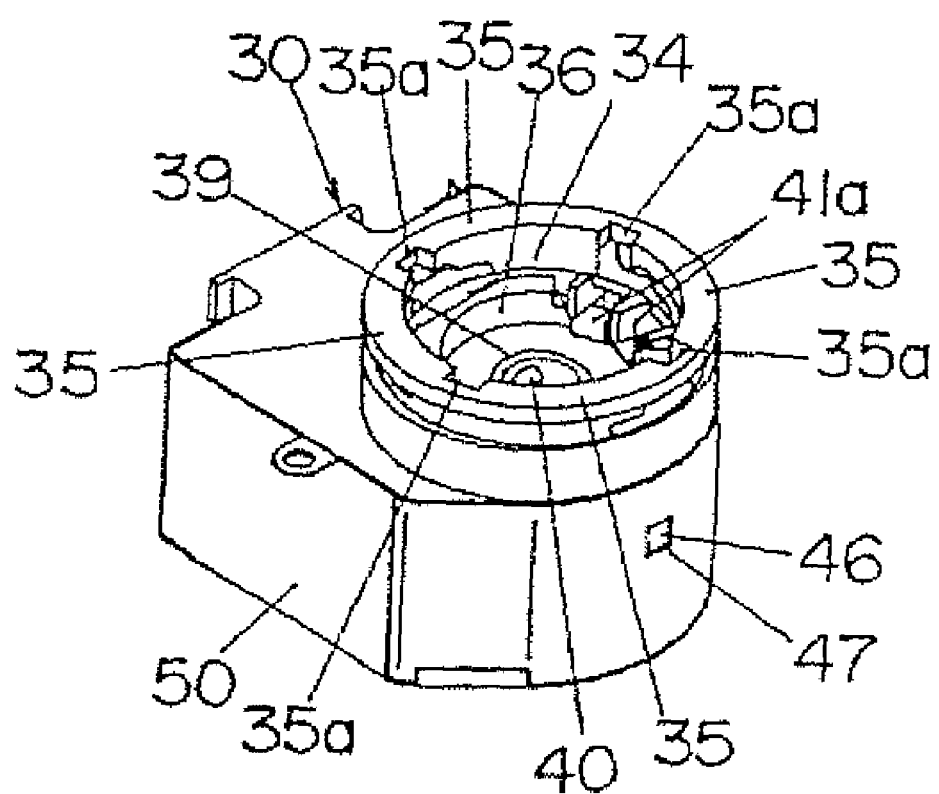
FIG. 42 is a perspective view showing Embodiment 18 of the present invention.
Figure 43:
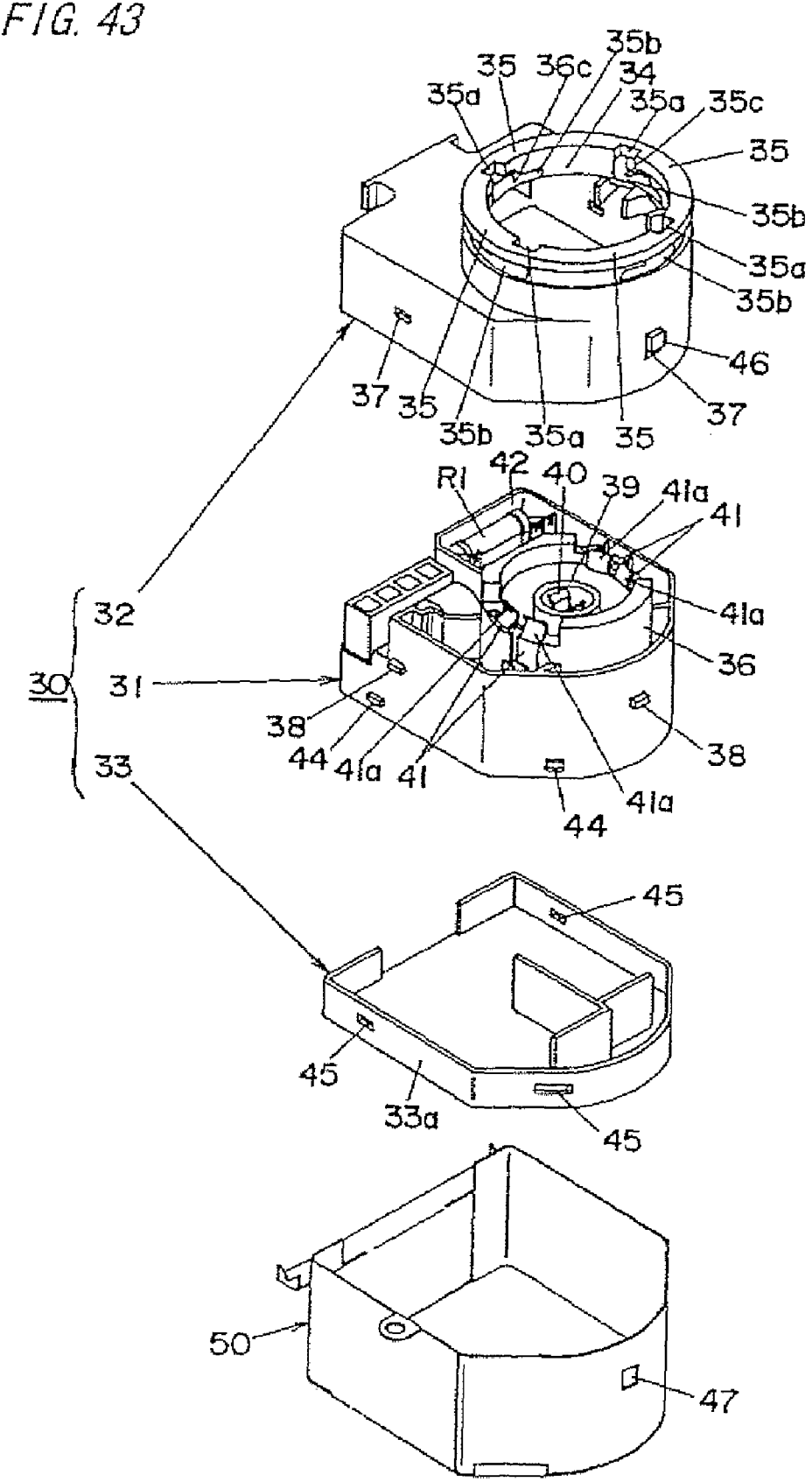
FIG. 43 is an exploded perspective view of the same.

This embodiment is characterized by a high-voltage generating device where a high intensity discharge lamp Lp is provided integral with a socket which is arranged detachable as shown in FIG. 42. The high-voltage generating device of this embodiment comprises a main assembly 30 made of a synthetic resin material and a shield cover 50 covering the back and lateral sides, but not the front side, of the main assembly 30 as best shown in FIG. 43. The main assembly 30 includes a body 31 containing major components including the pulse transformer PT described with Embodiment 16, a cover 32 covering the front side of the body 31, and a lid 33 closing the rear side of the body 31.

The cover 32 has a socket opening 34 of substantially a round shape provided in the front side thereof and a group of bayonet stoppers 35 provided on the circumferential edge about the socket opening thereof. The stoppers 35 are formed integral with the circumferential edge about the socket opening 34 and provided in the form of notches opening towards the center. More particularly, the stopper 35 is an L shaped recess comprising a vertical groove 35a for accepting each engaging tab (not shown) provided on the outer surface of a base of the high intensity discharge lamp Lp which is inserted from the front to the back in the socket opening 34 and a horizontal groove 35b continuously communicated with the vertical groove 35a. In addition, the stopper 35 has a stopper recess 35c provided in the innermost thereof for holding the engaging tab at the engaging position.

The body 31 includes a substantially cylindrical tube 36 accommodated in the socket opening 34 of the cover 32 and an engaging projections 38 provided thereon for engaging with engaging slots 37 provided in the lateral side of the cover 32. As the cover 32 is placed over the front side of the body 31, its engaging projections 38 come into engagement with the corresponding engaging slots 37. As a result, the body 31 and the cover 32 are joined together with its tube 36 accommodated in the socket opening 34 (See FIG. 42). The body 31 also has a center tube 39 of substantially a cylindrical shape provided upright in the center of the tube 36 and a center electrode 40 provided in the center tube 39 for direct contact with a center electrode (not shown) of the discharge lamp base. Also, a group of outer electrodes 41 are provided on the tube 36 for direct contact with corresponding outer electrodes (not shown) mounted on the outer side of the lamp base. When the body 31 and the cover 32 are joined together, contacts 41a of the outer electrodes 41 of its tube 36 come to face the inner side about the socket opening 34 of the cover 32. More particularly, when the lamp base is inserted into the socket opening 34 of the cover 32, its engaging tabs move into the vertical grooves 35a of the stoppers 35. As the lamp base is twisted, its engaging tabs move into the horizontal grooves 35b and finally come in direct engagement with the corresponding stopper recesses 35c. Simultaneously, the center electrode of the lamp base is inserted into the center tube 39 to come into direct contact with the center electrode 40. Also, the outer electrodes of the lamp base come into direct contact with the corresponding contacts 41a of the outer electrodes 41 about the socket opening 34 of the tube 36. As a result, the high intensity discharge lamp Lp is coupled to the high-voltage generating device of this embodiment electrically and mechanically.

Figure 44:
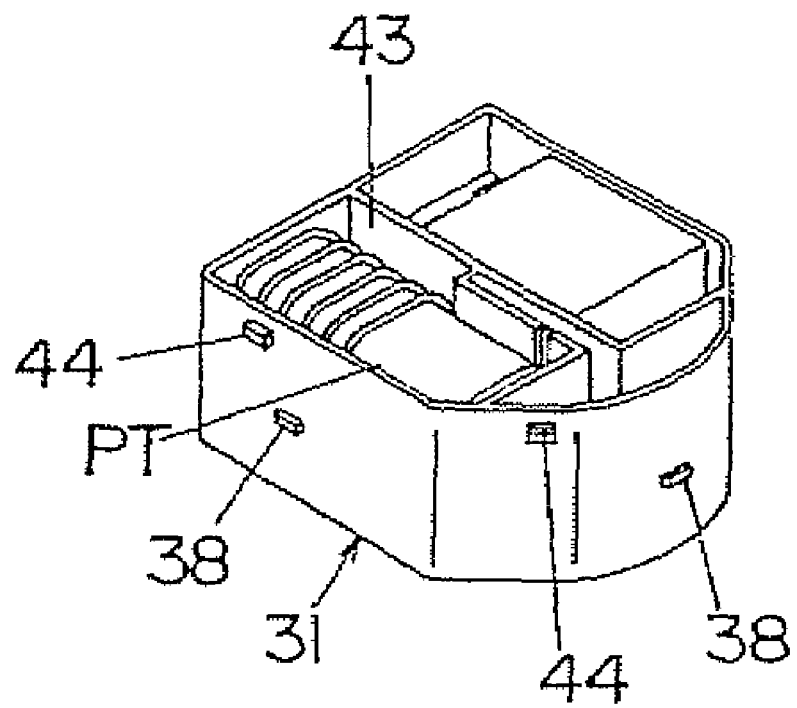
FIG. 44 is a perspective view seen from the back of a body of the same.
Figure 45:
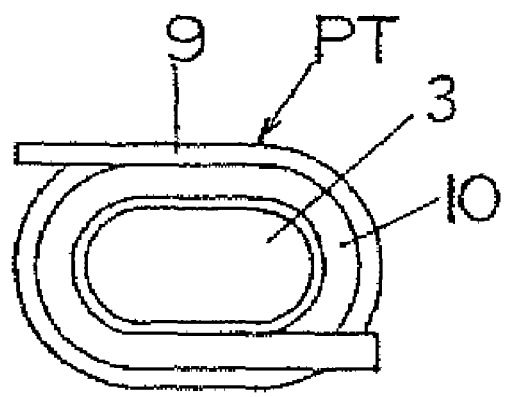
FIG. 45 is a side view of a pulse transformer in the same.

The body 31 also has a first component recess 42 provided in the front side thereof for accommodating the circuitry components including a resistor R1 and a capacitor C1. As best shown in FIG. 44, the body 31 has a transformer recess 43 provided in the back side thereof for accommodating a pulse transformer PT. The pulse transformer PT is identical in the construction to the electromagnetic device (a transformer) of Embodiment 9, having a flat rectangular wire conductor 2 wound in edge-wise winding form on a rod-like magnetic core 3 of substantially a cylindrical shape in the cross section to implement the secondary winding 10 and substantially six turns of a wire provided on the secondary winding 10 to implement the primary winding 9, as shown in FIG. 45.

The lid 33 has a group of engaging slots 45 provided in a circumferential wall 33a thereof for engagement with corresponding engaging projections 44 provided on the outer surface of the body 31. When the lid 33 is placed over the back side of the body 31, its engaging slots 45 come to accept the corresponding engaging projections 44. As the body 31 is coupled with the lid 33, it can be closed up at the back side with the lid 33.

The shield cover 50 is a box shape of an electrically conductive magnetic material having one side opened. The shield cover 50 has a fitting slot 47 provided in a circumferential wall thereof for engagement with a fitting projection 46 provided on the outer side of the cover 32. When the main assembly 30 consisting mainly of the body 31, the cover 32, and the lid 33 is inserted from the back into the shield cover 50, the fitting projection 46 of its cover 32 comes in engagement with the fitting slot 47 thus coupling the main assembly 30 with the shield cover 50.

As the pulse transformer PT in the main assembly 30 is accommodated in the body 31 with its magnetic core 3 facing at both ends the inner side of the shield cover 50, its magnetic core 3 of the main assembly 30 when coupled to the shield cover 50 develops a closed magnetic circuit together with the shield cover 50. Because the main assembly 30 is protected with the shield cover 50 and its pulse transformer PT allows the magnetic core 3 to develop the closed magnetic circuit together with the shield cover 50, any noise generated and emitted from the high-voltage generating device can favorably be attenuated and simultaneously the (high voltage) output of the pulse transformer PT can be increased. Also, the device itself can be minimized in the overall size or thickness. The shield cover 50 of this embodiment also acts as the metal strips 24 of Embodiment 16. As the metal strips 24 are not needed, the components can thus be decreased in the total number and their arrangement can be simplified.

Embodiment 19

Figure 46A:
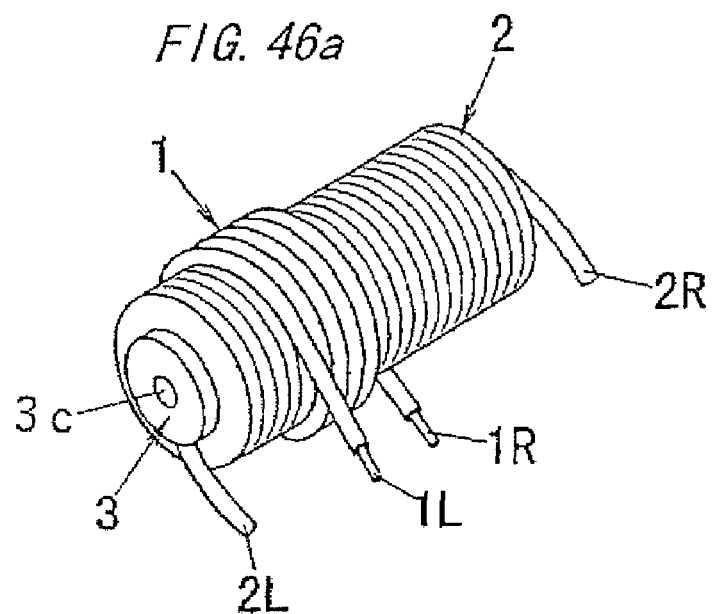
FIG. 46 is a schematic view of an electromagnetic device showing Embodiment 19 of the present invention.
Figure 46B:
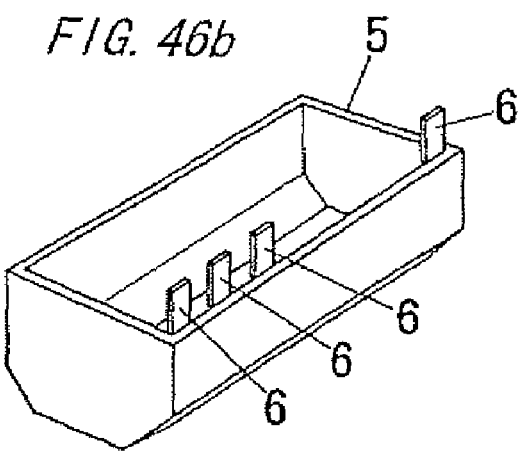
Figure 46C:
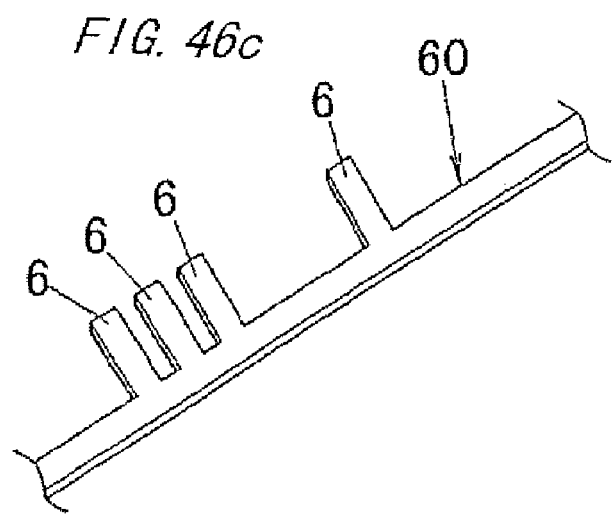
Figure 47:
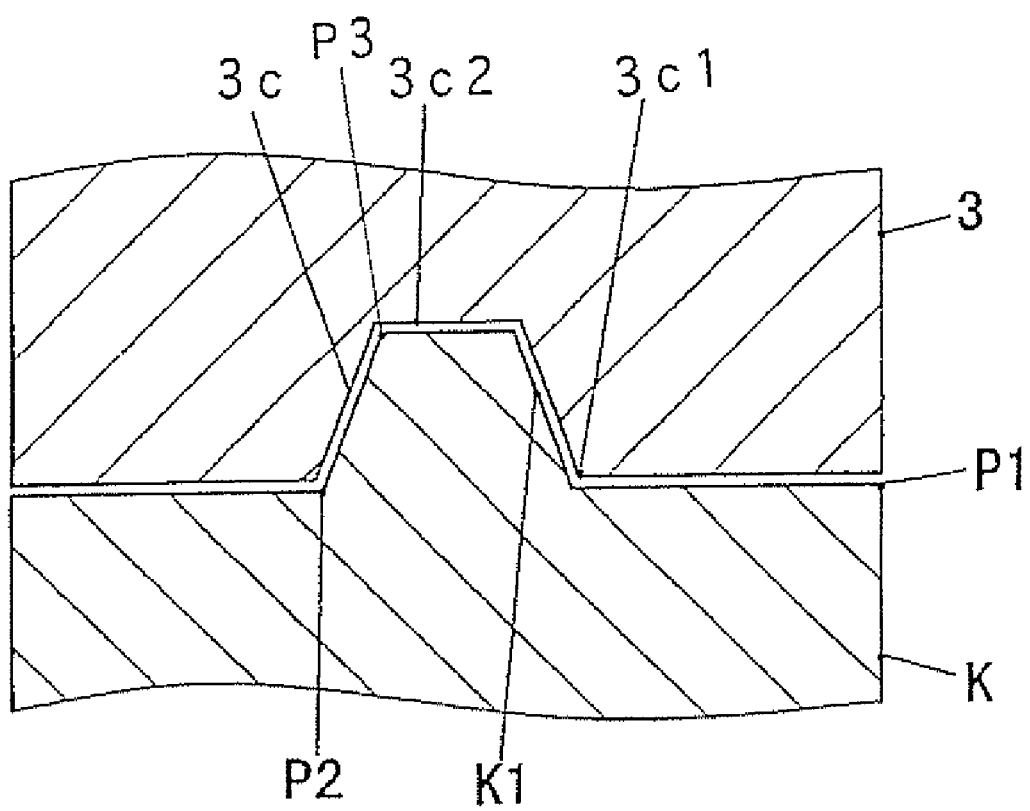
FIG. 47 is an explanatory view of the shape of recess provided in each end of a magnetic core showing Embodiment 20 of the present invention.

FIG. 46 is a construction view of an electromagnetic device of this embodiment and FIG. 47 is an explanatory cross sectional view showing the shape of a recess provided in the magnetic core 3 shown in FIG. 46. The electromagnetic device shown in FIG. 46 comprises the rod-like magnetic core 3 having an intrinsic resistance of not smaller than $10^3$ Ωm, a coil winding 2 provided on the magnetic core 3 by winding a flat rectangular wire in an edge-wise winding form with no use of a bobbin as the insulator, a coil winding 1 of an insulator coated wire (acting as the primary winding 9) provided directly over the coil winding 2, a resin casing 5 arranged for accommodating those components, and a group of terminals 6 extending outwardly from the casing 5 and connected to the coil windings.

As the coil windings 1 and 2 are provided directly on the magnetic core 3 with no use of the bobbin, the terminals 6 of this embodiment are joined with non of the bobbin. This embodiment allows the terminals 6 to be connected together by a hoop material 60 as shown in FIG. 46*c*. As apparent, the terminals 6 joined to the hoop material 60 are connected to the corresponding coil windings. Since the terminals 6 are drawn out in one direction as shown in FIG. 46*a*, the hoop material 60 can be arranged of a simpler shape. Even if the casing 5 is made by filling or molding of a resin material for giving the electrical insulation as shown in FIG. 46*b*, the terminals 6 are aligned in a row and they can thus be joined to the corresponding coil windings with much ease at the succeeding step.

Embodiment 20

Figure 70A:
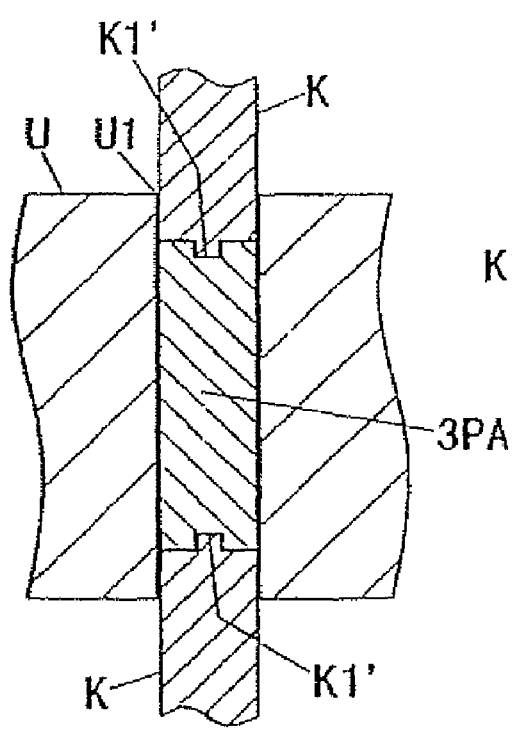
FIG. 70 is an explanatory view showing a process of fabricating a bar-like magnetic core having a bottomed hole provided in each end thereof.
Figure 70B:
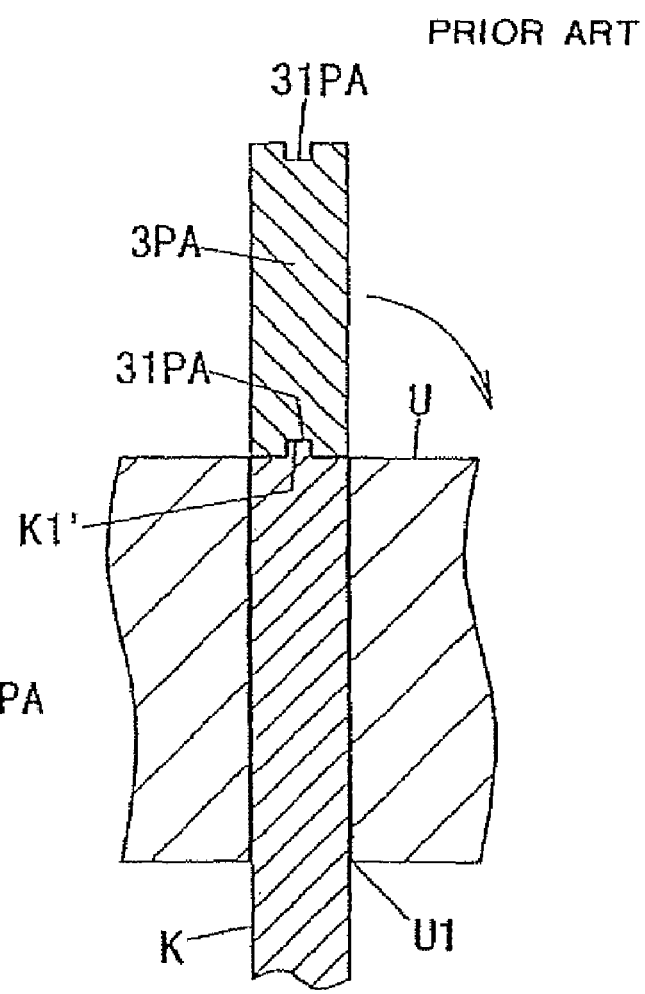
Figure 71:
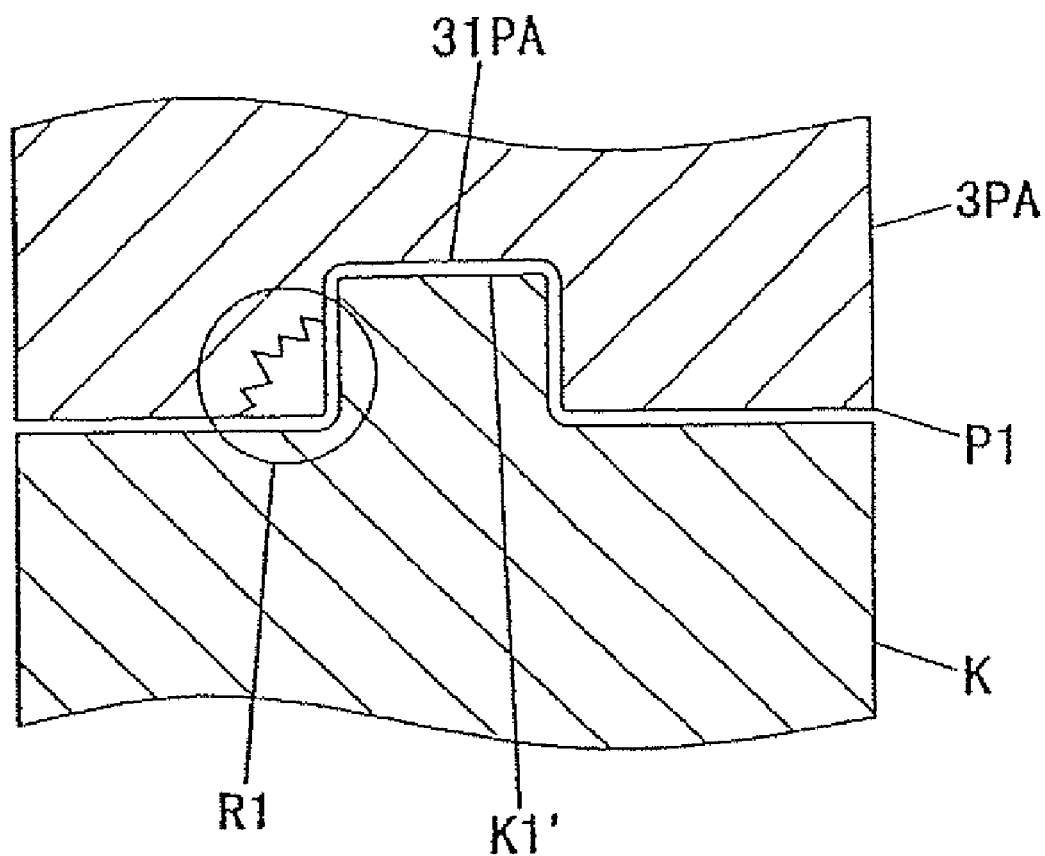
FIG. 71 is an explanatory view of the magnetic core shown in FIG. 69.
Figure 72A:
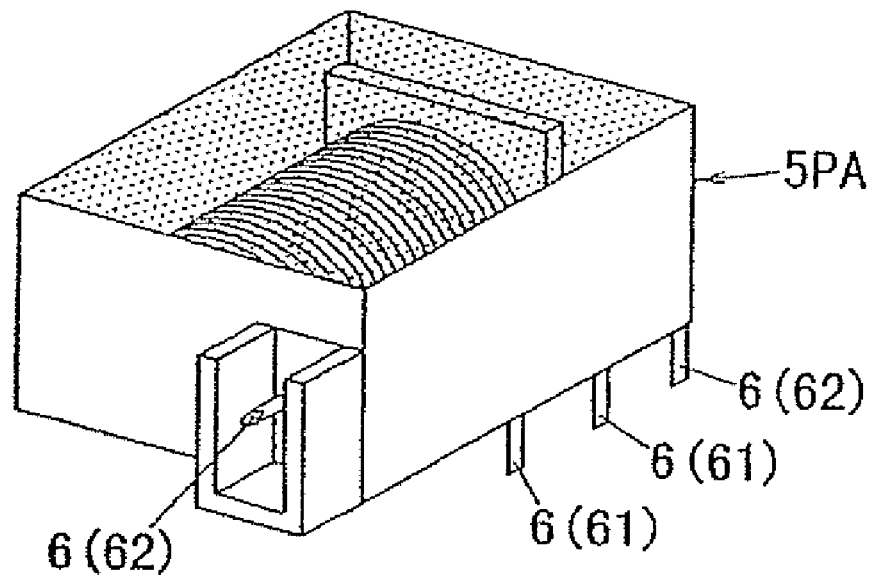
FIG. 72 is a perspective view of another conventional electromagnetic device.
Figure 72B:
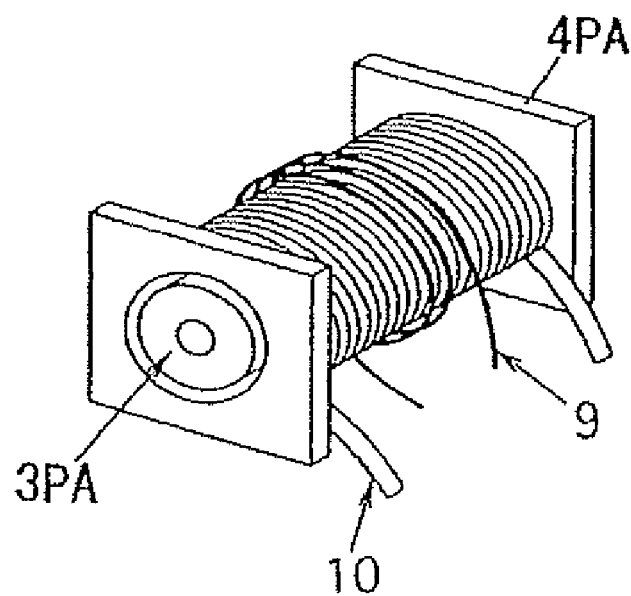
Figure 73:
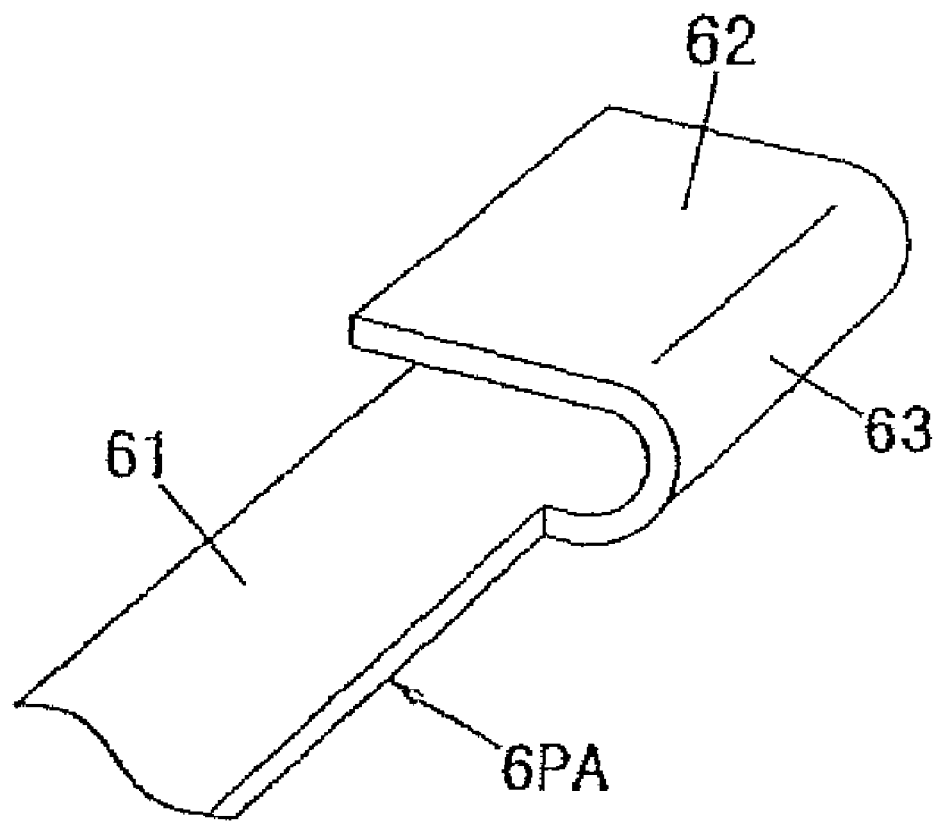
FIG. 73 is a perspective view of a conventional welding joiner welded to an insulation coated wire.

Referring to FIG. 47, this embodiment allows a magnetic core 3 to have a recess 3*c* provided in each end thereof defining a bottom 3*c*2. The recess 3*c* is arranged to have a tapered shape which becomes smaller in the diameter from an opening 3*c*1 to the bottom 3*c*2. In production, the magnetic core 3 is supported by not a rod jig shown in FIG. 70 but a rod K having a tapered projection K1. As the magnetic core 3 is removed and tilted down about the corner point P1 of the rod K, its bottom edge portion about the opening 3*c*1 of the recess 3*c* can successfully clear the projection K1 of the rod K where the radius of the movement of the edge portion P2 at the recess 3*c* of the magnetic core 3 about the point P1 is slightly greater than the distance from the projection point P3 of the edge of the projection K1 to the corner point P1 of the rod K. This inhibits any undesired tipping off at the edge about the recess 3*c* of the bottom of the magnetic core 3.

Embodiment 21

Figure 48A:
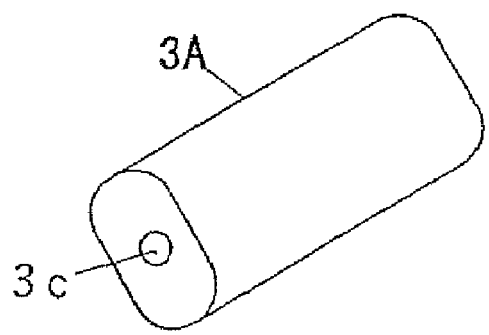
FIG. 48 is a view of a magnetic core in an electromagnetic device showing Embodiment 21 of the present invention.
Figure 48B:
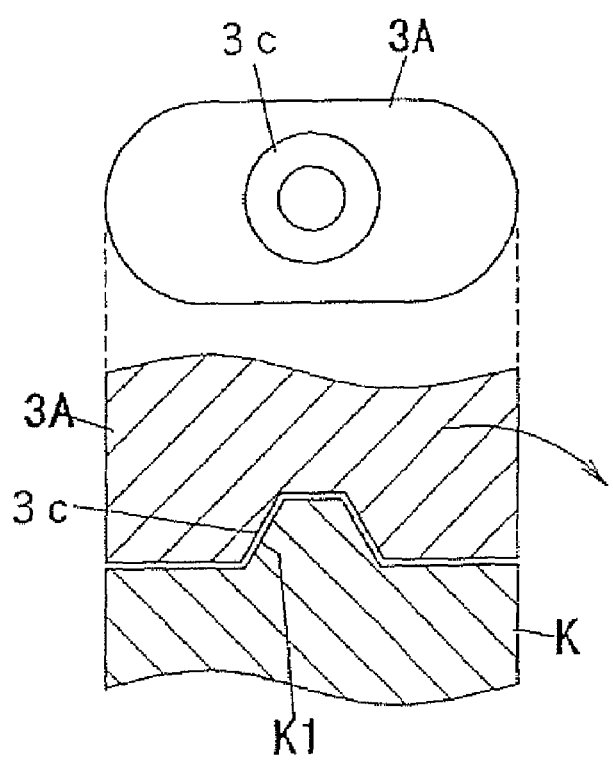
Figure 48C:
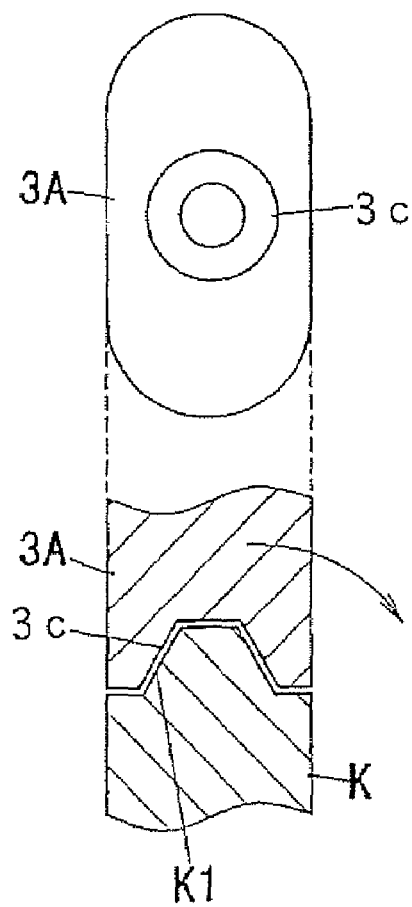

FIG. 48*a* illustrates the magnetic core of an electromagnetic device of this embodiment. The magnetic core 3A of the electromagnetic device has a recess 3*c* provided in each end thereof which is identical to that of the previous embodiment and is arranged of an elliptical shape in the cross section. The other arrangement is identical to that of the previous embodiment. As its magnetic core 3A is rather flat in the shape, the electromagnetic device can be implemented as a thin transformer. Also, the recess 3*c* has a tapered shape as described. As the magnetic core 3A is elliptical in the cross section, it may hardly be tilted down in a direction denoted by the arrow shown in FIG. 48*b* but easily fallen in another direction denoted by the arrow shown in FIG. 48*c*. It is hence understood that the tapered effect may be provided in the recess 3*c* only along the direction orthogonal to the lengthwise direction of the magnetic core 3A for inhibiting any undesired tipping off.

Embodiment 22

Figure 49:
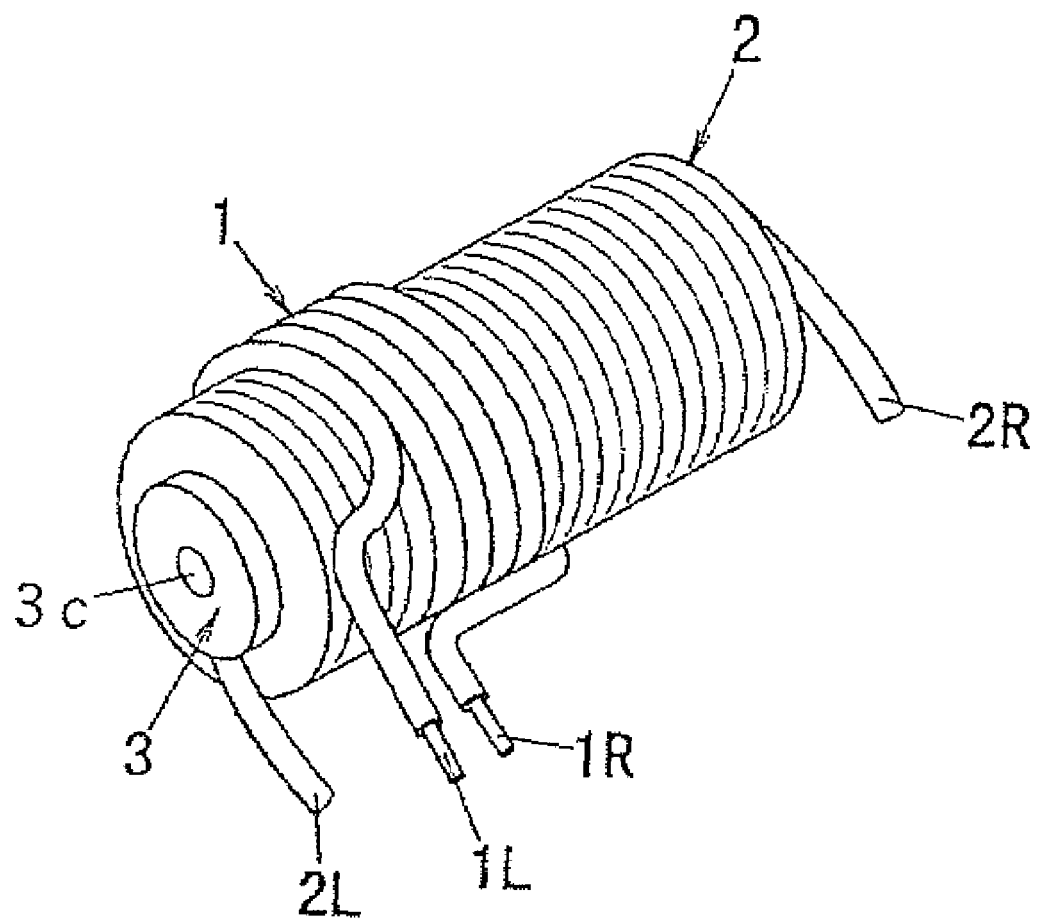
FIG. 49 is a view of a magnetic core and coil windings in an electromagnetic device showing Embodiment 22 of the present invention.

FIG. 49 illustrates an electromagnetic device of this embodiment having a magnet core and a group of coil windings. The electromagnetic device is differentiated from that of Embodiment 19 by the fact that the coil winding 1 wound on the coil winding 2 has two leads 1L and 1R thereof drawn out specifically. Assuming that the coil winding 1 acts as the primary winding and the coil winding 2 acts as the secondary winding, the coil winding 2 is fabricated by winding a flat rectangular wire of foil shape, which is high in the engaging rate, in an edge-wise winding form on the magnetic core 3. Accordingly, the coil winding 2 can be increased in the number of turns without decreasing the cross sectional size. The electromagnetic device is hence used as a small sized, high-voltage transformer which can easily produce a high voltage of, for example, several to tens kilovolts across its secondary winding 2 when the coil winding 1 is loaded as the primary winding with a voltage of hundreds bolts to a few kilovolts. In that case, the magnetic circuit of the coil windings 1 and 2 is an open circuit coaxial with the magnetic core 3.

It is known that the open circuit allows the coupling between the primary and secondary windings to be more increased when the coil winding 1 is located as the primary winding on the center of the magnetic core 3 than on either end of the same. The coil winding 1 shown in FIG. 46 is biased towards the center of the coil winding 2 and more particularly located leftwardly of the center of the coil winding 2 of which the right lead 2R acts as a high-voltage end. The location of the coil winding 1 leftwardly of the center of the coil winding 2 is based on the following reason. As shown in FIG. 46*a*, the potential between 2R and 1L(1R) is as high as several to tens kilovolts while the potential between 2L and 1L(1R) ranges from hundreds volts to a few kilovolts. Also, as the joint between the lead of each coil winding and the terminal 6 is implemented by an uncovered metal joint, it may trigger dielectric breakdown when a gap is generated between the resin material housing and the high-voltage transformer. For inhibiting any dielectric breakdown, the distance between 2R and 1L(1R) is enlarged.

When the coil winding 1 is located on the lead 2L of the coil winding 2, the protection from dielectric breakdown can be enhanced but the coupling between the primary and secondary windings will be declined thus lowering the level of the high-voltage output at the secondary winding. For compensation, the coil winding 1 of this embodiment is slightly biased towards the center of the coil winding 2 to guarantee the coupling between the primary and secondary windings as shown in FIG. 49 while its two leads 1L and 1R are biased towards the low-voltage end 2L of the coil winding 2. This allows the high-voltage transformer to be improved in the resistance to dielectric breakdown while ensuring the coupling between the primary and secondary windings.

Embodiment 23

Figure 50A:
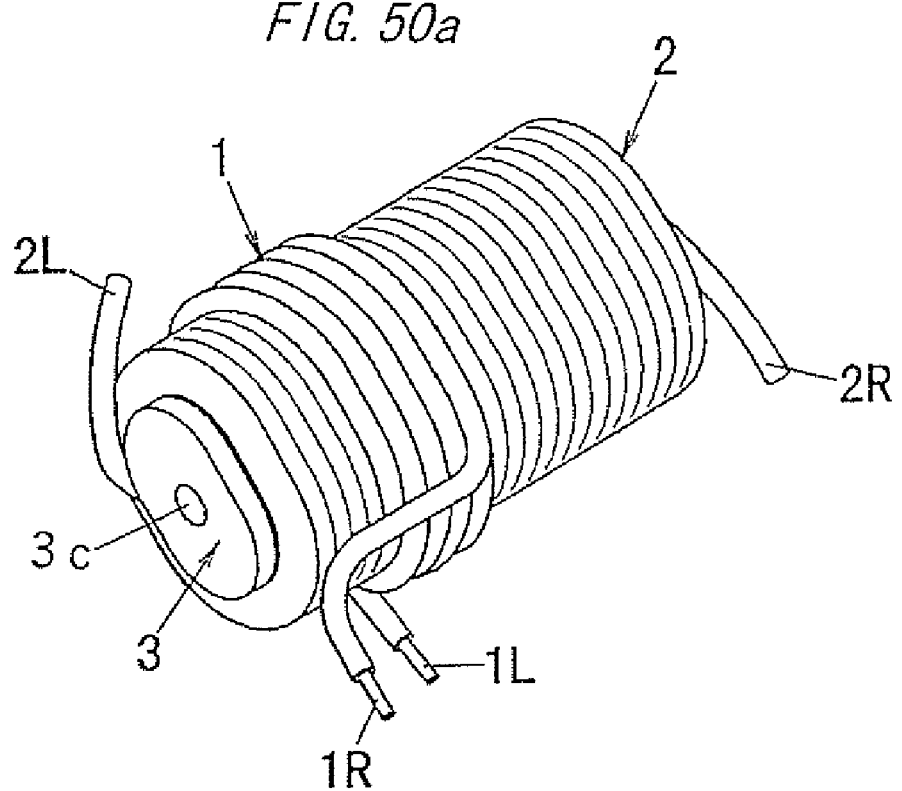
FIG. 50 is a view of a magnetic core, coil windings, and an insertion molded member in an electromagnetic device showing Embodiment 23 of the present invention.

FIG. 50 illustrates an electromagnetic device of this embodiment having a magnetic core, a group of coil windings, and an insertion molded member. The electromagnetic device is differentiated from the previous one by the fact that the casing 5 is replaced by an insertion molded member 5A for drawing the leads of the coil windings 1 and 2. As its magnetic core 3A has an elliptical shape in the cross section as shown in FIG. 50*a*, the electromagnetic device of this embodiment can be used as a thin transformer.

Figure 50B:
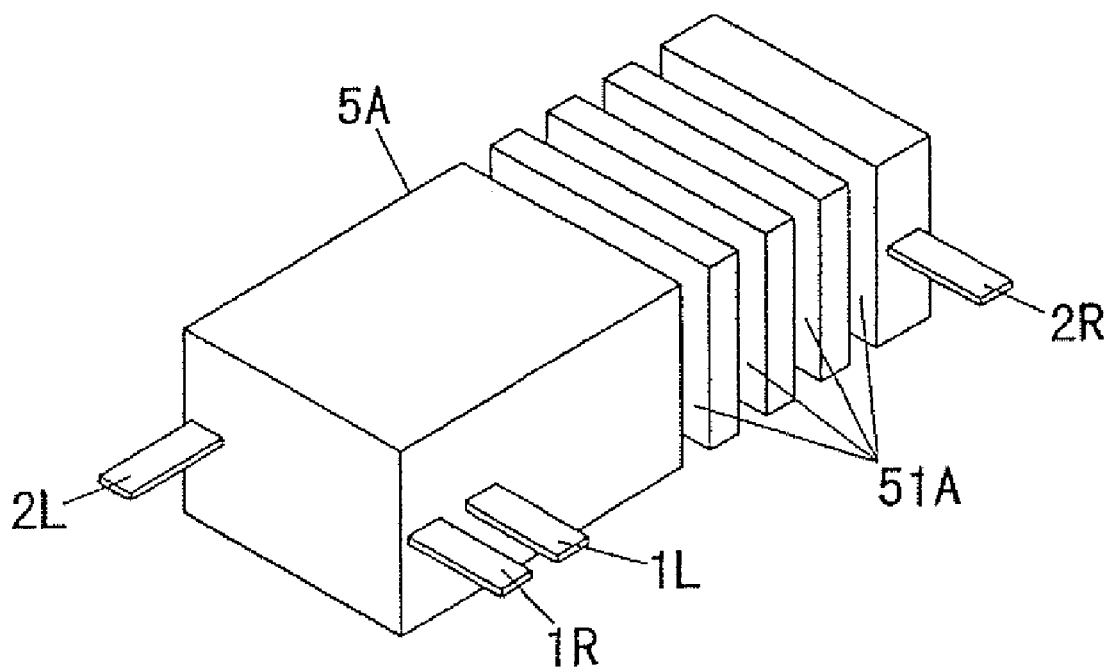

While the leads 1L and 1R of the coil winding 1 as the primary winding are drawn out from a location close to the low-voltage end 2L of the coil winding 2 in the previous embodiment, the lead 1R of the coil winding 1 of this embodiment close to the high-voltage end 2R of the coil winding 2 only is biased towards one particular end of the magnetic core 3A where the low-voltage end 2L of the coil winding 2 is located. This arrangement will also improve the insulation function. More particularly, the two leads of the coil winding 2 are drawn out along the thin side of the magnetic core 3A. This allows the insertion molded member 5A to remain minimum in the thickness as shown in FIG. 50*b*. Also, the two leads 2L and 2R of the coil winding 2 are located diagonal to each other so as to be distanced maximum from each other.

As shown in FIG. 50b, the insertion molded member 5A has a set of grooves 51A provided circumferentially in the outer sides thereof between the high-voltage end 2R and the other end 2L (1L and 1R). As the grooves 51A extend throughout the outer sides of the insertion molded member 5A to form a series of peaks and valleys on the surfaces. Accordingly, the surface (interface) distance between the high-voltage end 2R and the other end 2L (1L and 1R) on the insertion molded member 5A can be elongated. As a result, the insulation function between the one end 2R and the other end 2L (1L and 1R) can be improved thus allowing the small sized transformer to be easily fabricated having a higher level of the insulation.

Embodiment 24

Figure 51A:
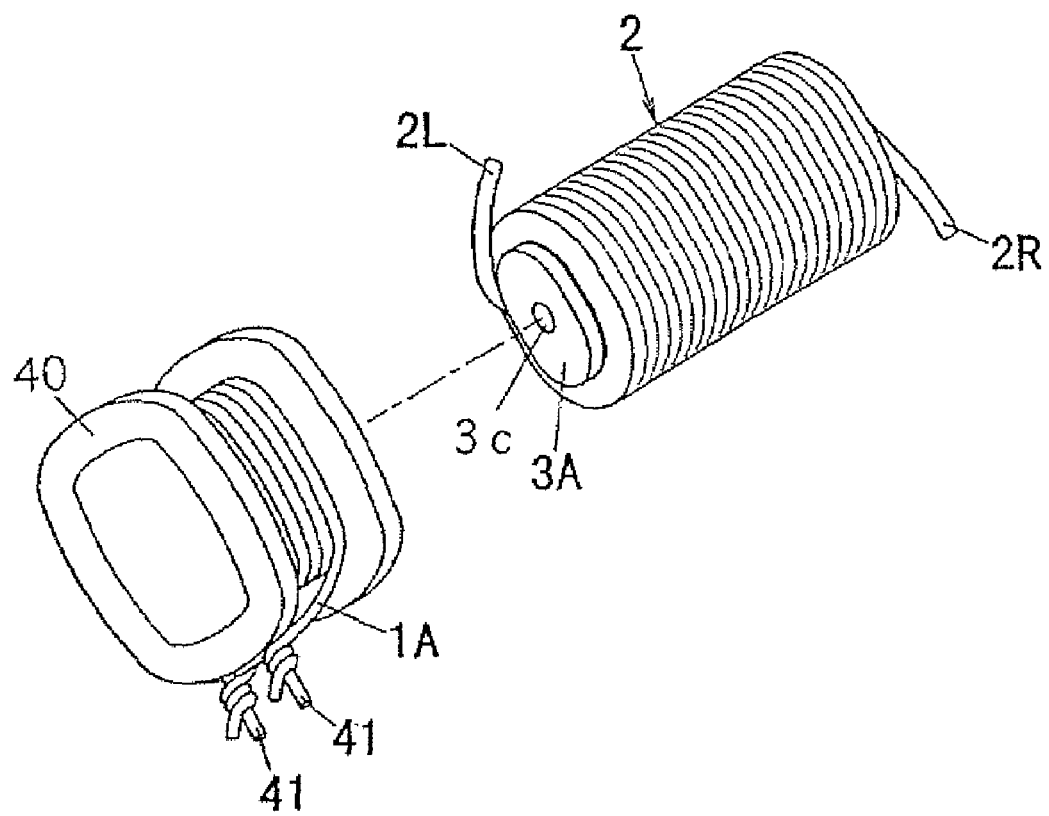
FIG. 51 is a view of a magnetic core, coil windings, and an insertion molded member in an electromagnetic device showing Embodiment 24 of the present invention.
Figure 51B:
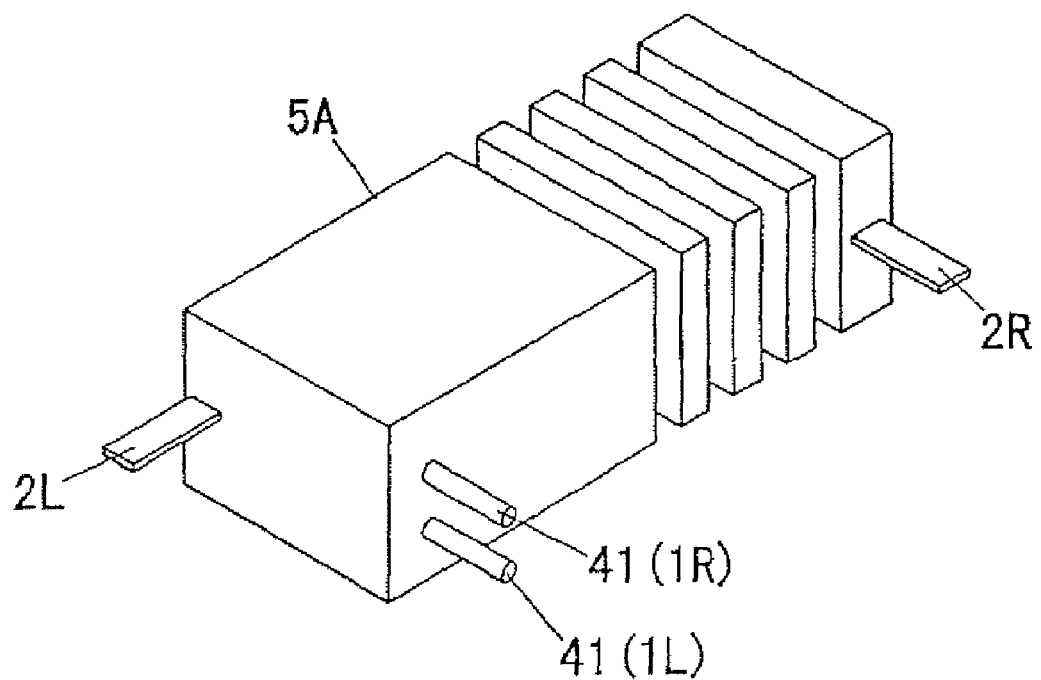

FIG. 51 illustrates an electromagnetic device of this embodiment having a magnetic core, a group of coil windings, and an insertion molded member. The electromagnetic device is similar to that of the previous embodiment, except that the insulation coated coil winding 1 is replaced by a coil winding 1A of a single wire with a bobbin 40 having a pair of terminals 41 and serving as the insulation coating, the coil winding 1A wrapped up at both ends with the paired terminals 41 of the bobbin 40. In this arrangement, while the bobbin 40 can increase the insulation function between the primary winding and the secondary winding, the connection between its paired terminals 41 and the coil winding 1A can be facilitated. The coil winding 1A is fabricated by the single wire of a low price, not the high-voltage insulation coated wire which is relatively high in the cost, thus contributing to the low price of a resultant high-voltage transformer.

Embodiment 25

Figure 52:
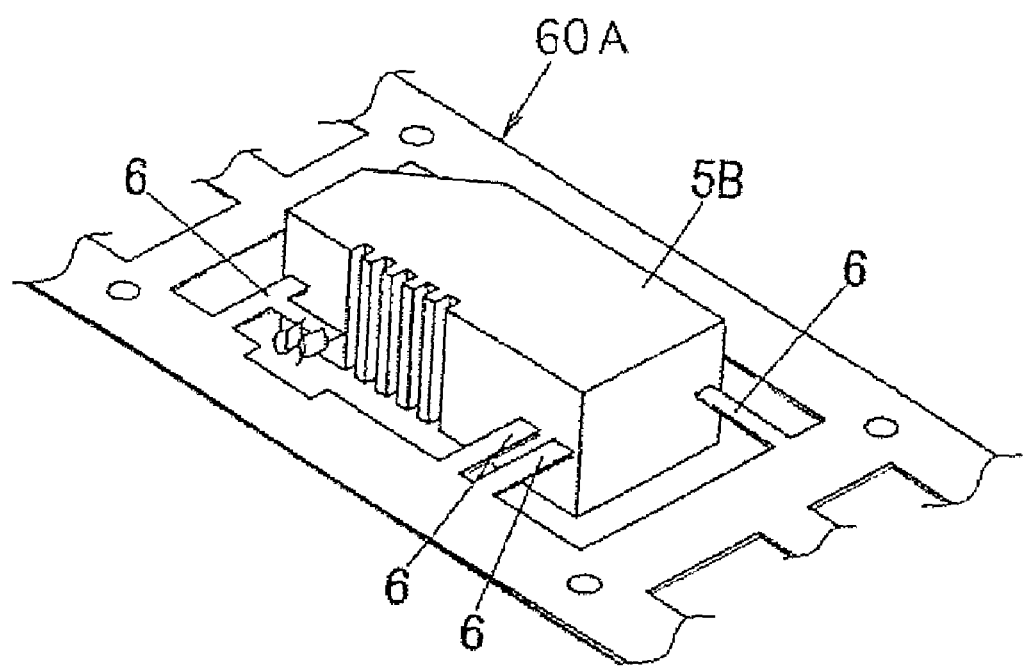
FIG. 52 is a schematic view of an electromagnetic device during its production showing Embodiment 25 of the present invention.
Figure 54:
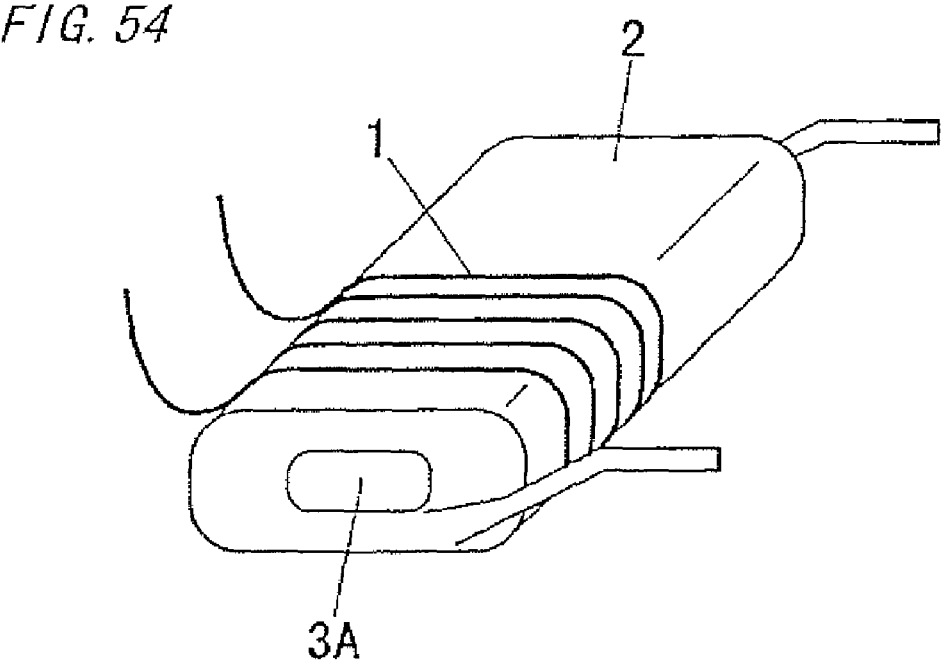
FIG. 54 is a view of a magnetic core and coil windings used for fabricating the electromagnetic device shown in FIG. 52.
Figure 55:
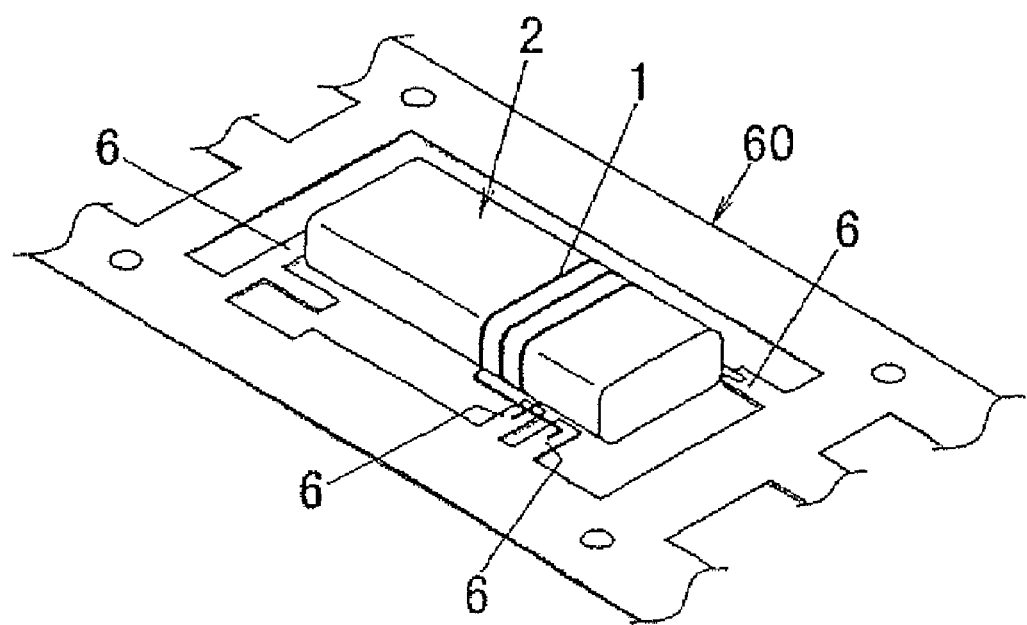
FIG. 55 is a schematic view of the electromagnetic device prior to that shown in FIG. 52.

FIG. 52 is a schematic view of an electromagnetic device of this embodiment at a step of its production. FIG. 53 is a plan view of the electromagnetic device shown in FIG. 52, FIG. 54 is a perspective view of a magnetic core and coil windings used in the electromagnetic device shown in FIG. 52, FIG. 55 is a schematic view of the electromagnetic device at a production step prior to the step of FIG. 52, and FIG. 56 is a plan view of the electromagnetic device shown in FIG. 55. The process of fabricating the electromagnetic device prior to the steps of FIGS. 52 and 53. As shown in FIG. 54, the coil windings 1 and 2 are provided on the magnetic core 3A of an elliptical shape in the cross section with no use of an insulator to develop a first intermediate product. More specifically, the coil winding 2 is fabricated by winding a flat rectangular wire in an edge-wise winding form on the outer side of the magnetic core 3A and then the coil winding 1 is provided on a predetermined location of the coil winding 2.

This is followed, as shown in FIGS. 55 and 56, by connecting ends of the coil windings 1 and 2 of the first intermediate product to corresponding terminals 6 of a lead frame 60A made of a single metallic strip to develop a second intermediate product. The second intermediate product is then placed in a set of unshown molds which are in turn filled with a thermoset resin material such as unsaturated polyester (by injection molding). As a result, a third intermediate product is given having the lead frame 60A joined with an insertion molded member 5B as shown in FIGS. 52 and 53. The above injection molding process can reduce the conventional vacuum filling process, which takes four or more hours, to as short as two minutes. Also, as the electromagnetic device employs a case-less arrangement, its overall dimensions can significantly be decreased.

Embodiment 26

Figure 59A:
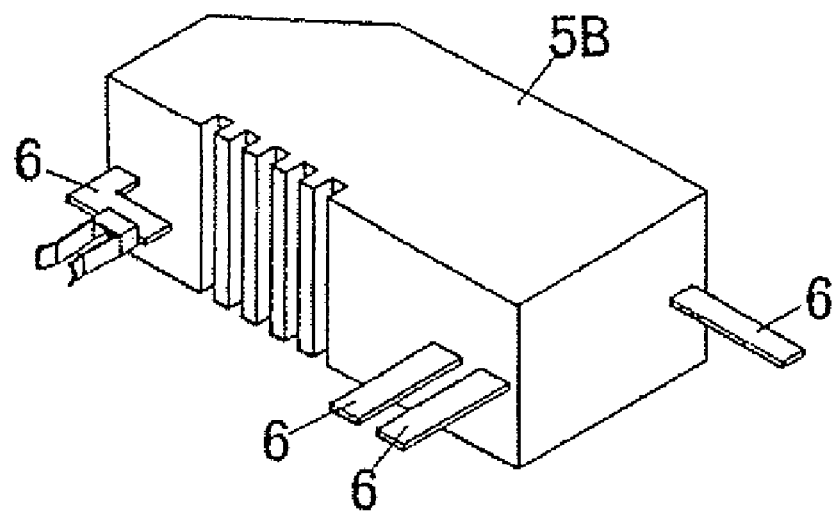
FIG. 59 is an explanatory view showing a process of fabricating the electromagnetic device shown in FIG. 58 from its previous form.
Figure 59B:
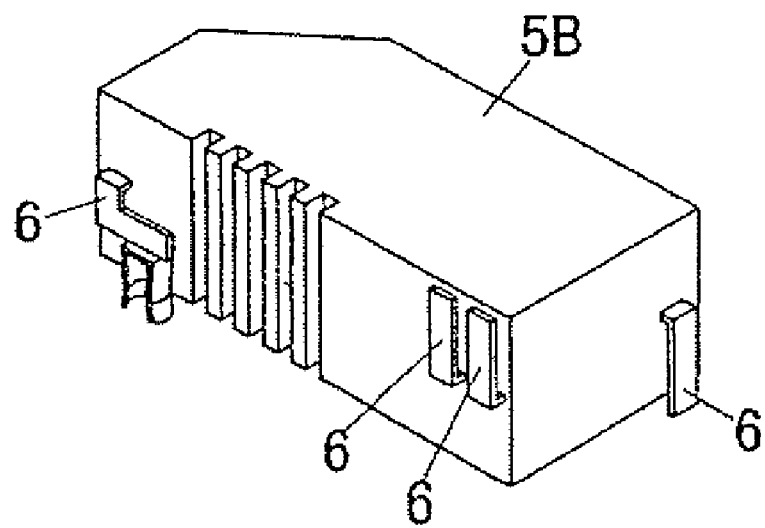

FIG. 57 illustrates a perspective view and a partially cross sectional view of an electromagnetic device of this embodiment. FIG. 58 is a plan view of the electromagnetic device shown in FIG. 57 and FIG. 59 is an explanatory view showing steps of shifting the electromagnetic device from an intermediate form to a finished form shown in FIG. 58. Particularly in this embodiment, the third intermediate product of the previous embodiment is provided with the coil windings 1 and 2 connected at their ends to corresponding terminals 6 of the lead frame 60A and then, the redundancy of the lead frame 60A is removed off for electrical isolation from the ends of the coil windings 1 and 2. As a result, a fourth intermediate product shown in FIG. 59a is given. Then, the terminals 6 are folded down in their respective directions (for a desired pattern) as shown in FIG. 5b, completing the electromagnetic device of this embodiment shown in FIGS. 57 and 58.

Figure 57A:
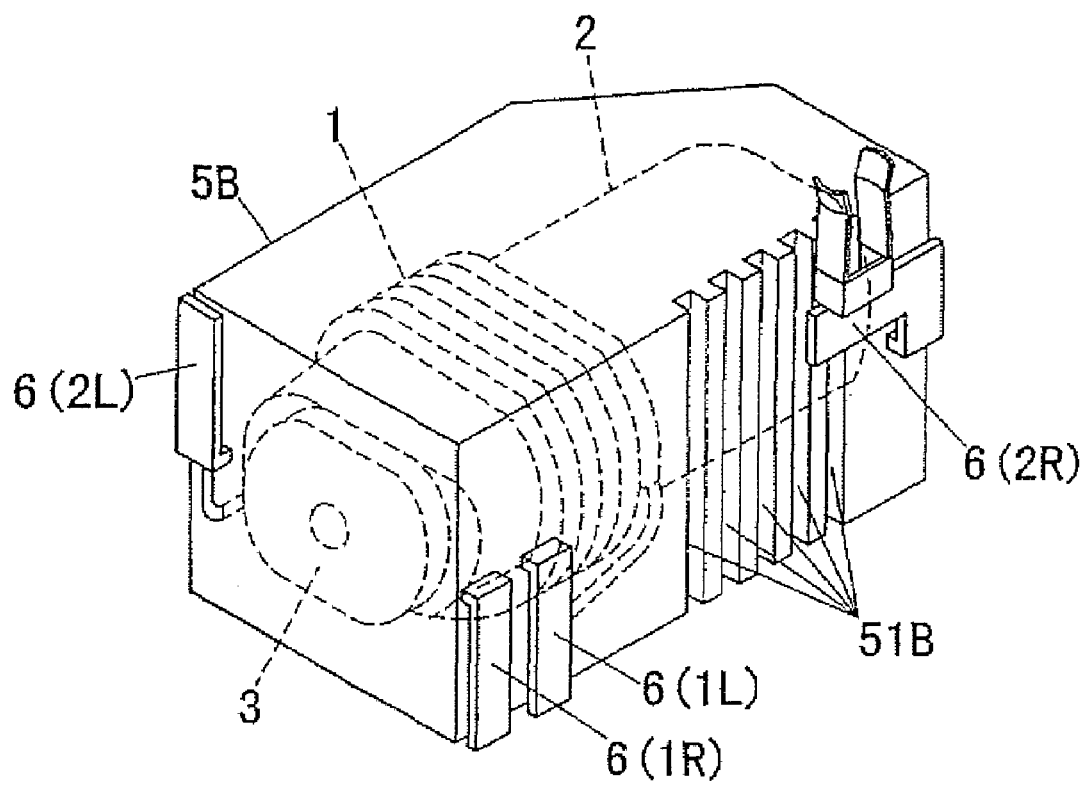
FIG. 57 illustrates a perspective view and a partial cross sectional view of an electromagnetic device showing Embodiment 26 of the present invention.
Figure 57B:
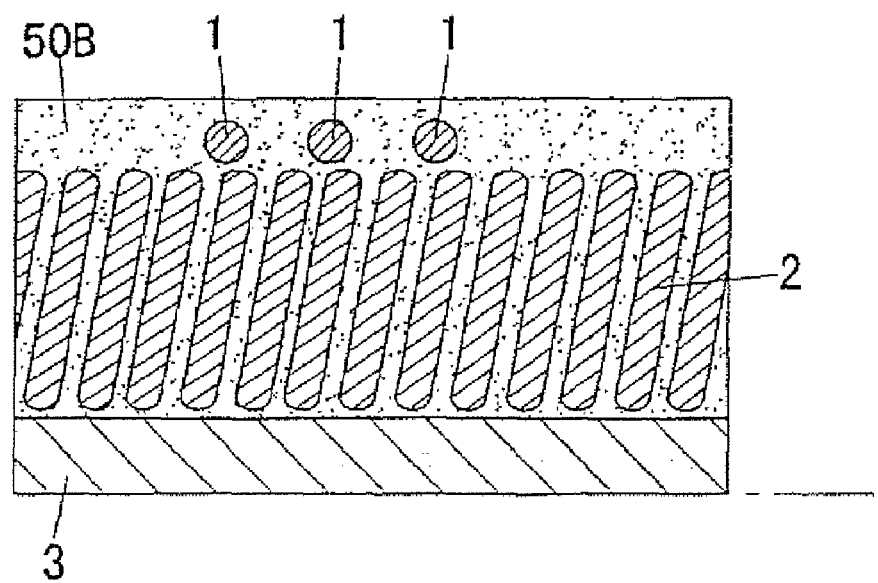
Figure 60:
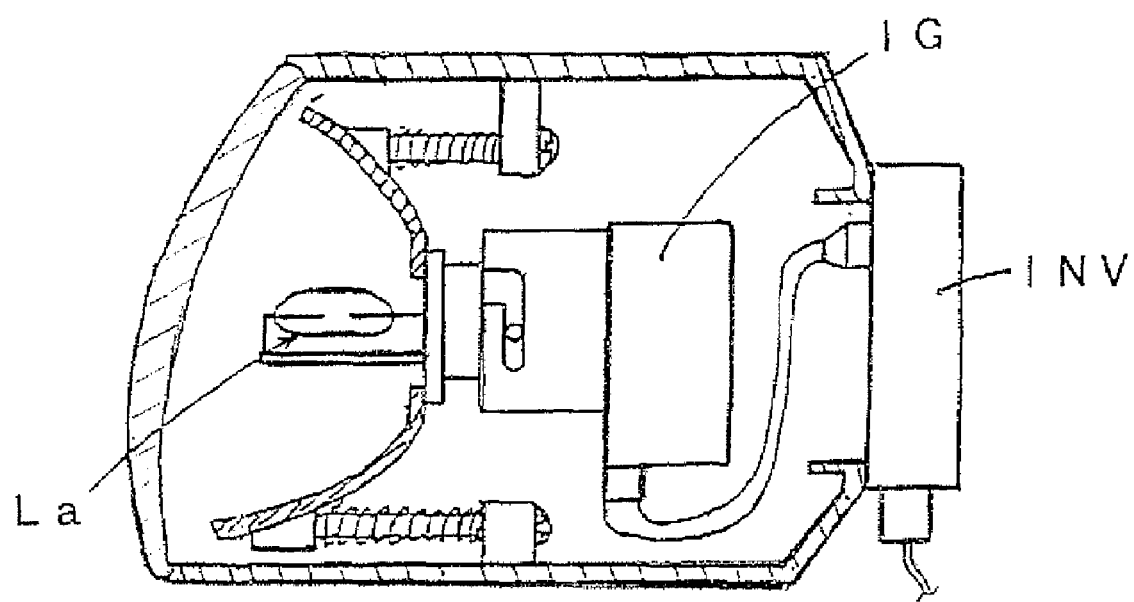
FIG. 60 is a view showing a discharge lamp igniter employing the electromagnetic device.
Figure 61:
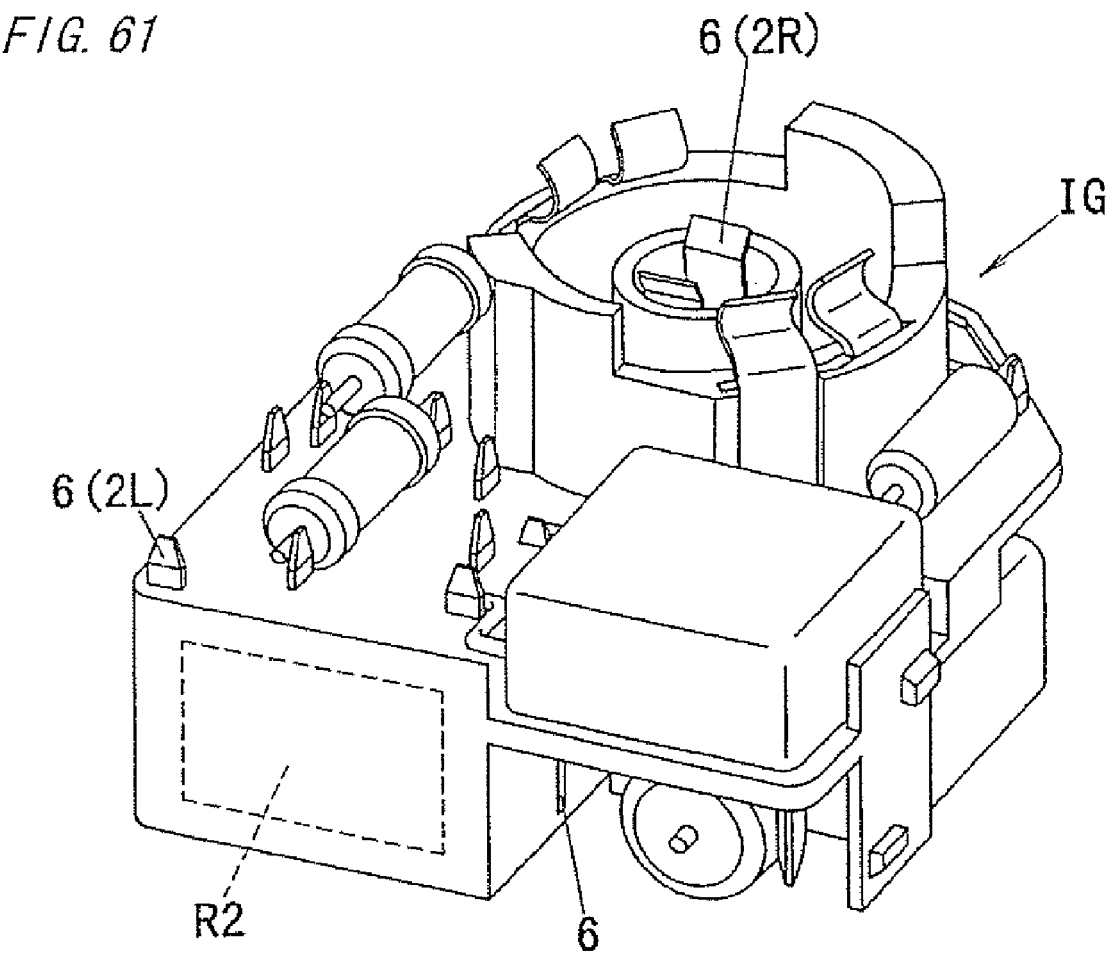
FIG. 61 is a view showing an igniter circuit provided in the discharge lamp igniter shown in FIG. 60.

As shown in FIG. 57a, there are a group of grooves 51B provided between the terminal 6 (2R) and the other terminals 6 (1L, 1R) in one side of the insertion molded member 5B, the terminal 6 (2R) connected with the high-voltage end 2R of the coil winding 2 and the terminals 6 (1L, 1R) connected with the two ends 1L and 1R of the coil winding 1. As the insertion molded member 5B has a series of peaks and valleys on the surface, its surface distance is between the two ends thus improving the insulation function and inhibiting any current leakage. The grooves 51B are of no limitations and may be replaced by a row of projections. Denoted by 50B in FIG. 57b is a filling material of the insertion molded member 5B. The electromagnetic device of this embodiment fabricated by the above manner is preferably used in a discharge lamp igniter which supplies a discharge lamp La as the headlight of vehicle with power and holds it at its lighting condition as shown in FIG. 60. The discharge lamp igniter includes a starter (igniter) circuit IG for feeding the discharge lamp La with a pulsed high voltage for illumination, as shown in FIG. 61. The igniter circuit IG is driven by an inverter INV. The electromagnetic device is installed at a region R2 in the igniter circuit IG denoted by the dotted line in FIG. 61 and its insertion molded member 5B made of a thermoset resin material is also protected with an enclosure of thermoplastic resin material (to form a double insulation). The electromagnetic device with its terminals 6 exposed to the outside is covered with the thermoplastic resin enclosure. Because of the double insulation, the electromagnetic device is almost thoroughly protected by the thermoplastic resin except its terminals and can thus be improved in the insulation distance and the moisture-proof function. Also, the grooves 51B extending from one end to the other end of one side of the insertion molded member 5B can serve as passages for positively distributing flows of the thermoplastic resin material during the molding process, hence promoting the flowability of the thermoplastic resin material in molten form.

Embodiment 27

Figure 62:
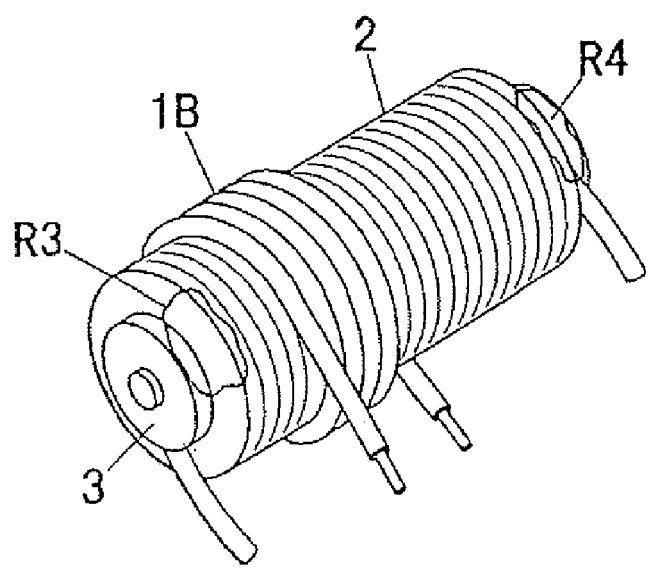
FIG. 62 is a view of a magnetic core and coil windings in an electromagnetic device showing Embodiment 27 of the present invention.

FIG. 62 illustrates an electromagnetic device of this embodiment having a magnetic core and a group of coil windings. The electromagnetic device is modified in which the coil winding 1 of an insulation coated wire is replaced by a fusible coil winding 1B. The process of fabrication starts with winding a flat rectangular wire in an edge-wise winding form on the outer surface of the magnetic core 3 to develop the coil winding 2. Then, an UV curable adhesive is applied to two regions R3 and R4 and cured by irradiation of UV light.

This is followed by winding a fusible wire on a predetermined region of the coil winding 2 to develop the coil winding 1B and energizing and fusing the coil winding 1B for bonding with the coil winding 2. As understood, the process can easily be carried out. Also, as its two ends are bonded by the adhesive to the side of the magnetic core 3, the coil winding 2 can hardly be detached by its spring-back effect.

Embodiment 28

Figure 63:
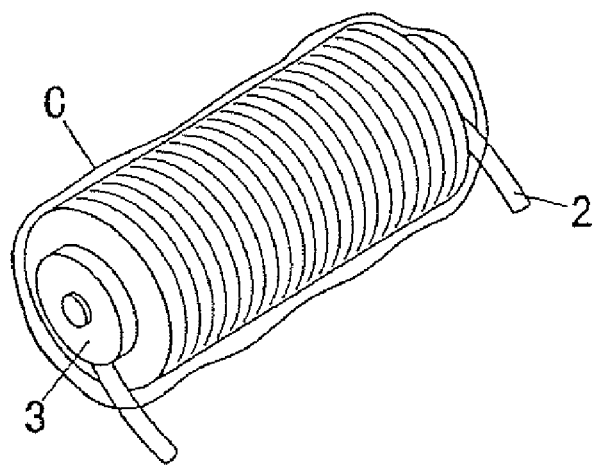
FIG. 63 is a view of a magnetic core and coil windings in an electromagnetic device showing Embodiment 28 of the present invention.

FIG. 63 illustrates an electromagnetic device of this embodiment having a magnetic core and a coil winding. The electromagnetic device is substantially identical in the construction to that of Embodiment 1 except that the coil winding 2 excluding its two ends is almost entirely covered with a thin coating C. When the magnetic core 3 is decreased in the diameter for downsizing, the coil winding 2 provided in an edge-wise winding form on the magnetic core 3 becomes smaller in the curvature radius and its coating may easily be torn off thus causing short-circuit between two adjacent turns of the coil winding 2. In this embodiment, after provided in an edge-wise winding form on the magnetic core 3, the coil winding 2 is protected with the thin coating C. This can inhibit unwanted short-circuit between any two turns of the coil winding 2.

Embodiment 29

Figure 64A:
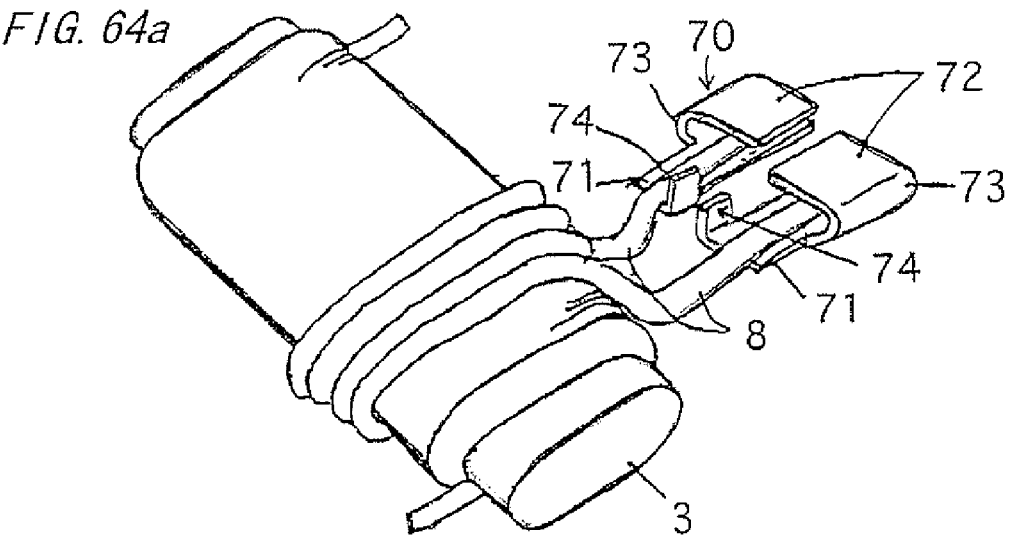
FIG. 64 is a view of a welding joiner showing Embodiment 29 of the present invention.

FIG. 64a illustrates an electromagnetic device of this embodiment having welding joiners 70. The welding joiner 70 is joined to one end of an insulation coated wire 8 of the primary winding and used as a terminal 6 of the electromagnetic device. The welding joiner 70 is arranged of a foldable shape comprising a flat base portion 71 extending in one direction, a folded portion 72 extending from one side at a right angle to the one direction, and an extending portion 73 allowing the folded portion 72 to face the flat portion 71. Also, a tab-like portion is provided extending from the other side than the folded portion 72 side of the base portion 71 and bent upwardly, thus acting as a positional error inhibitor 74. The length of the positional error inhibitor portion 74 from the flat portion 71 is equal or slightly greater than the diameter of the insulation coated wire 8. Particularly, the positional error inhibitor portion 74 is located as spaced from the folded portion 72.

Figure 64B:
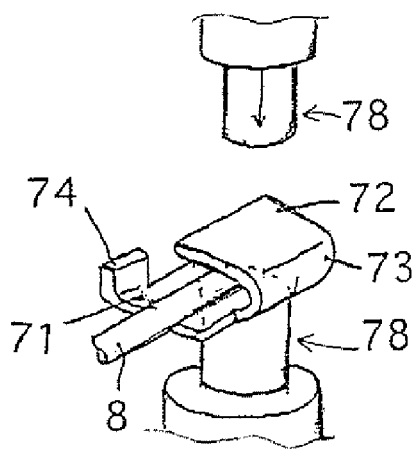
Figure 65:
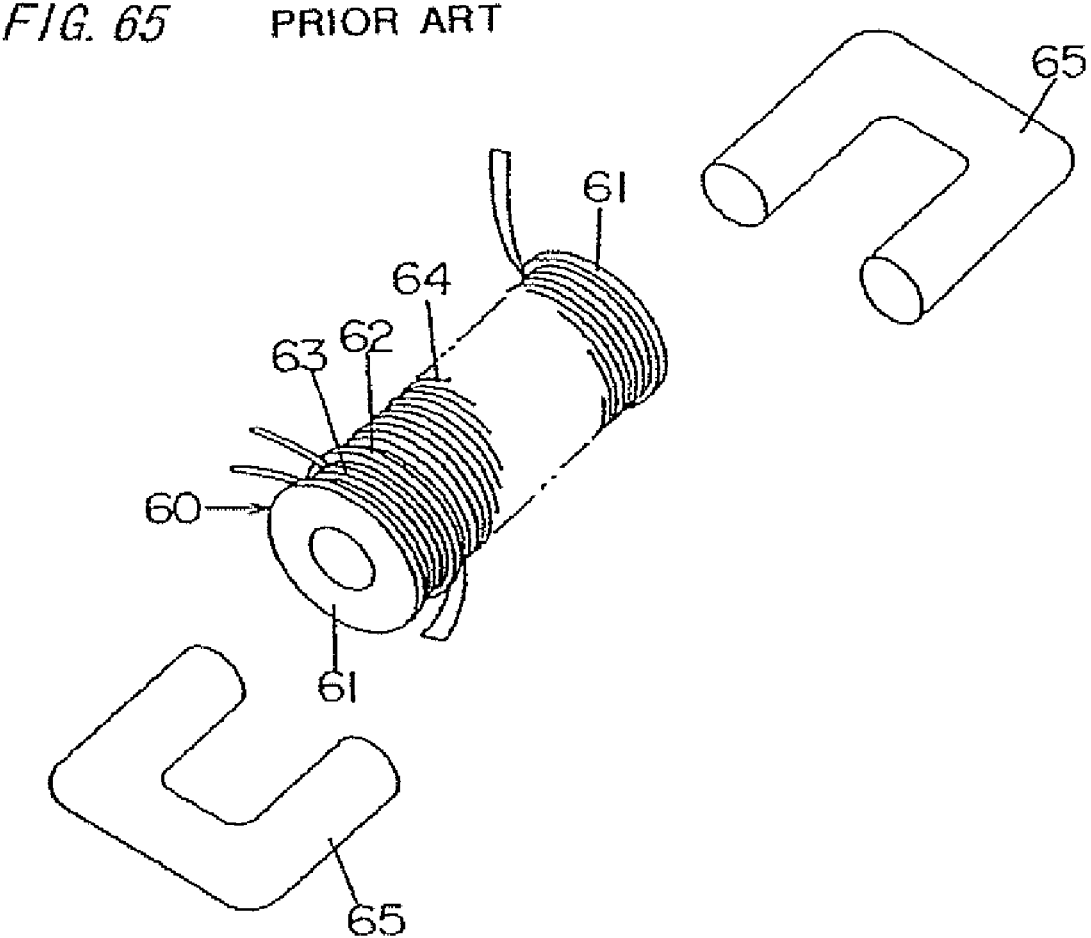
FIG. 65 is an exploded perspective view of a prior art.
Figure 66:
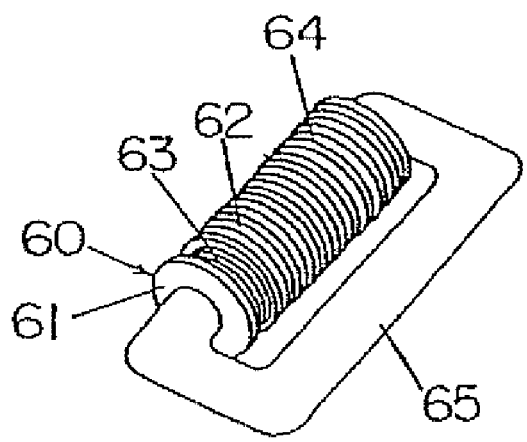
FIG. 66 is a perspective view of the same.
Figure 67:
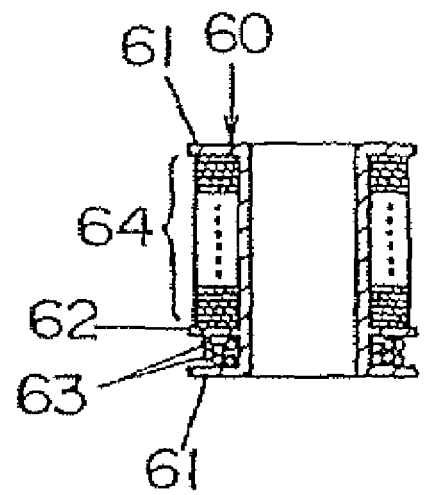
FIG. 67 is a cross sectional view of the same.
Figure 68:
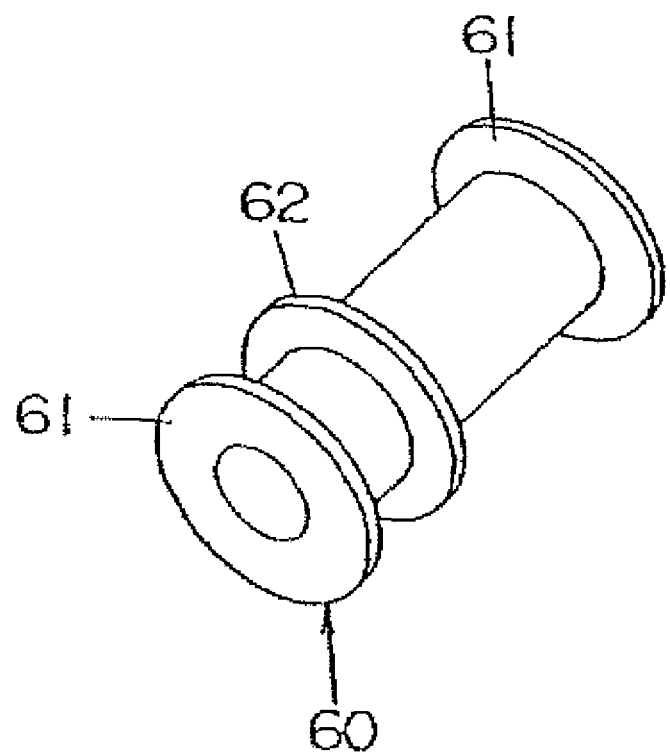
FIG. 68 is a perspective view of a coil bobbin in the same.
Figure 69A:
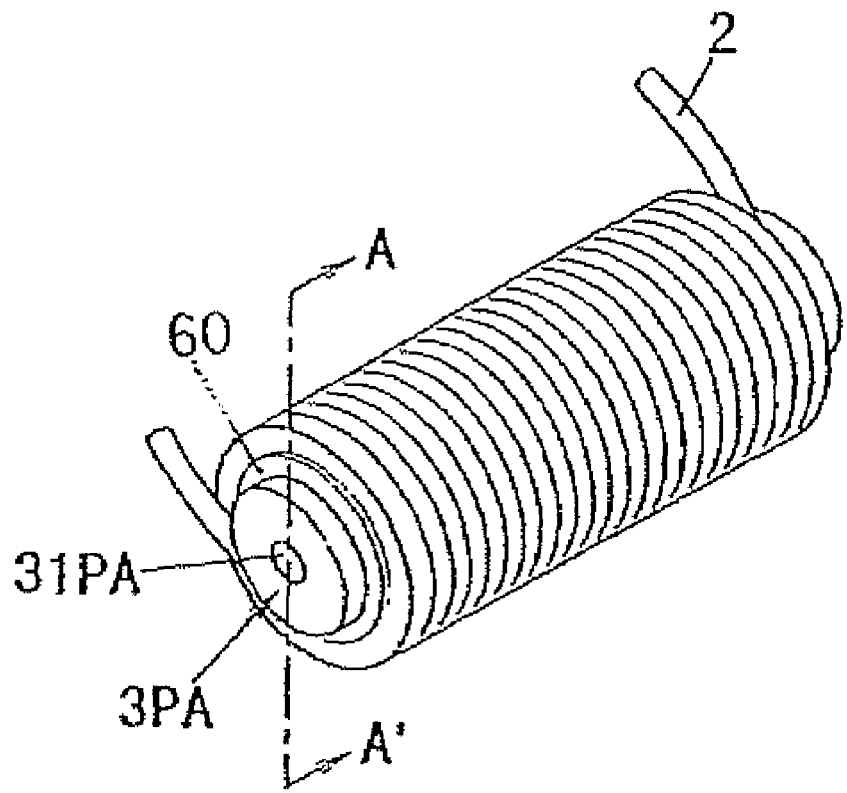
FIG. 69 illustrates a perspective view and a cross sectional view of a conventional electromagnetic device.
Figure 69B:
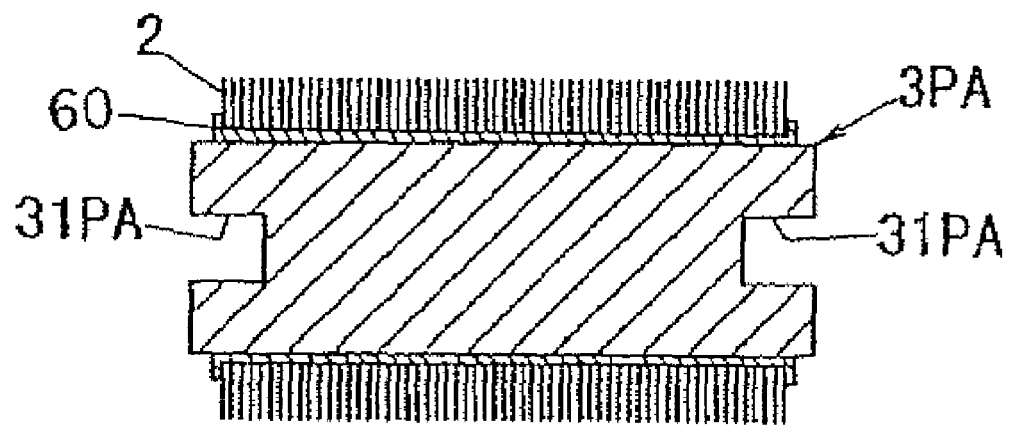

The welding joiner 70 is securely coupled to the insulation coated wire 8 when pressed and welded between welding electrodes 78 as shown in FIG. 64b, thus holding but not detaching from the insulation coated wire 8 and giving the joint of improved stability and durability. Also, as its length from the base portion 71 is equal or slightly greater than the diameter of the insulation coated wire 8, the positional error inhibitor portion 74 of the welding joiner 70 can certainly inhibit any further dislocation of the insulation coated wire 8.

Accordingly, no detachment of the insulation coated wire 8 from the welding joiner 70 will be allowed. Moreover, as the positional error inhibitor portion 74 is spaced by a distance from the folded portion 72, any short-circuit between the positional error inhibitor portion 74 and the folded portion 72 will be disallowed. This allows the extending portion 73 to emit a degree of Joule heat generated by the application of welding energy and transferred from the folded portion 72 thus fusing and removing the insulation coating of the coated wire 8.

INDUSTRIAL UTILIZATION

As set forth above, the electromagnetic device, the high-voltage generating device, and the method for fabricating the electromagnetic device according to the present invention are favorably applicable to and can contribute to the reduction of the size or thickness of a pulse transformer also called an igniter for starting a common high intensity discharge lamp.

What is claimed is:

1. An electromagnetic device comprising:
   a magnetic core having a curved side and a flat rectangular wire conductor being wound in an edge-wise winding form directly contacting the curved side of the magnetic core, wherein the magnetic core has a bottomed hole provided in each end thereof and the hole being tapered.

2. An electromagnetic device according to claim 1, wherein the magnetic core has an elliptical shape in a cross section.

3. A method for making an electromagnetic device comprising a magnetic core having a curved side and a flat rectangular wire conductor being wound in an edge-wise winding form directly contacting the curved side of the magnetic core, the method comprising:
   winding the flat rectangular wire conductor in the edge-wise winding form directly contacting the magnetic core; and
   fixedly joining ends of the flat rectangular wire conductor provided in the edge-wise winding form to corresponding terminals which are provided integrally on a single metal strip,
   wherein as the ends of the flat rectangular wire conductor have been fixedly joined to the corresponding terminals of the metal strip, a redundancy of the metal strip is separated from the terminals to electrically isolate the ends of the flat rectangular wire conductor from the metal strip.

4. The method for making an electromagnetic device according to claim 3, wherein the magnetic core has an elliptical shape in a cross section.

* * * * *

UNITED STATES PATENT AND TRADEMARK OFFICE
CERTIFICATE OF CORRECTION

PATENT NO.         : 7,394,340 B2                                    Page 1 of 1
APPLICATION NO.    : 11/548353
DATED              : July 1, 2008
INVENTOR(S)        : H. Kakehashi et al.

It is certified that error appears in the above-identified patent and that said Letters Patent is hereby corrected as shown below:

On the cover page Item (75), Inventors, "Kinutant" should be --Kinutani--.

Signed and Sealed this

Sixth Day of January, 2009

JON W. DUDAS
*Director of the United States Patent and Trademark Office*